(12) United States Patent
Fischer et al.

US007718694B2

(10) Patent No.: US 7,718,694 B2
(45) Date of Patent: *May 18, 2010

(54) COMPOSITIONS AND METHODS FOR THERAPY FOR DISEASES CHARACTERIZED BY DEFECTIVE CHLORIDE TRANSPORT

(75) Inventors: Horst Fischer, Albany, CA (US); Beate Illek, Albany, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 303 days.

This patent is subject to a terminal disclaimer.

(21) Appl. No.: 10/769,619

(22) Filed: Jan. 30, 2004

(65) Prior Publication Data

US 2004/0197272 A1 Oct. 7, 2004

Related U.S. Application Data

(60) Continuation-in-part of application No. 09/982,315, filed on Oct. 17, 2001, now Pat. No. 7,335,683, which is a division of application No. 09/174,077, filed on Oct. 16, 1998, now Pat. No. 6,329,422, which is a continuation-in-part of application No. 08/951,912, filed on Oct. 16, 1997, now Pat. No. 5,972,995.

(51) Int. Cl.
*A61K 31/35* (2006.01)
*A61K 31/21* (2006.01)
(52) U.S. Cl. .................. 514/474; 514/27; 514/456; 514/513; 514/826; 514/851
(58) Field of Classification Search .................. 514/27, 514/456, 513, 826, 851
See application file for complete search history.

(56) References Cited

U.S. PATENT DOCUMENTS

| | | | | |
|---|---|---|---|---|
| 3,781,423 A | * | 12/1973 | Aoka et al. ................. | 514/474 |
| 3,816,466 A | * | 6/1974 | Von Strandtmann et al. | 549/389 |
| 4,514,421 A | * | 4/1985 | Herschler ................... | 514/711 |
| 5,122,536 A | * | 6/1992 | Perricone ................... | 514/474 |
| 5,589,182 A | | 12/1996 | Tashiro et al. .............. | 424/423 |
| 5,639,661 A | | 6/1997 | Welsh et al. ................ | 435/252.3 |
| 5,650,433 A | | 7/1997 | Watanabe et al. ........... | 514/456 |
| 5,733,926 A | | 3/1998 | Gorbach ..................... | 514/456 |
| 5,756,538 A | | 5/1998 | Cassels et al. .............. | 514/456 |
| 5,807,586 A | * | 9/1998 | Jackson et al. .............. | 424/630 |
| 5,972,995 A | | 10/1999 | Fischer et al. .............. | 514/456 |
| 6,329,422 B1 | | 12/2001 | Fischer et al. .............. | 514/456 |

FOREIGN PATENT DOCUMENTS

| | | |
|---|---|---|
| JP | 87-105816 | 3/1987 |
| JP | 93-330545 | 9/1993 |
| JP | 94-277493 | 2/1994 |
| JP | 95-135875 | 3/1995 |
| RU | 2008015 | 2/1994 |
| WO | WO 01/15777 | * 3/2001 |

OTHER PUBLICATIONS

Anderson et al., "Generation of cAMP-Activated Chloride Currents by Expression of CFTR," *Science* 251: 679-682, 1991.
Brown et al., "Chemical chaperones correct the mutant phenotype of the ΔF508 cystic fibrosis transmembrane conductance regulatory protein," *Cell Stress & Chaperones* 1(2): 117-125, 1996.
Brown, R.K. et al., "Pulmonary dysfunction in cystic fibrosis is associated with oxidative stress," *Eur. Respir. J.* 9: 334-339, 1996.
Chanvitayapongs, S. et al., "Amelioration of oxidative stress by antioxidants and resveratrol in PC12 cells," *NeuroReport* 8(6): 1499-1502, Apr. 14, 1997.
Congden, P.J. et al., "Vitamin status in treated patients with cystic fibrosis," *Archives of Disease in Childhood* 56: 708-714, 1981.
Fischer, H. et al., "Partial restoration of defective chloride conductance in ΔF508 CF mice by trimethylamine oxide,"*Am. J. Physiol. Lung Cell Mol. Physiol.* 281: L52-L57, 2001.
Hwang et al., "Genistein potentiates wild-type and ΔF508-CFTR channel activity," *American Journal of Physiology* 273(3, part 1): C988-C998, 1997.
Illek et al., "cAMP-independent activation of CFTR Cl channels by the tyrosine kinase inhibitor genistein," *Cell Physiol.* 37: C886-C893, 1995.
Illek, B. et al., "Defective function of the cystic fibrosis-causing missense mutation G551D is recovered by genistein," *Am. J. Physiol. Cell Physiol.* 277: C833-C839, 1999.
Knowles et al., "In Vivo Nasal Potential Difference: Techniques and Protocols for Assessing Efficacy of Gene Transfer in Cystic Fibrosis," *Human Gene Therapy* 6: 445-455, 1995.
Laurans, M. et al., "Vitamines Et Oligo-Éléments Dans La Mucoviscidose," *Ann Pédiatr (Paris)* 43(3): 218-223, 1996.
McGahan, M.C. et al., "Stimulation of Transepithelial Sodium and Chloride Transport by Ascorbic Acid," *Biochimica et Biophysica Acta* 689: 385-392, 1982.
Riordan et al., "Identification of the Cystic Fibrosis Gene: Cloning and Characterization of Complementary DNA," *Science* 245: 1066-1073, 1989.
Rubenstein et al., "In Vitro Pharmacologic Restoration of CFTR-mediated Chloride Transport with Sodium 4-Phenylbutyrate in Cystic Fibrosis Epithelial Cells," *J. Clin. Invest.* 100(10): 2457-2465, 1997.
Scott and Cooperstein, "Ascorbic acid stimulates chloride transport in the amphibian cornea," *Investigative Ophtalmology* 14(10): 763-766, 1975.

(Continued)

*Primary Examiner*—Traviss C McIntosh, III
(74) *Attorney, Agent, or Firm*—Seed IP Law Group PLLC

(57) ABSTRACT

Compositions and methods for therapy of cystic fibrosis, asthma, and other conditions characterized by defective chloride transport are provided. The compositions comprise one or more compounds such as flavones and/or isoflavones, ascorbate and/or derivatives thereof capable of stimulating chloride transport in epithelial tissues. Therapeutic methods involve the administration (e.g., orally or via inhalation) of such compositions to a patient afflicted with cystic fibrosis, asthma, and/or another condition responsive to stimulation of chloride transport.

10 Claims, 26 Drawing Sheets

OTHER PUBLICATIONS

Sheppard et al., "Mutations in CFTR associated with mild-disease-form CI channels with altered pore properties," *Nature 362*: 160-164, 1993.

Smith, "Treatment of cystic fibrosis based on understanding CFTR," *J. Inher. Metab. Dis. 18*: 508-516, 1995.

Soleas, G.J. et al., "Wine as a Biological Fluid: History, Production, and Role in Disease Prevention," *J. Clin. Lab. Analysis 11*: 287-313, 1997.

Uden, S. et al., "Rationale for Antioxidant Therapy in Pancreatitis and Cystic Fibrosis," *Advances in Experimental Medicine and Biology 264*: 555-572, 1990.

Alton, E.W.F.W. et al., "Nasal potential difference: a clinical diagnostic test for cystic fibrosis," *Eur. Respir. J. 3*: 922-926, 1990.

Bebok, Z. et al., "Reactive Oxygen Nitrogen Species Decrease Cystic Fibrosis Transmembrane Conductance Regulator Expression and cAMP-mediated Cl$^-$ Secretion in Airway Epithelia," *The Journal of Biological Chemistry 277*(45): 43041-43049, Nov. 8, 2002.

Boucher, R.C., "Regulation of airway surface liquid volume by human airway epithelia," *Pflugers Arch.—Eur. J. Physiol 445*: 495-498, 2003.

Brodsky, J.L., "Chaperoning the maturation of the cystic fibrosis transmembrane conductance regulator," *Am. J. Physiol. Lung Cell Mol. Physiol. 281*: L39-L42, 2001.

Brown, C.R. et al., "Strategies for Correcting the ΔF508 CFTR Protein-Folding Defect," *Journal of Bioenergetics and Biomembranes 29*(5): 491-502, 1997.

Brown, L.A.S. et al., "Ascorbate deficiency and oxidative stress in the alveolar type II cell," *Am. J. Physiol. Lung Cell Mol. Physiol. 273*: L782-L788, 1997.

Calikoglu, M. et al., "The Levels of Serum Vitamin C, Malonyldialdehyde and Erythrocyte Reduced Glutathione in Chronic Obstructive Pulmonary Disease and in Healthy Smokers," *Clin . Chem. Lab. Med. 40*(10): 1028-1031, 2002.

Clarke, L.L. et al., "Increased Survival of CFTR Knockout Mice with an Oral Osmotic Laxative," *Laboratory Animal Science 46*(6): 612-618, Dec. 1996.

Cotten, J.F. et al., "Covalent Modification of the Regulatory Domain Irreversibly Stimulates Cystic Fibrosis Transmembrane Conductance Regulator," *The Journal of Biological Chemistry 272*(41): 25617-25622, Oct. 10, 1997.

Cross, C.E. et al., "Oxidative damage to plasma constituents by ozone," *FEBS Letters 298*(2-3): 269-272, Feb. 1992.

Cross, C.E. et al., "Oxidative stress and abnormal cholesterol metabolism in patients with adult respiratory distress syndrome," *J. Lab. Clin. Med. 115*(4): 396-404, 1990.

Dalemans, W. et al., "Altered chloride ion channel kinetics associated with the ΔF508 cystic fibrosis mutation," *Nature 354*: 526-528, Dec. 19, 1991.

Diplock, A.T., "Safety of antioxidant vitamins and β-carotene," *Am. J. Clin. Nutr. 62*(suppl.): 1510S-1516S, 1995.

Egan, M.E. et al., "Calcium-pump inhibitors induce functional surface expression of ΔF508-CFTR protein in cystic fibrosis epithelial cells," *Nature Medicine 8*(5): 485-492, May 2002.

Fischer, H. et al., "CFTR Displays Voltage Dependence and Two Gating Modes during Stimulation," *J. Gen. Physiol. 104*: 541-566, Sep. 1994.

Fischer, H. et al., "The actin filament disrupter cytochalasin D activates the recombinant cystic fibrosis transmembrane conductance regulator Cl$^-$ channel in mouse 3T3 fibroblasts," *Journal of Physiology 489*(3): 745-754, 1995.

Fischer, H., "Electrophysiological Approach to Studying CFTR," *Methods in Molecular Medicine 70*: 49-65, 2002.

Food and Nutrition Board Institute of Medicine, *Dietary Reference Intakes for Vitamin C, Vitamin E, Selenium and Carotenoids*, Chapter 5, National Academy Press, Washington D.C, 2000, pp. 95-185.

Harrington, M.A. et al., "Cysteine Residues in the Nucleotide Binding Domains Regulate the Conductance State of CFTR Channels," *Biophysical Journal 82*: 1278-1292, Mar. 2002.

Harrington, M.A. et al., "Redox Reagents and Divalent Cations Alter the Kinetics of Cystic Fibrosis Transmembrane Conductance Regulator Channel Gating," *The Journal of Biological Chemistry 274*(39): 27536-27544, Sep. 24, 1999.

Haws, C. et al., "CFTR in Calu-3 human airway cells: channel properties and role in cAMP-activated Cl$^-$ conductance," *Am. J. Physiol. Lung Cell Mol. Physiol. 266*: L502-L512, 1994.

Hornig, D., "Distribution of Ascorbic Acid, Metabolites and Analogues in Man and Animals," *Annals of the New York Academy of Sciences 258*: 103-118, 1975.

Huang, P. et al., "Compartmentalized autocrine signaling to cystic fibrosis transmembrane conductance regulator at the apical membrane of airway epithelial cells," *Proc. Natl. Acad. Sci. USA 98*(24): 14120-14125, Nov. 20, 2001.

Illek, B. et al., "Flavonoids stimulate Cl conductance of human airway epithelium in vitro and in vivo," *Am. J. Physiol. Lung Cell Mol. Physiol. 275*: L902-L910, 1998.

Illek, B. et al., "Genetic Disorders of Membrane Transport. II. Regulation of CFTR by small molecules including $HCO_3^-$," *Am. J. Physiol. Gastrointes. Liver Physiol. 275*: G1221-G1226, 1998.

Jayaraman, S. et al., "Submucosal gland secretions in airways from cystic fibrosis patients have normal [Na$^+$] and pH but elevated viscosity,"+*Proc. Natl. Acad. Sci. USA 98*(14): 8119-8123, Jul. 3, 2001.

Jefferson, D.M. et al., "Expression of normal and cystic fibrosis phenotypes by continuous airway epithelial cell lines," *Am. J. Physiol. Lung Cell Mol. Physiol. 259*: L496-L505, 1990.

Kelly, F.J. et al., "Altered lung antioxidant status in patients with mild asthma," *Lancet 354*: 482-483, Aug. 7, 1999.

Kodavanti, U.P. et al., "Antioxidants in Bronchoalveolar Lavage Fluid Cells Isolated from Ozone—Exposed Normal and Ascorbate-Deficient Guinea Pigs," *Experimental Lung Research 22*: 435-448, 1996.

Köttgen, M. et al., "N-Acetyl-$_L$-cysteine and its derivatives activate a Cl$^-$ conductance in epithelial cells,"*Pflügers Arch—Eur. J. Physiol. 431*: 549-555, 1996.

Levine, M. et al., "Vitamin C pharmacokinetics in healthy volunteers: Evidence for a recommended dietary allowance," *Proc. Natl. Acad. Sci. USA 93*: 3704-3709, Apr. 1996.

Lykkesfeldt, J. et al., "Ascorbate is depleted by smoking and repleted by moderate supplementation: a study in male smokers and non-smokers with matched dietary antioxidant intakes," *Am. J. Clin. Nutr. 71*: 530-536, 2000.

Maulén, N.P. et al., "Up-regulation and Polarized Expression of the Sodium-Ascorbic Acid Transporter SVCT1 in Post-confluent Differentiated CaCo-2 Cells," *The Journal of Biological Chemistry 278*(11): 9035-9041, Mar. 14, 2003.

McCray, P.B. et al., "Efficient killing of inhaled bacteria in ΔF508 mice: role of airway surface liquid composition," *Am. J. Physiol. Lung Cell Mol. Physiol. 277*: L183-L190, 1999.

Menzel, D.B., "Antioxidant Vitamins and Prevention of Lung Disease," *Annals of the New York Academy of Sciences 669*: 141-155, 1992.

Nishikimi, M. et al., "Cloning and Chromosomal Mapping of the Human Nonfunctional Gene for $_L$-Gulono-γ-lactone Oxidase, the Enzyme for $_L$-Ascorbic Acid Biosynthesis Missing in Man," *The Journal of Biological Chemistry 269*(18): 13685-13688, May 6, 1994.

Preston, A.M. et al., "Influence of environmental tobacco smoke on vitamin C status in children," *Am. J. Clin. Nutr. 77*:167-172, 2003.

Rumsey, S.C. et al., "Absorption, transport, and disposition of ascorbic acid in humans," *Journal of Nutritional Biochemistry 9*: 116-130, Mar. 1998.

Rumsey, S.C. et al., "Specificity of Ascorbate Analogs for Ascorbate Transport. Synthesis and Detection of [$^{125}$I]6-Deoxy-6-Iodo-$_L$-Ascorbic Acid and Characterization of its Ascorbate-Specific Transport Properties," *The Journal of Biological Chemistry 274*(33): 23215-23222, Aug. 13, 1999.

Sachs, L.A. et al., "Effects of Media on Differentiation of Cultured Human Tracheal Epithelium," *In Vitro Cell. Dev. Biol.—Animal 39*: 56-62, Jan./Feb. 2003.

Schwartz, J. et al., "Relationship between dietary vitamin C intake and pulmonary function in the First National Health and Nutrition Examination Survey (NHANES I)," *Am. J. Clin. Nutr.* 59: 110-114, 1994.

Slade, R. et al., "Comparison of Antioxidant Substances in Bronchoalveolar Lavage Cells and Fluid from Humans, Guinea Pigs, and Rats," *Experimental Lung Research* 19: 469-484, 1993.

Snyder, A.H. et al., "Acute Effects of Aerosolized S-Nitrosoglutathione in Cystic Fibrosis," *Am. J. Respir. Crit. Care Med.* 165: 922-926, 2002.

Sotiriou, S. et al., "Ascorbic-acid transporter Slc23a1 is essential for vitamin C transport into the brain and for perinatal survival," *Nature Medicine* 8(5): 514-517, May 2002.

Tsukaguchi, H. et al., "A family of mammalian $Na^+$-dependent $_L$-ascorbic acid transporters," *Nature* 399: 70-75, May 6, 1999.

Van der Vliet, A. et al., "Determination of low-molecular-mass antioxidant concentrations in human respiratory tract lining fluids," *Am. J. Physiol. Lung Cell Mol. Physiol.* 276: L289-L296, 1999.

Widdicombe, J.H., "Relationships among the Composition of Mucus, Epithelial Lining Liquid, and Adhesion of Microorganisms," *Am. J. Respir. Crit. Care Med.* 151: 2088-2093, 1995.

Widdicombe, J.H., "Altered NaCl Concentration of Airway Surface Liquid in Cystic Fibrosis," *News Physiol. Sci.* 14: 126-127, Jun. 1999.

Willis, R.J. et al., "Extracellular Ascorbic Acid in Lung," *Biochimica et Biophysica Acta* 444: 108-117, 1976.

Winklhofer-Roob, B.M. et al., "Plasma vitamin C concentrations in patients with cystic fibrosis: evidence of associations with lung inflammation," *Am. J. Clin. Nutr.* 65: 1858-1866, 1997.

Yamamoto, I. et al., "Bioavailability and Biological Activity of $_L$-Ascorbic Acid 2-O-α-Glucoside," in *Proceedings of the 1st International Congress on Vitamins and Biofactors in Life Science in Kobe, 1991*, Kobayashi, T. (Ed.), Center for Academic Publications, Tokyo, Japan, 1992, pp. 161-164.

van der Vliet et al., "Oxidative Stress in Cystic Fibrosis: Does It Occur and Does It Matter," Advances in Pharmacology 38:491-513, 1997.

\* cited by examiner

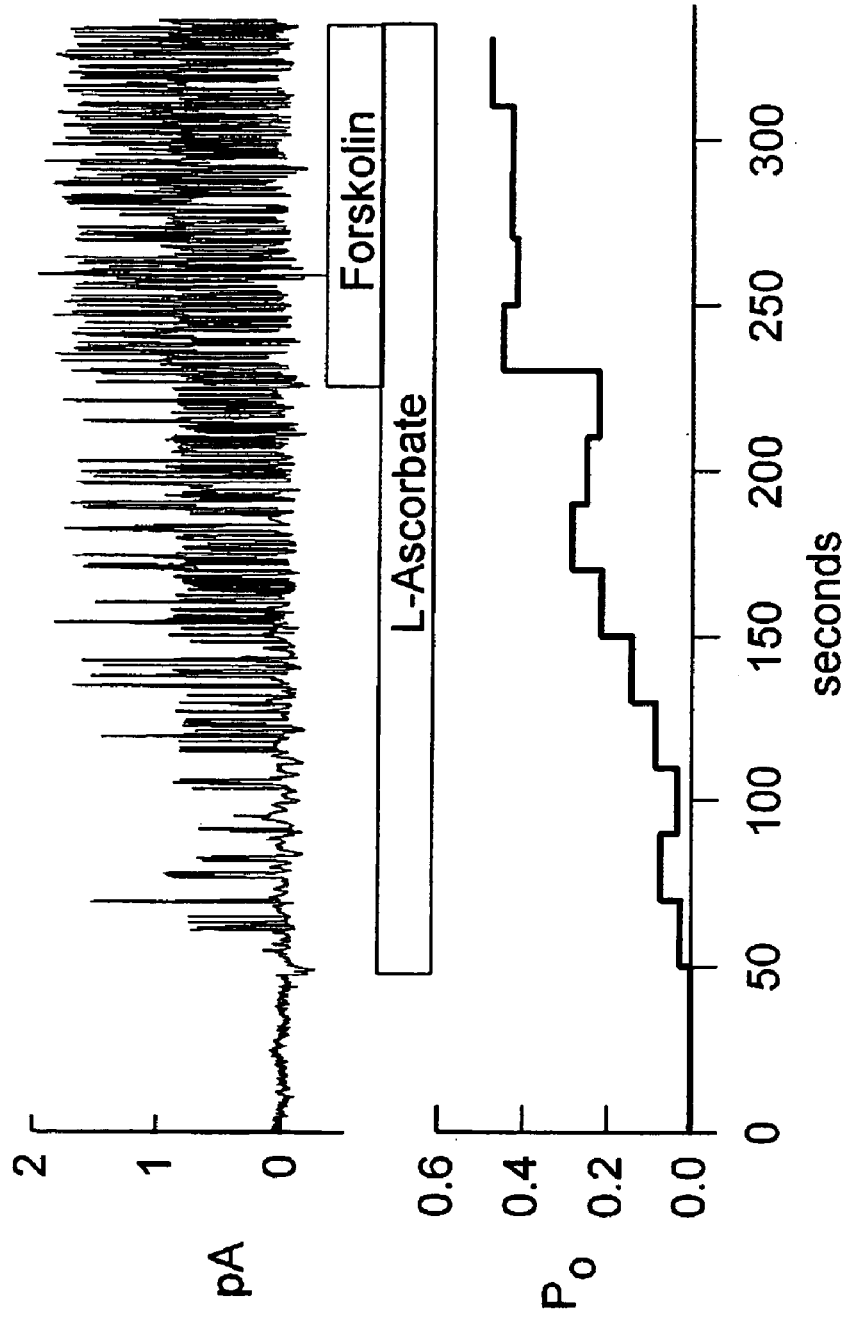

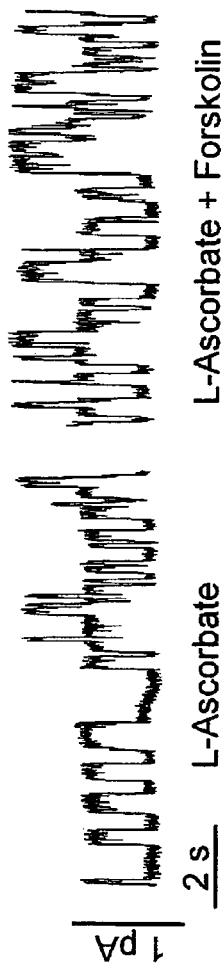
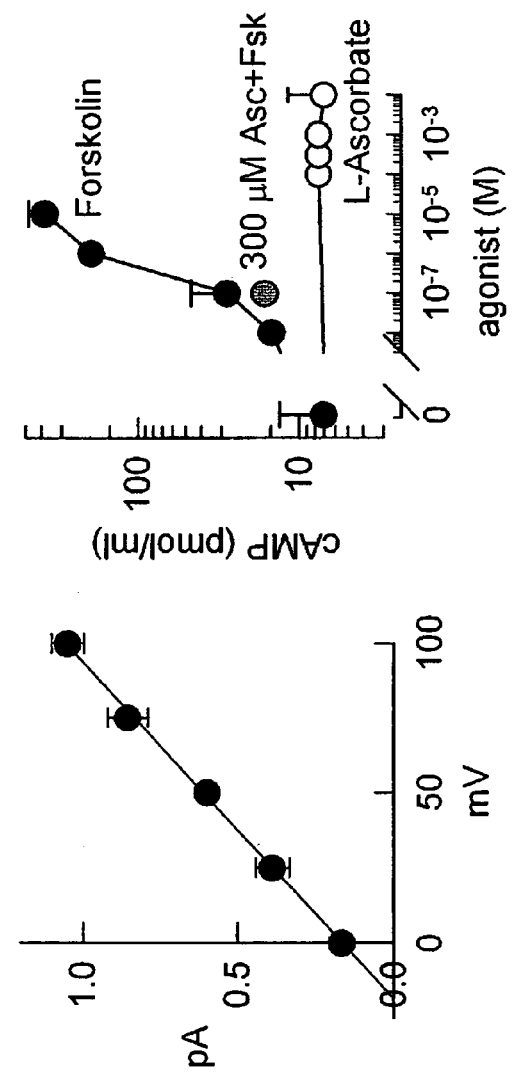
Fig. 20C
Fig. 20D
Fig. 20E

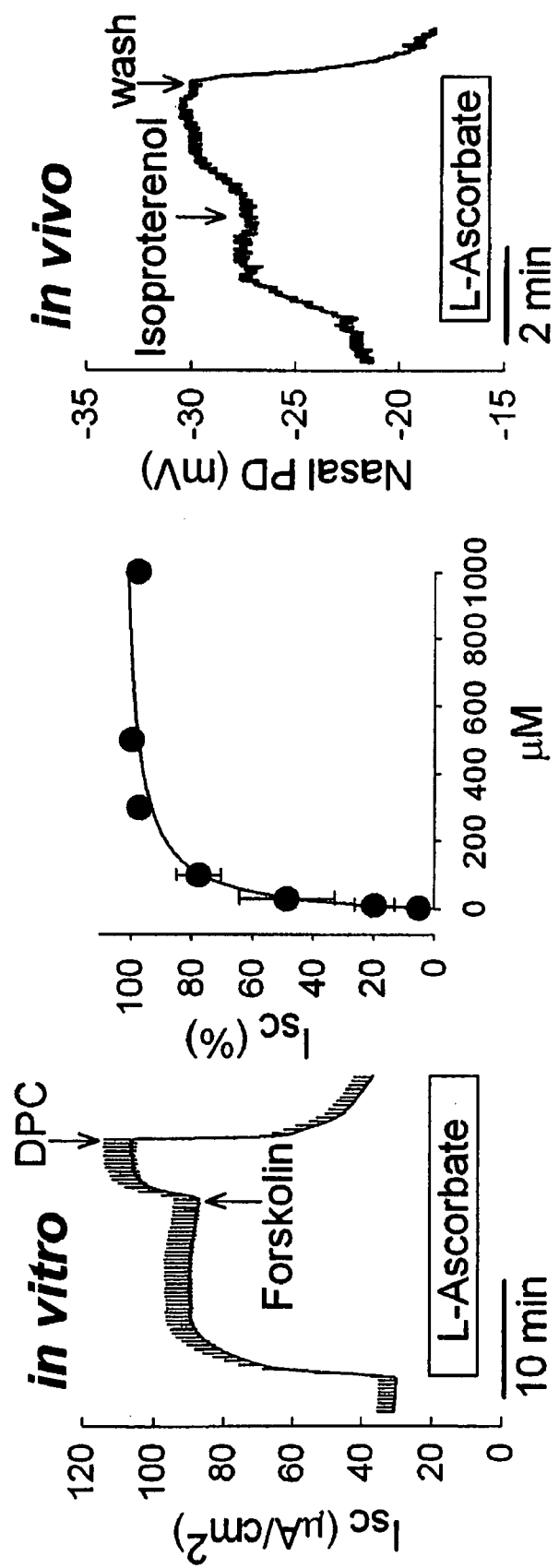

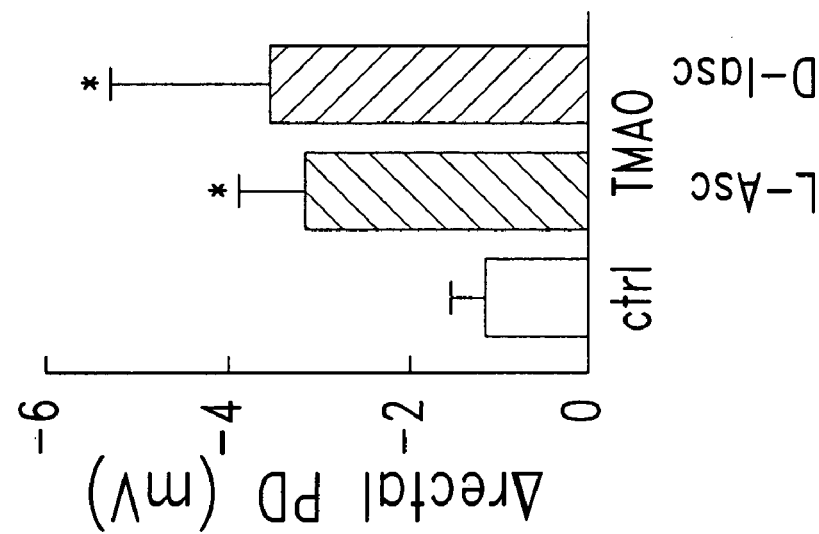
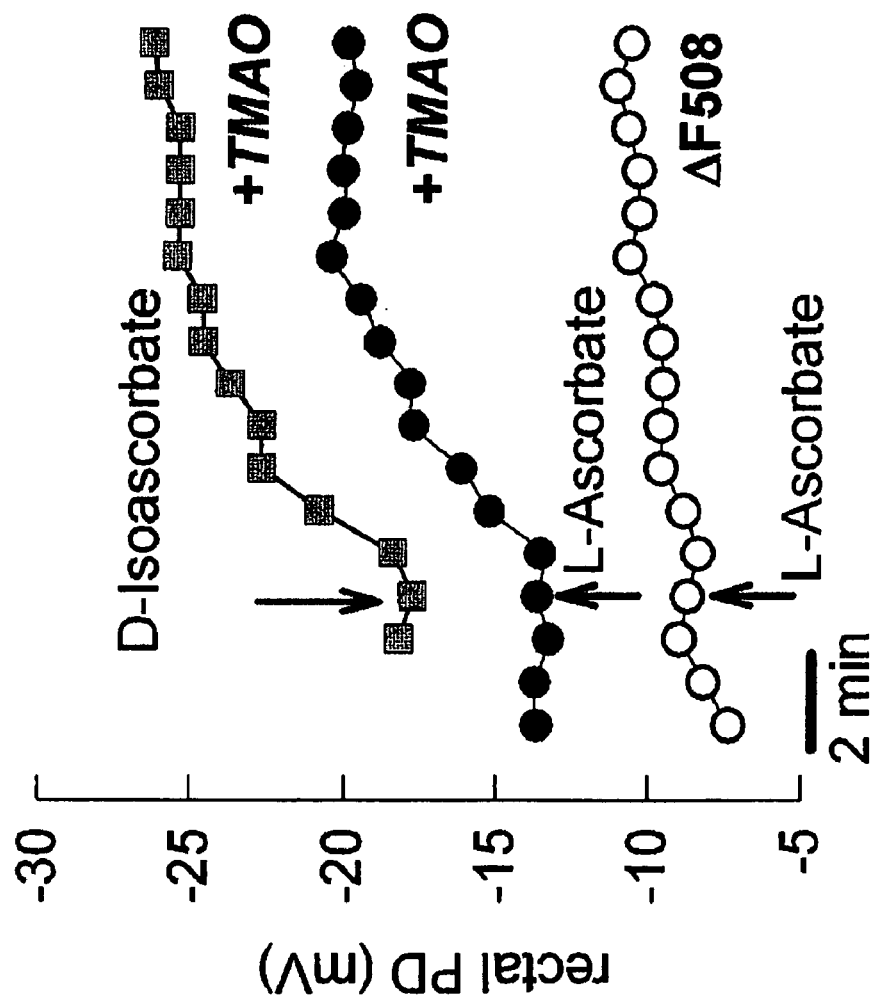
Fig. 24A
Fig. 24B

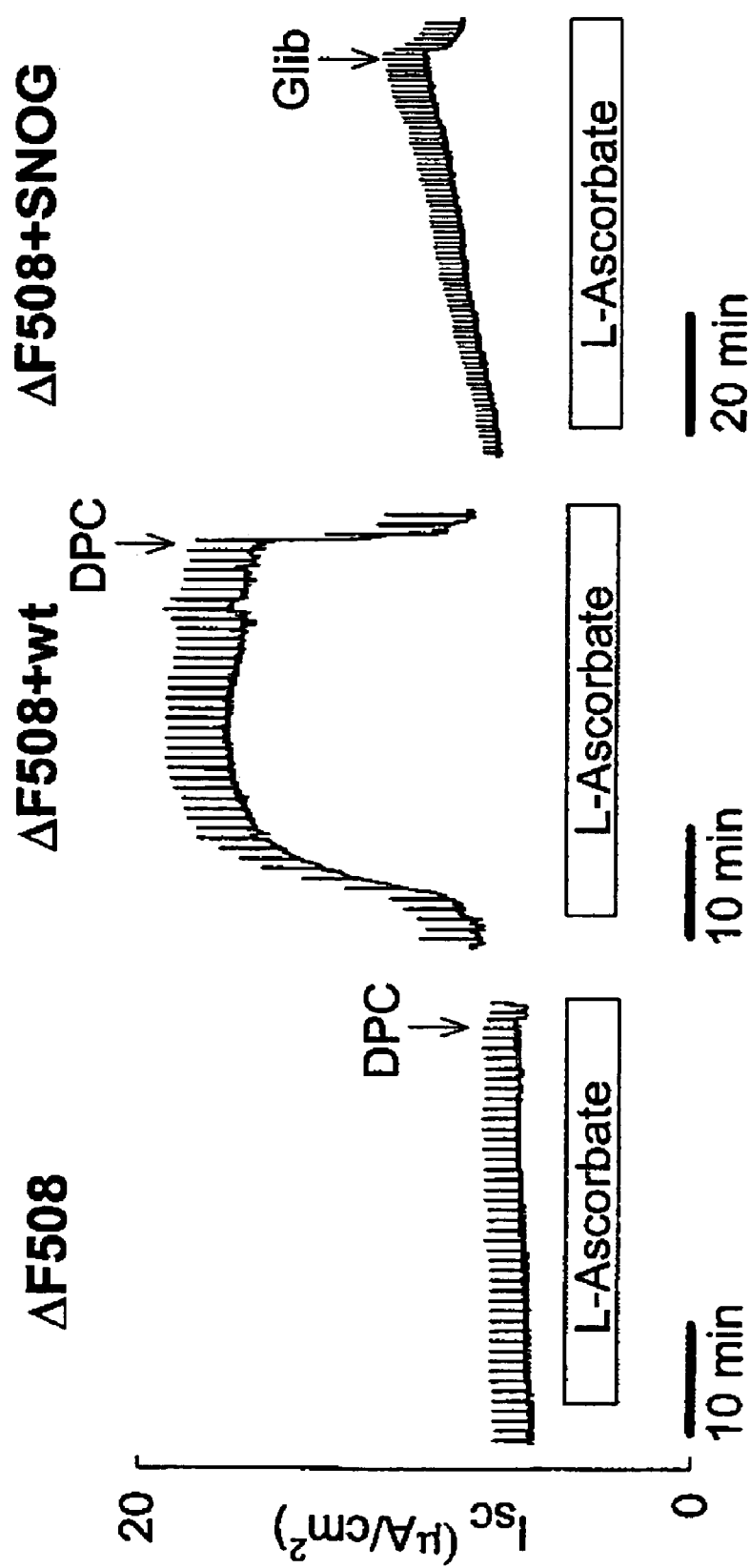

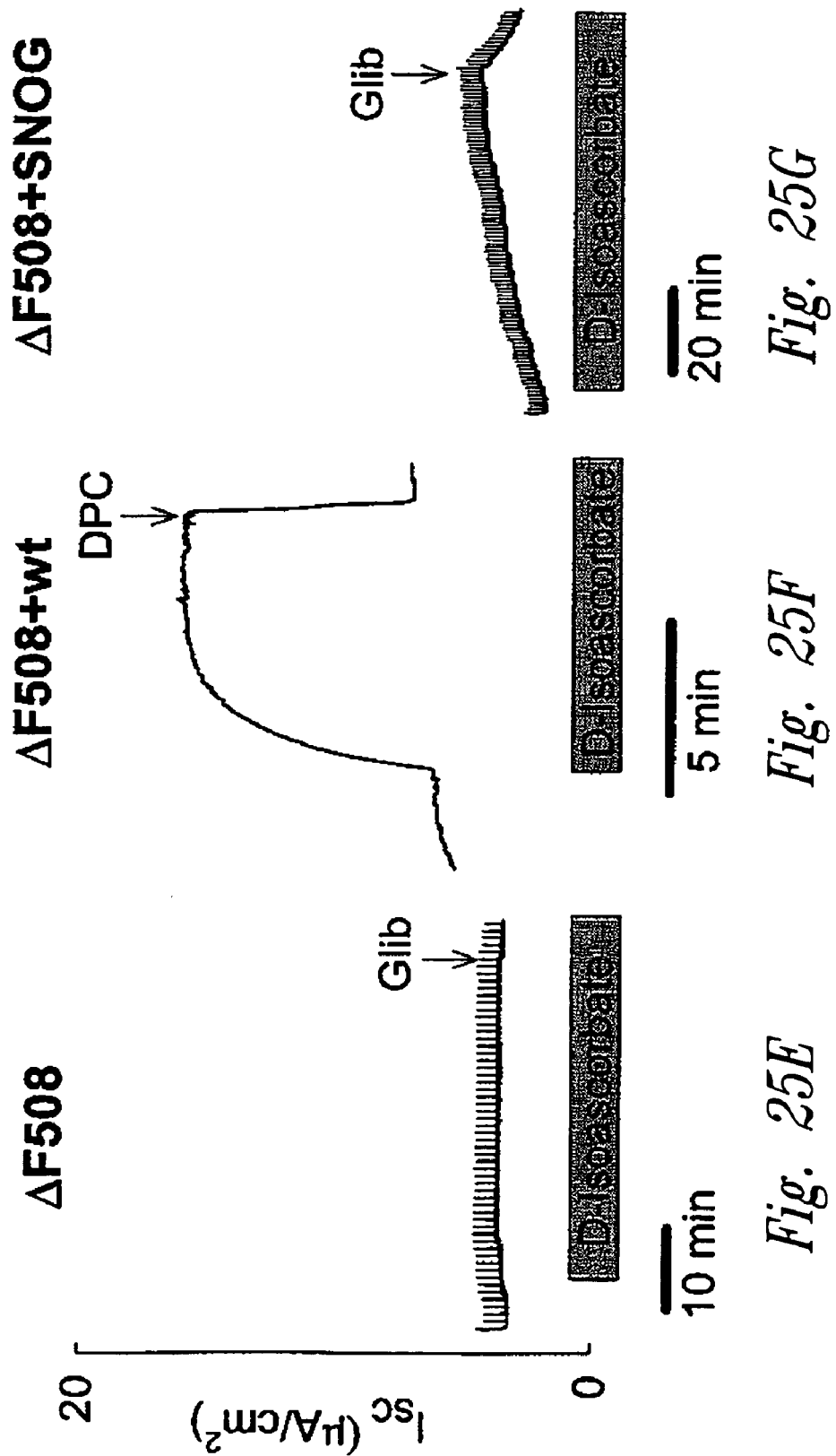

SEQUENCE LISTING

```
<160> NUMBER OF SEQ ID NOS: 12

<210> SEQ ID NO 1
<211> LENGTH: 6129
<212> TYPE: DNA
<213> ORGANISM: Homo sapiens

<400> SEQUENCE: 1
aattggaagc aaatgacatc acagcaggtc agagaaaaag ggttgagcgg caggcaccca        60
gagtagtagg tctttggcat taggagcttg agcccagacg gccctagcag ggaccccagc       120
gcccgagaga ccatgcagag gtcgcctctg gaaaaggcca gcgttgtctc caaactttt        180 ttcagctgga ccagaccaat tttgaggaaa ggatacagac agcgcctgga attgtcagac       240
atataccaaa tccttctgt tgattctgct gacaatctat ctgaaaaatt ggaaagagaa        300
tgggatagag agctggcttc aaagaaaaat cctaaactca ttaatgccct tcggcgatgt       360
tttttctgga gatttatgtt ctatggaatc tttttatatt taggggaagt caccaaagca       420
gtacagcctc tcttactggg aagaatcata gcttcctatg acccggataa caaggaggaa       480
cgctctatcg cgatttatct aggcatagc ttatgccttc tctttattgt gaggacactg        540
ctcctacacc cagccatttt tggccttcat cacattggaa tgcagatgag aatagctatg       600
```

```
tttagtttga tttataagaa gactttaaag ctgtcaagcc gtgttctaga taaaataagt    660
attggacaac ttgttagtct cctttccaac aacctgaaca aatttgatga aggacttgca    720
ttggcacatt tcgtgtggat cgctcctttg caagtggcac tcctcatggg gctaatctgg    780
gagttgttac aggcgtctgc cttctgtgga cttggtttcc tgatagtcct tgccctttt     840 caggctgggc tagggagaat gatgatgaag tacagagatc agagagctgg gaagatcagt    900
gaaagacttg tgattacctc agaaatgatt gaaaatatcc aatctgttaa ggcatactgc    960
tgggaagaag caatgaaaaa atgattgaa aacttaagac aaacagaact gaaactgact    1020
cggaaggcag cctatgtgag atacttcaat agctcagcct tcttcttctc agggttcttt    1080
gtggtgtttt tatctgtgct tccctatgca ctaatcaaag gaatcatcct ccggaaaata    1140
ttcaccacca tctcattctg cattgttctg cgcatggcgg tcactcggca atttccctgg    1200
gctgtacaaa catggtatga ctctcttgga gcaataaaca aaatacagga tttcttacaa    1260
aagcaagaat ataagacatt ggaatataac ttaacgacta cagaagtagt gatggagaat    1320
gtaacagcct tctgggagga gggatttggg gaattatttg agaaagcaaa acaaaacaat    1380
aacaatagaa aaacttctaa tggtgatgac agcctcttct tcagtaattt ctcacttctt    1440
ggtactcctg tcctgaaaga tattaatttc aagatagaaa gaggacagtt gttggcggtt    1500
gctggatcca ctggagcagg caagacttca cttctaatga tgattatggg agaactggag    1560
ccttcagagg gtaaaattaa gcacagtgga agaatttcat tctgttctca gttttcctgg    1620
attatgcctg gcaccattaa agaaaatatc atctttggtg tttcctatga tgaatataga    1680
tacagaagcg tcatcaaagc atgccaacta gaagaggaca tctccaagtt gcagagaaa     1740 gacaatatag ttcttggaga aggtggaatc acactgagtg gaggtcaacg agcaagaatt    1800 tcttagcaa gagcagtata caaagatgct gatttgtatt tattagactc cctttgga     1860 tacctagatg tttaacaga aaagaaata tttgaaagct gtgtctgtaa actgatggct    1920
aacaaaacta ggattttggt cacttctaaa atggaacatt taaagaaagc tgacaaaata    1980 ttaatttga atgaaggtag cagctatttt tatgggacat tttcagaact ccaaaatcta    2040
cagccagact ttagctcaaa actcatggga tgtgattctt tcgaccaatt tagtgcagaa    2100
agaagaaatt caatcctaac tgagaccta caccgtttct cattagaagg atgctcct     2160 gtctcctgga cagaaacaaa aaaacaatct tttaaacaga ctggagagtt tggggaaaaa    2220
aggaagaatt ctattctcaa tccaatcaac tctatacgaa aattttccat tgtgcaaaag    2280
actcccttac aaatgaatgg catcgaagag gattctgatg agcctttaga gagaaggctg    2340
tccttagtac cagattctga gcagggagag gcgatactgc ctcgcatcag cgtgatcagc    2400
actggcccca cgcttcaggc acgaaggagg cagtctgtcc tgaacctgat gacacactca    2460
gttaaccaag gtcagaacat tcaccgaaag acaacagcat ccacacgaaa agtgtcactg    2520
gcccctcagg caaacttgac tgaactggat atatattcaa gaaggttatc tcaagaaact    2580
ggcttggaaa taagtgaaga aattaacgaa gaagacttaa aggagtgcct tttgatgat    2640 atggagagca taccagcagt gactacatgg aacacatacc ttcgatatat tactgtccac    2700
aagagcttaa ttttgtgct aatttggtgc ttagtaattt ttctggcaga ggtggctgct    2760
tctttggttg tgctgtggct ccttggaaac actcctcttc aagacaaagg gaatagtact    2820
catagtagaa ataacagcta tgcagtgatt atcaccagca ccagttcgta ttatgtgttt    2880
tacatttacg tgggagtagc cgacactttg cttgctatgg gattcttcag aggtctacca    2940
```

```
ctggtgcata ctctaatcac agtgtcgaaa attttacacc acaaaatgtt acattctgtt    3000
cttcaagcac ctatgtcaac cctcaacacg ttgaaagcag gtgggattct taatagattc    3060
tccaaagata tagcaatttt ggatgacctt ctgcctctta ccatatttga cttcatccag    3120
ttgttattaa ttgtgattgg agctatagca gttgtcgcag ttttacaacc ctacatcttt    3180
gttgcaacag tgccagtgat agtggctttt attatgttga gagcatattt cctccaaacc    3240
tcacagcaac tcaaacaact ggaatctgaa ggcaggagtc caattttcac tcatcttgtt    3300
acaagcttaa aaggactatg gacacttcgt gccttcggac ggcagcctta ctttgaaact    3360
ctgttccaca aagctctgaa tttacatact gccaactggt tcttgtacct gtcaacactg    3420
cgctggttcc aaatgagaat agaaatgatt tttgtcatct tcttcattgc tgttaccttc    3480
atttccattt taacaacagg agaaggagaa ggaagagttg gtattatcct gactttagcc    3540
atgaatatca tgagtacatt gcagtgggct gtaaactcca gcatagatgt ggatagcttg    3600
atgcgatctg tgagccgagt ctttaagttc attgacatgc aacagaagg taaacctacc    3660 aagtcaacca aaccatacaa gaatggccaa ctctcgaaag ttatgattat tgagaattca    3720
cacgtgaaga aagatgacat ctggccctca gggggccaaa tgactgtcaa agatctcaca    3780
gcaaaataca cagaaggtgg aaatgccata ttagagaaca tttccttctc aataagtcct    3840
ggccagaggg tgggcctctt gggaagaact ggatcaggga gagtactttt gttatcagct    3900
tttttgagac tactgaacac tgaaggagaa atccagatcg atggtgtgtc ttgggattca    3960
ataactttgc aacagtggag gaaagccttt ggagtgatac cacagaaagt atttattttt    4020
tctggaacat ttagaaaaaa cttggatccc tatgaacagt ggagtgatca agaaatatgg    4080
aaagttgcag atgaggttgg gctcagatct gtgatagaac agtttcctgg gaagcttgac    4140
tttgtccttg tggatggggg ctgtgtccta agccatggcc acaagcagtt gatgtgcttg    4200
gctagatctg ttctcagtaa ggcgaagatc ttgctgcttg atgaacccag tgctcatttg    4260
gatccagtaa cataccaaat aattagaaga actctaaaac aagcatttgc tgattgcaca    4320
gtaattctct gtgaacacag gatagaagca atgctggaat gccaacaatt tttggtcata    4380
gaagagaaca aagtgcggca gtacgattcc atccagaaac tgctgaacga gaggagcctc    4440
ttccggcaag ccatcagccc ctccgacagg gtgaagctct tcccccaccg gaactcaagc    4500
aagtgcaagt ctaagcccca gattgctgct ctgaaagagg agacagaaga agaggtgcaa    4560
gatacaaggc tttagagagc agcataaatg ttgacatggg acatttgctc atggaattgg    4620
agctcgtggg acagtcacct catggaattg gagctcgtgg aacagttacc tctgcctcag    4680
aaaacaagga tgaattaagt tttttttttaa aaagaaaca tttggtaagg ggaattgagg    4740
acactgatat gggtcttgat aaatggcttc ctggcaatag tcaaattgtg tgaaaggtac    4800
ttcaaatcct tgaagattta ccacttgtgt tttgcaagcc agattttcct gaaaacccct    4860
gccatgtgct agtaattgga aaggcagctc taaatgtcaa tcagcctagt tgatcagctt    4920
attgtctagt gaaactcgtt aatttgtagt gttggagaag aactgaaatc atacttctta    4980
gggttatgat taagtaatga taactggaaa cttcagcggt ttatataagc ttgtattcct    5040
ttttctctcc tctccccatg atgtttagaa acacaactat attgtttgct aagcattcca    5100
actatctcat ttccaagcaa gtattagaat accacaggaa ccacaagact gcacatcaaa    5160
atatgcccca ttcaacatct agtgagcagt caggaaagag aacttccaga tcctggaaat    5220
cagggttagt attgtccagg tctaccaaaa atctcaatat ttcagataat cacaatacat    5280
cccttacctg ggaaagggct gttataatct ttcacagggg acaggatggt tcccttgatg    5340
```

-continued

```
aagaagttga tatgccttt  cccaactcca gaaagtgaca agctcacaga cctttgaact  5400
agagtttagc tggaaaagta tgttagtgca aattgtcaca ggacagccct tctttccaca  5460
gaagctccag gtagagggtg tgtaagtaga taggccatgg gcactgtggg tagacacaca  5520
tgaagtccaa gcatttagat gtataggttg atggtggtat gttttcaggc tagatgtatg  5580
tacttcatgc tgtctacact aagagagaat gagagacaca ctgaagaagc accaatcatg  5640
aattagtttt atatgcttct gttttataat tttgtgaagc aaaattttt  ctctaggaaa  5700 tatttatttt aataatgttt caaacatata ttacaatgct gtattttaaa agaatgatta  5760
tgaattacat ttgtataaaa aattttttat atttgaaata ttgactttt  atggcactag  5820 tatttttatg aaatattatg ttaaaactgg gacaggggag aacctagggt gatattaacc  5880
aggggccatg aatcaccttt tggtctggag ggaagccttg gggctgatcg agttgttgcc  5940
cacagctgta tgattcccag ccagacacag cctcttagat gcagttctga agaagatggt  6000
accaccagtc tgactgtttc catcaagggt acactgcctt ctcaactcca aactgactct  6060
taagaagact gcattatatt tattactgta agaaaatatc acttgtcaat aaaatccata  6120
catttgtgt                                                          6129
```

<210> SEQ ID NO 2
<211> LENGTH: 1480
<212> TYPE: PRT
<213> ORGANISM: Homo sapiens

<400> SEQUENCE: 2

```
Met Gln Arg Ser Pro Leu Glu Lys Ala Ser Val Val Ser Lys Leu Phe
  1               5                  10                  15

Phe Ser Trp Thr Arg Pro Ile Leu Arg Lys Gly Tyr Arg Gln Arg Leu
             20                  25                  30

Glu Leu Ser Asp Ile Tyr Gln Ile Pro Ser Val Asp Ser Ala Asp Asn
         35                  40                  45

Leu Ser Glu Lys Leu Glu Arg Glu Trp Asp Arg Glu Leu Ala Ser Lys
     50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220
```

-continued

```
Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
            245                 250                 255

Glu Arg Leu Val Ile Thr Ser Glu Met Ile Glu Asn Ile Gln Ser Val
                260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
    290                 295                 300

Phe Asn Ser Ser Ala Phe Phe Ser Gly Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu Asn Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
```

-continued

```
                      645                 650                 655
Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
            675                 680                 685

Gln Thr Gly Glu Phe Gly Glu Lys Arg Lys Asn Ser Ile Leu Asn Pro
            690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
            755                 760                 765

Val Leu Asn Leu Met Thr His Ser Val Asn Gln Gly Gln Asn Ile His
            770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Leu Phe Asp Asp Met Glu Ser Ile Pro Ala Val Thr Thr Trp Asn Thr
            835                 840                 845

Tyr Leu Arg Tyr Ile Thr Val His Lys Ser Leu Ile Phe Val Leu Ile
            850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
                900                 905                 910

Tyr Tyr Val Phe Tyr Ile Tyr Val Gly Val Ala Asp Thr Leu Leu Ala
            915                 920                 925

Met Gly Phe Phe Arg Gly Leu Pro Leu Val His Thr Leu Ile Thr Val
            930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
            995                 1000                1005

Ala Val Leu Gln Pro Tyr Ile Phe Val Ala Thr Val Pro Val Ile Val
    1010                1015                1020

Ala Phe Ile Met Leu Arg Ala Tyr Phe Leu Gln Thr Ser Gln Gln Leu
1025                1030                1035                1040

Lys Gln Leu Glu Ser Glu Gly Arg Ser Pro Ile Phe Thr His Leu Val
                1045                1050                1055

Thr Ser Leu Lys Gly Leu Trp Thr Leu Arg Ala Phe Gly Arg Gln Pro
            1060                1065                1070
```

-continued

```
Tyr Phe Glu Thr Leu Phe His Lys Ala Leu Asn Leu His Thr Ala Asn
            1075                1080                1085

Trp Phe Leu Tyr Leu Ser Thr Leu Arg Trp Phe Gln Met Arg Ile Glu
        1090                1095                1100

Met Ile Phe Val Ile Phe Ile Ala Val Thr Phe Ile Ser Ile Leu
1105                1110                1115                1120

Thr Thr Gly Glu Gly Glu Gly Arg Val Gly Ile Ile Leu Thr Leu Ala
            1125                1130                1135

Met Asn Ile Met Ser Thr Leu Gln Trp Ala Val Asn Ser Ser Ile Asp
                1140                1145                1150

Val Asp Ser Leu Met Arg Ser Val Ser Arg Val Phe Lys Phe Ile Asp
            1155                1160                1165

Met Pro Thr Glu Gly Lys Pro Thr Lys Ser Thr Lys Pro Tyr Lys Asn
        1170                1175                1180

Gly Gln Leu Ser Lys Val Met Ile Ile Glu Asn Ser His Val Lys Lys
1185                1190                1195                1200

Asp Asp Ile Trp Pro Ser Gly Gly Gln Met Thr Val Lys Asp Leu Thr
            1205                1210                1215

Ala Lys Tyr Thr Glu Gly Gly Asn Ala Ile Leu Glu Asn Ile Ser Phe
            1220                1225                1230

Ser Ile Ser Pro Gly Gln Arg Val Gly Leu Leu Gly Arg Thr Gly Ser
            1235                1240                1245

Gly Lys Ser Thr Leu Leu Ser Ala Phe Leu Arg Leu Leu Asn Thr Glu
        1250                1255                1260

Gly Glu Ile Gln Ile Asp Gly Val Ser Trp Asp Ser Ile Thr Leu Gln
1265                1270                1275                1280

Gln Trp Arg Lys Ala Phe Gly Val Ile Pro Gln Lys Val Phe Ile Phe
            1285                1290                1295

Ser Gly Thr Phe Arg Lys Asn Leu Asp Pro Tyr Glu Gln Trp Ser Asp
            1300                1305                1310

Gln Glu Ile Trp Lys Val Ala Asp Glu Val Gly Leu Arg Ser Val Ile
            1315                1320                1325

Glu Gln Phe Pro Gly Lys Leu Asp Phe Val Leu Val Asp Gly Gly Cys
            1330                1335                1340

Val Leu Ser His Gly His Lys Gln Leu Met Cys Leu Ala Arg Ser Val
1345                1350                1355                1360

Leu Ser Lys Ala Lys Ile Leu Leu Leu Asp Glu Pro Ser Ala His Leu
        1365                1370                1375

Asp Pro Val Thr Tyr Gln Ile Ile Arg Arg Thr Leu Lys Gln Ala Phe
            1380                1385                1390

Ala Asp Cys Thr Val Ile Leu Cys Glu His Arg Ile Glu Ala Met Leu
            1395                1400                1405

Glu Cys Gln Gln Phe Leu Val Ile Glu Glu Asn Lys Val Arg Gln Tyr
        1410                1415                1420

Asp Ser Ile Gln Lys Leu Leu Asn Glu Arg Ser Leu Phe Arg Gln Ala
1425                1430                1435                1440

Ile Ser Pro Ser Asp Arg Val Lys Leu Phe Pro His Arg Asn Ser Ser
                1445                1450                1455

Lys Cys Lys Ser Lys Pro Gln Ile Ala Ala Leu Lys Glu Glu Thr Glu
            1460                1465                1470

Glu Glu Val Gln Asp Thr Arg Leu
        1475                1480
```

<210> SEQ ID NO 3
<211> LENGTH: 6126
<212> TYPE: DNA
<213> ORGANISM: Homo sapiens

<400> SEQUENCE: 3

| | | | | | |
|---|---|---|---|---|---|
| aattggaagc | aaatgacatc | acagcaggtc | agagaaaaag | ggttgagcgg | caggcaccca | 60 |
| gagtagtagg | tctttggcat | taggagcttg | agcccagacg | gccctagcag | ggaccccagc | 120 |
| gcccgagaga | ccatgcagag | gtcgcctctg | gaaaaggcca | gcgttgtctc | caaacttttt | 180 |
| ttcagctgga | ccagaccaat | tttgaggaaa | ggatacagac | agcgcctgga | attgtcagac | 240 |
| atataccaaa | tcccttctgt | tgattctgct | gacaatctat | ctgaaaaatt | ggaaagagaa | 300 |
| tgggatagag | agctggcttc | aaagaaaaat | cctaaactca | ttaatgccct | tcggcgatgt | 360 |
| ttttctgga | gatttatgtt | ctatggaatc | tttttatatt | taggggaagt | caccaaagca | 420 |
| gtacagcctc | tcttactggg | aagaatcata | gcttcctatg | acccggataa | caaggaggaa | 480 |
| cgctctatcg | cgatttatct | aggcataggc | ttatgccttc | tctttattgt | gaggacactg | 540 |
| ctcctacacc | cagccatttt | tggccttcat | cacattggaa | tgcagatgag | aatagctatg | 600 |
| tttagtttga | tttataagaa | gactttaaag | ctgtcaagcc | gtgttctaga | taaaataagt | 660 |
| attggacaac | ttgttagtct | cctttccaac | aacctgaaca | aatttgatga | aggacttgca | 720 |
| ttggcacatt | tcgtgtggat | cgctcctttg | caagtggcac | tcctcatggg | gctaatctgg | 780 |
| gagttgttac | aggcgtctgc | cttcgtggga | cttggttttcc | tgatagtcct | tgccctttt | 840 |
| caggctgggc | tagggagaat | gatgatgaag | tacagagatc | agagagctgg | aagatcagt | 900 |
| gaaagacttg | tgattacctc | agaaatgatt | gaaaatatcc | aatctgttaa | ggcatactgc | 960 |
| tgggaagaag | caatggaaaa | aatgattgaa | aacttaagac | aaacagaact | gaaactgact | 1020 |
| cggaaggcag | cctatgtgag | atacttcaat | agctcagcct | tcttcttctc | agggttcttt | 1080 |
| gtggtgtttt | tatctgtgct | tccctatgca | ctaatcaaag | gaatcatcct | ccggaaaata | 1140 |
| ttcaccacca | tctcattctg | cattgttctg | cgcatggcgg | tcactcggca | atttcccctgg | 1200 |
| gctgtacaaa | catggtatga | ctctcttgga | gcaataaaca | aaatacagga | tttcttacaa | 1260 |
| aagcaagaat | ataagacatt | ggaatataac | ttaacgacta | cagaagtagt | gatggagaat | 1320 |
| gtaacagcct | tctgggagga | gggatttggg | gaattatttg | agaaagcaaa | acaaaacaat | 1380 |
| aacaatagaa | aaacttctaa | tggtgatgac | agcctcttct | tcagtaattt | ctcacttctt | 1440 |
| ggtactcctg | tcctgaaaga | tattaatttc | aagatagaaa | gaggacagtt | gttggcggtt | 1500 |
| gctggatcca | ctggagcagg | caagacttca | cttctaatga | tgattatggg | agaactggag | 1560 |
| ccttcagagg | gtaaaattaa | gcacagtgga | agaatttcat | tctgttctca | gttttcctgg | 1620 |
| attatgcctg | gcaccattaa | agaaaatatc | atcggtgttt | cctatgatga | atatagatac | 1680 |
| agaagcgtca | tcaaagcatg | ccaactagaa | gaggacatct | ccaagtttgc | agagaaagac | 1740 |
| aatatagttc | ttggagaagg | tggaatcaca | ctgagtggag | gtcaacgagc | aagaatttct | 1800 |
| ttagcaagag | cagtatacaa | agatgctgat | ttgtatttat | tagactctcc | ttttggatac | 1860 |
| ctagatgttt | taacagaaaa | agaaatattt | gaaagctgtg | tctgtaaact | gatggctaac | 1920 |
| aaaactagga | ttttggtcac | ttctaaaatg | gaacatttaa | agaaagctga | caaaatatta | 1980 |
| attttgaatg | aaggtagcag | ctattttat | gggacatttt | cagaactcca | aaatctacag | 2040 |
| ccagacttta | gctcaaaact | catgggatgt | gattctttcg | accaatttag | tgcagaaaga | 2100 |
| agaaattcaa | tcctaactga | gaccttacac | cgtttctcat | tagaaggaga | tgctcctgtc | 2160 |

```
tcctggacag aaacaaaaaa acaatctttt aaacagactg gagagtttgg ggaaaaaagg    2220
aagaattcta ttctcaatcc aatcaactct atacgaaaat tttccattgt gcaaaagact    2280
cccttacaaa tgaatggcat cgaagaggat tctgatgagc ctttagagag aaggctgtcc    2340
ttagtaccag attctgagca gggagaggcg atactgcctc gcatcagcgt gatcagcact    2400
ggccccacgc ttcaggcacg aaggaggcag tctgtcctga acctgatgac acactcagtt    2460
aaccaaggtc agaacattca ccgaaagaca acagcatcca cacgaaaagt gtcactggcc    2520
cctcaggcaa acttgactga actggatata tattcaagaa ggttatctca agaaactggc    2580
ttggaaataa gtgaagaaat taacgaagaa gacttaaagg agtgcctttt tgatgatatg    2640
gagagcatac cagcagtgac tacatggaac acataccttc gatatattac tgtccacaag    2700
agcttaattt ttgtgctaat ttggtgctta gtaattttc tggcagaggt ggctgcttct    2760
ttggttgtgc tgtggctcct tggaaacact cctcttcaag acaaagggaa tagtactcat    2820
agtagaaata acagctatgc agtgattatc accagcacca gttcgtatta tgtgttttac    2880
atttacgtgg gagtagccga cactttgctt gctatgggat tcttcagagg tctaccactg    2940
gtgcatactc taatcacagt gtcgaaaatt ttacaccaca aaatgttaca ttctgttctt    3000
caagcaccta tgtcaaccct caacacgttg aaagcaggtg ggattcttaa tagattctcc    3060
aaagatatag caattttgga tgaccttctg cctcttacca tatttgactt catccagttg    3120
ttattaattg tgattggagc tatagcagtt gtcgcagttt tacaacccta catctttgtt    3180
gcaacagtgc cagtgatagt ggcttttatt atgttgagag catatttcct ccaaacctca    3240
cagcaactca aacaactgga atctgaaggc aggagtccaa ttttcactca tcttgttaca    3300
agcttaaaag gactatggac acttcgtgcc ttcggacggc agccttactt tgaaactctg    3360
ttccacaaag ctctgaattt acatactgcc aactggttct tgtacctgtc aacactgcgc    3420
tggttccaaa tgagaataga aatgattttt gtcatcttct tcattgctgt taccttcatt    3480
tccattttaa caacaggaga aggagaagga agagttggta ttatcctgac tttagccatg    3540
aatatcatga gtacattgca gtgggctgta aactccagca tagatgtgga tagcttgatg    3600
cgatctgtga gccgagtctt taagttcatt gacatgccaa cagaaggtaa acctaccaag    3660
tcaaccaaac catacaagaa tggccaactc tcgaaagtta tgattattga gaattcacac    3720
gtgaagaaag atgacatctg gcccccaggg gccaaatga ctgtcaaaga tctcacagca    3780
aaatacacag aaggtggaaa tgccatatta gagaacattt ccttctcaat aagtcctggc    3840
cagagggtgg gcctcttggg aagaactgga tcagggaaga gtactttgtt atcagctttt    3900
ttgagactac tgaacactga aggagaaatc cagatcgatg gtgtgtcttg ggattcaata    3960
actttgcaac agtggaggaa agcctttgga gtgataccac agaaagtatt tatttttct    4020 ggaacattta gaaaaaactt ggatcctat gaacagtgga gtgatcaaga aatatggaaa    4080
gttgcagatg aggttgggct cagatctgtg atagaacagt ttcctgggaa gcttgacttt    4140
gtccttgtgg atgggggctg tgtcctaagc catggccaca gcagttgat gtgcttggct    4200 agatctgttc tcagtaaggc gaagatcttg ctgcttgatg aacccagtgc tcatttggat    4260
ccagtaacat accaaataat tagaagaact ctaaaacaag catttgctga ttgcacagta    4320
attctctgtg aacacaggat agaagcaatg ctggaatgcc aacaatttt ggtcatagaa    4380 gagaacaaag tgcggcagta cgattccatc cagaaactgc tgaacgagag gagcctcttc    4440
cggcaagcca tcagcccctc cgacagggtg aagctctttc cccaccggaa ctcaagcaag    4500
```

-continued

```
tgcaagtcta agccccagat tgctgctctg aaagaggaga cagaagaaga ggtgcaagat    4560
acaaggcttt agagagcagc ataaatgttg acatgggaca tttgctcatg gaattggagc    4620
tcgtgggaca gtcacctcat ggaattggag ctcgtggaac agttacctct gcctcagaaa    4680
acaaggatga attaagtttt tttttaaaaa agaaacattt ggtaagggga attgaggaca    4740
ctgatatggg tcttgataaa tggcttcctg gcaatagtca aattgtgtga aaggtacttc    4800
aaatccttga agatttacca cttgtgtttt gcaagccaga ttttcctgaa aacccttgcc    4860
atgtgctagt aattggaaag gcagctctaa atgtcaatca gcctagttga tcagcttatt    4920
gtctagtgaa actcgttaat ttgtagtgtt ggagaagaac tgaaatcata cttcttaggg    4980
ttatgattaa gtaatgataa ctggaaactt cagcggttta tataagcttg tattcctttt    5040
tctctcctct ccccatgatg tttagaaaca caactatatt gtttgctaag cattccaact    5100
atctcatttc caagcaagta ttagaatacc acaggaacca caagactgca catcaaaata    5160
tgccccattc aacatctagt gagcagtcag gaaagagaac ttccagatcc tggaaatcag    5220
ggttagtatt gtccaggtct accaaaaatc tcaatatttc agataatcac aatacatccc    5280
ttacctggga aagggctgtt ataatctttc acaggggaca ggatggttcc cttgatgaag    5340
aagttgatat gccttttccc aactccagaa agtgacaagc tcacagacct tgaactaga    5400 gtttagctgg aaaagtatgt tagtgcaaat tgtcacagga cagcccttct ttccacagaa    5460
gctccaggta gagggtgtgt aagtagatag gccatgggca ctgtgggtag acacacatga    5520
agtccaagca tttagatgta taggttgatg gtggtatgtt ttcaggctag atgtatgtac    5580
ttcatgctgt ctacactaag agagaatgag agacacactg aagaagcacc aatcatgaat    5640
tagttttata tgcttctgtt ttataatttt gtgaagcaaa attttttctc taggaaatat    5700
ttattttaat aatgtttcaa acatatatta caatgctgta ttttaaaaga atgattatga    5760
attacatttg tataaaataa ttttttatatt tgaaatattg acttttatg gcactagtat    5820 ttttatgaaa tattatgtta aaactgggac aggggagaac ctagggtgat attaaccagg    5880
ggccatgaat caccttttgg tctggaggga agccttgggg ctgatcgagt tgttgcccac    5940
agctgtatga ttcccagcca gacacagcct cttagatgca gttctgaaga agtggtacc    6000 accagtctga ctgtttccat caagggtaca ctgccttctc aactccaaac tgactcttaa    6060
gaagactgca ttatatttat tactgtaaga aaatatcact tgtcaataaa atccatacat    6120
ttgtgt                                                                 6126
```

<210> SEQ ID NO 4
<211> LENGTH: 1479
<212> TYPE: PRT
<213> ORGANISM: Homo sapiens

<400> SEQUENCE: 4

```
Met Gln Arg Ser Pro Leu Glu Lys Ala Ser Val Val Ser Lys Leu Phe
  1               5                  10                  15

Phe Ser Trp Thr Arg Pro Ile Leu Arg Lys Gly Tyr Arg Gln Arg Leu
             20                  25                  30

Glu Leu Ser Asp Ile Tyr Gln Ile Pro Ser Val Asp Ser Ala Asp Asn
         35                  40                  45

Leu Ser Glu Lys Leu Glu Arg Glu Trp Asp Arg Glu Leu Ala Ser Lys
     50                  55                  60

Lys Asn Pro Lys Leu Ile Asn Ala Leu Arg Arg Cys Phe Phe Trp Arg
 65                  70                  75                  80
```

```
Phe Met Phe Tyr Gly Ile Phe Leu Tyr Leu Gly Val Thr Lys Ala
                 85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
        130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Gly Val Ser Tyr Asp
```

-continued

```
                500                 505                 510
Glu Tyr Arg Tyr Arg Ser Val Ile Lys Ala Cys Gln Leu Glu Glu Asp
            515                 520                 525

Ile Ser Lys Phe Ala Glu Lys Asp Asn Ile Val Leu Gly Glu Gly Gly
        530                 535                 540

Ile Thr Leu Ser Gly Gly Gln Arg Ala Arg Ile Ser Leu Ala Arg Ala
545                 550                 555                 560

Val Tyr Lys Asp Ala Asp Leu Tyr Leu Leu Asp Ser Pro Phe Gly Tyr
            565                 570                 575

Leu Asp Val Leu Thr Glu Lys Glu Ile Phe Glu Ser Cys Val Cys Lys
        580                 585                 590

Leu Met Ala Asn Lys Thr Arg Ile Leu Val Thr Ser Lys Met Glu His
            595                 600                 605

Leu Lys Lys Ala Asp Lys Ile Leu Ile Leu Asn Glu Gly Ser Ser Tyr
        610                 615                 620

Phe Tyr Gly Thr Phe Ser Glu Leu Gln Asn Leu Gln Pro Asp Phe Ser
625                 630                 635                 640

Ser Lys Leu Met Gly Cys Asp Ser Phe Asp Gln Phe Ser Ala Glu Arg
            645                 650                 655

Arg Asn Ser Ile Leu Thr Glu Thr Leu His Arg Phe Ser Leu Glu Gly
        660                 665                 670

Asp Ala Pro Val Ser Trp Thr Glu Thr Lys Lys Gln Ser Phe Lys Gln
            675                 680                 685

Thr Gly Glu Phe Gly Glu Lys Arg Lys Asn Ser Ile Leu Asn Pro Ile
        690                 695                 700

Asn Ser Ile Arg Lys Phe Ser Ile Val Gln Lys Thr Pro Leu Gln Met
705                 710                 715                 720

Asn Gly Ile Glu Glu Asp Ser Asp Glu Pro Leu Glu Arg Arg Leu Ser
            725                 730                 735

Leu Val Pro Asp Ser Glu Gln Gly Glu Ala Ile Leu Pro Arg Ile Ser
        740                 745                 750

Val Ile Ser Thr Gly Pro Thr Leu Gln Ala Arg Arg Arg Gln Ser Val
            755                 760                 765

Leu Asn Leu Met Thr His Ser Val Asn Gln Gly Gln Asn Ile His Arg
        770                 775                 780

Lys Thr Thr Ala Ser Thr Arg Lys Val Ser Leu Ala Pro Gln Ala Asn
785                 790                 795                 800

Leu Thr Glu Leu Asp Ile Tyr Ser Arg Arg Leu Ser Gln Glu Thr Gly
            805                 810                 815

Leu Glu Ile Ser Glu Glu Ile Asn Glu Glu Asp Leu Lys Glu Cys Leu
        820                 825                 830

Phe Asp Asp Met Glu Ser Ile Pro Ala Val Thr Thr Trp Asn Thr Tyr
            835                 840                 845

Leu Arg Tyr Ile Thr Val His Lys Ser Leu Ile Phe Val Leu Ile Trp
        850                 855                 860

Cys Leu Val Ile Phe Leu Ala Glu Val Ala Ala Ser Leu Val Val Leu
865                 870                 875                 880

Trp Leu Leu Gly Asn Thr Pro Leu Gln Asp Lys Gly Asn Ser Thr His
            885                 890                 895

Ser Arg Asn Asn Ser Tyr Ala Val Ile Ile Thr Ser Thr Ser Ser Tyr
        900                 905                 910

Tyr Val Phe Tyr Ile Tyr Val Gly Val Ala Asp Thr Leu Leu Ala Met
            915                 920                 925
```

```
Gly Phe Phe Arg Gly Leu Pro Leu Val His Thr Leu Ile Thr Val Ser
    930                 935                 940

Lys Ile Leu His His Lys Met Leu His Ser Val Leu Gln Ala Pro Met
945                 950                 955                 960

Ser Thr Leu Asn Thr Leu Lys Ala Gly Gly Ile Leu Asn Arg Phe Ser
                965                 970                 975

Lys Asp Ile Ala Ile Leu Asp Asp Leu Leu Pro Leu Thr Ile Phe Asp
            980                 985                 990

Phe Ile Gln Leu Leu Leu Ile Val Ile Gly Ala Ile Ala Val Val Ala
        995                 1000                1005

Val Leu Gln Pro Tyr Ile Phe Val Ala Thr Val Pro Val Ile Val Ala
    1010                1015                1020

Phe Ile Met Leu Arg Ala Tyr Phe Leu Gln Thr Ser Gln Gln Leu Lys
1025                1030                1035                1040

Gln Leu Glu Ser Glu Gly Arg Ser Pro Ile Phe Thr His Leu Val Thr
                1045                1050                1055

Ser Leu Lys Gly Leu Trp Thr Leu Arg Ala Phe Gly Arg Gln Pro Tyr
            1060                1065                1070

Phe Glu Thr Leu Phe His Lys Ala Leu Asn Leu His Thr Ala Asn Trp
        1075                1080                1085

Phe Leu Tyr Leu Ser Thr Leu Arg Trp Phe Gln Met Arg Ile Glu Met
    1090                1095                1100

Ile Phe Val Ile Phe Phe Ile Ala Val Thr Phe Ile Ser Ile Leu Thr
1105                1110                1115                1120

Thr Gly Glu Gly Glu Gly Arg Val Gly Ile Ile Leu Thr Leu Ala Met
                1125                1130                1135

Asn Ile Met Ser Thr Leu Gln Trp Ala Val Asn Ser Ser Ile Asp Val
            1140                1145                1150

Asp Ser Leu Met Arg Ser Val Ser Arg Val Phe Lys Phe Ile Asp Met
        1155                1160                1165

Pro Thr Glu Gly Lys Pro Thr Lys Ser Thr Lys Pro Tyr Lys Asn Gly
    1170                1175                1180

Gln Leu Ser Lys Val Met Ile Ile Glu Asn Ser His Val Lys Lys Asp
1185                1190                1195                1200

Asp Ile Trp Pro Ser Gly Gly Gln Met Thr Val Lys Asp Leu Thr Ala
                1205                1210                1215

Lys Tyr Thr Glu Gly Gly Asn Ala Ile Leu Glu Asn Ile Ser Phe Ser
            1220                1225                1230

Ile Ser Pro Gly Gln Arg Val Gly Leu Leu Gly Arg Thr Gly Ser Gly
        1235                1240                1245

Lys Ser Thr Leu Leu Ser Ala Phe Leu Arg Leu Leu Asn Thr Glu Gly
    1250                1255                1260

Glu Ile Gln Ile Asp Gly Val Ser Trp Asp Ser Ile Thr Leu Gln Gln
1265                1270                1275                1280

Trp Arg Lys Ala Phe Gly Val Ile Pro Gln Lys Val Phe Ile Phe Ser
                1285                1290                1295

Gly Thr Phe Arg Lys Asn Leu Asp Pro Tyr Glu Gln Trp Ser Asp Gln
            1300                1305                1310

Glu Ile Trp Lys Val Ala Asp Glu Val Gly Leu Arg Ser Val Ile Glu
        1315                1320                1325

Gln Phe Pro Gly Lys Leu Asp Phe Val Leu Val Asp Gly Gly Cys Val
    1330                1335                1340
```

```
Leu Ser His Gly His Lys Gln Leu Met Cys Leu Ala Arg Ser Val Leu
1345                1350                1355                1360

Ser Lys Ala Lys Ile Leu Leu Asp Glu Pro Ser Ala His Leu Asp
            1365                1370                1375

Pro Val Thr Tyr Gln Ile Ile Arg Arg Thr Leu Lys Gln Ala Phe Ala
        1380                1385                1390

Asp Cys Thr Val Ile Leu Cys Glu His Arg Ile Glu Ala Met Leu Glu
        1395                1400                1405

Cys Gln Gln Phe Leu Val Ile Glu Glu Asn Lys Val Arg Gln Tyr Asp
    1410                1415                1420

Ser Ile Gln Lys Leu Leu Asn Glu Arg Ser Leu Phe Arg Gln Ala Ile
1425                1430                1435                1440

Ser Pro Ser Asp Arg Val Lys Leu Phe Pro His Arg Asn Ser Ser Lys
            1445                1450                1455

Cys Lys Ser Lys Pro Gln Ile Ala Ala Leu Lys Glu Glu Thr Glu Glu
            1460                1465                1470

Glu Val Gln Asp Thr Arg Leu
        1475

<210> SEQ ID NO 5
<211> LENGTH: 6129
<212> TYPE: DNA
<213> ORGANISM: Homo sapiens

<400> SEQUENCE: 5
aattggaagc aaatgacatc acagcaggtc agagaaaaag ggttgagcgg caggcaccca      60
gagtagtagg tctttggcat taggagcttg agcccagacg ccctagcag ggaccccagc      120 gcccgagaga ccatgcagag gtcgcctctg gaaaaggcca gcgttgtctc caaacttttt     180
ttcagctgga ccagaccaat tttgaggaaa ggatacagac agcgcctgga attgtcagac    240
atataccaaa tcccttctgt tgattctgct gacaatctat ctgaaaaatt ggaaagagaa     300
tgggatagag agctggcttc aaagaaaaat cctaaactca ttaatgccct tcggcgatgt    360 ttttctctgga gatttatgtt ctatggaatc tttttatatt taggggaagt caccaaagca   420
gtacagcctc tcttactggg aagaatcata gcttcctatg acccggataa caaggaggaa    480
cgctctatcg cgatttatct aggcataggc ttatgccttc tctttattgt gaggacactg   540
ctcctacacc cagccatttt tggccttcat cacattggaa tgcagatgag aatagctatg     600
tttagtttga tttataagaa gactttaaag ctgtcaagcc gtgttctaga taaaataagt    660
attggacaac ttgttagtct ccttttccaac aacctgaaca aatttgatga aggacttgca   720
ttggcacatt tcgtgtggat cgctcctttg caagtggcac tcctcatggg gctaatctgg    780
gagttgttac aggcgtctgc cttctgtgga cttggtttcc tgatagtcct tgcccttttt    840
caggctgggc tagggagaat gatgatgaag tacagagatc agagagctgg gaagatcagt    900
gaaagacttg tgattacctc agaaatgatt gaaaatatcc aatctgttaa ggcatactgc    960
tgggaagaag caatggaaaa aatgattgaa aacttaagac aaacagaact gaaactgact   1020
cggaaggcag cctatgtgag atacttcaat agctcagcct tcttcttctc agggttcttt   1080
gtggtgtttt tatctgtgct tcccttatgca ctaatcaaag gaatcatcct ccggaaaata   1140
ttcaccacca tctcattctg cattgttctg cgcatggcgg tcactcggca atttcctgg   1200 gctgtacaaa catggtatga ctctcttgga gcaataaaca aaatacagga tttcttacaa    1260
aagcaagaat ataagacatt ggaatataac ttaacgacta cagaagtagt gatggagaat   1320
```

```
gtaacagcct tctgggagga gggatttggg gaattatttg agaaagcaaa acaaaacaat    1380
aacaatagaa aaacttctaa tggtgatgac agcctcttct tcagtaattt ctcacttctt    1440
ggtactcctg tcctgaaaga tattaatttc aagatagaaa gaggacagtt gttggcggtt    1500
gctggatcca ctggagcagg caagacttca cttctaatga tgattatggg agaactggag    1560
ccttcagagg gtaaaattaa gcacagtgga agaatttcat tctgttctca gttttcctgg    1620
attatgcctg gcaccattaa agaaaatatc atctttggtg tttcctatga tgaatataga    1680
tacagaagcg tcatcaaagc atgccaacta aagaggaca tctccaagtt tgcagagaaa    1740
gacaatatag ttcttggaga aggtggaatc acactgagtg gagaycaacg agcaagaatt    1800
tctttagcaa gagcagtata caaagatgct gatttgtatt tattagactc tccttttgga    1860
tacctagatg ttttaacaga aaagaaata tttgaaagct gtgtctgtaa actgatggct    1920
aacaaaacta ggattttggt cacttctaaa atggaacatt taaagaaagc tgacaaaata    1980
ttaattttga atgaaggtag cagctatttt tatgggacat tttcagaact ccaaaatcta    2040
cagccagact ttagctcaaa actcatggga tgtgattctt tcgaccaatt tagtgcagaa    2100
agaagaaatt caatcctaac tgagaccta caccgtttct cattagaagg atgctcct    2160 gtctcctgga cagaaacaaa aaaacaatct tttaaacaga ctggagagtt tggggaaaaa    2220
aggaagaatt ctattctcaa tccaatcaac tctatacgaa aattttccat tgtgcaaaag    2280
actcccttac aaatgaatgg catcgaagag gattctgatg agcctttaga gagaaggctg    2340
tccttagtac cagattctga gcagggagag gcgatactgc ctcgcatcag cgtgatcagc    2400
actggcccca cgcttcaggc acgaaggagg cagtctgtcc tgaacctgat gacacactca    2460
gttaaccaag gtcagaacat tcaccgaaag acaacagcat ccacacgaaa agtgtcactg    2520
gcccctcagg caaacttgac tgaactggat atatattcaa gaaggttatc tcaagaaact    2580
ggcttggaaa taagtgaaga aattaacgaa gaagacttaa aggagtgcct ttttgatgat    2640
atggagagca taccagcagt gactacatgg aacacatacc ttcgatatat tactgtccac    2700
aagagcttaa ttttgtgct aatttggtgc ttagtaattt ttctggcaga ggtggctgct    2760
tctttggttg tgctgtggct ccttggaaac actcctcttc aagacaaagg gaatagtact    2820
catagtagaa ataacagcta tgcagtgatt atcaccagca ccagttcgta ttatgtgttt    2880
tacatttacg tgggagtagc cgacactttg cttgctatgg gattcttcag aggtctacca    2940
ctggtgcata ctctaatcac agtgtcgaaa attttacacc acaaaatgtt acattctgtt    3000
cttcaagcac ctatgtcaac cctcaacacg ttgaaagcag gtgggattct taatagattc    3060
tccaaagata tagcaatttt ggatgacctt ctgcctctta ccatatttga cttcatccag    3120
ttgttattaa ttgtgattgg agctatagca gttgtcgcag ttttacaacc ctacatcttt    3180
gttgcaacag tgccagtgat agtggctttt attatgttga gagcatattt cctccaaacc    3240
tcacagcaac tcaaacaact ggaatctgaa ggcaggagtc caattttcac tcatcttgtt    3300
acaagcttaa aaggactatg gacacttcgt gccttcggac ggcagcctta ctttgaaact    3360
ctgttccaca aagctctgaa tttacatact gccaactggt tcttgtacct gtcaacactg    3420
cgctggttcc aaatgagaat agaaatgatt tttgtcatct tcttcattgc tgttaccttc    3480
atttccattt taacaacagg agaaggagaa ggaagagttg tattatcct gacttttagcc    3540 atgaatatca tgagtacatt gcagtgggct gtaaactcca gcatagatgt ggatagcttg    3600
atgcgatctg tgagccgagt ctttaagttc attgacatgc caacagaagg taaacctacc    3660
aagtcaacca aaccatacaa gaatggccaa ctctcgaaag ttatgattat tgagaattca    3720
```

```
cacgtgaaga aagatgacat ctggccctca gggggccaaa tgactgtcaa agatctcaca    3780
gcaaaataca cagaaggtgg aaatgccata ttagagaaca tttccttctc aataagtcct    3840
ggccagaggg tgggcctctt ggaagaact ggatcaggga agagtacttt gttatcagct     3900
tttttgagac tactgaacac tgaaggagaa atccagatcg atggtgtgtc ttgggattca    3960
ataactttgc aacagtggag gaaagccttt ggagtgatac cacagaaagt atttattttt    4020
tctggaacat ttagaaaaaa cttggatccc tatgaacagt ggagtgatca agaaatatgg    4080
aaagttgcag atgaggttgg gctcagatct gtgatagaac agtttcctgg gaagcttgac    4140
tttgtccttg tggatggggg ctgtgtccta agccatggcc acaagcagtt gatgtgcttg    4200
gctagatctg ttctcagtaa ggcgaagatc ttgctgcttg atgaacccag tgctcatttg    4260
gatccagtaa cataccaaat aattagaaga actctaaaac aagcatttgc tgattgcaca    4320
gtaattctct gtgaacacag gatagaagca atgctggaat gccaacaatt tttggtcata    4380
gaagagaaca aagtgcggca gtacgattcc atccagaaac tgctgaacga gaggagcctc    4440
ttccggcaag ccatcagccc ctccgacagg gtgaagctct tccccaccg gaactcaagc    4500 aagtgcaagt ctaagcccca gattgctgct ctgaaagagg agacagaaga agaggtgcaa    4560
gatacaaggc tttagagagc agcataaatg ttgacatggg acatttgctc atggaattgg    4620
agctcgtggg acagtcacct catggaattg gagctcgtgg aacagttacc tctgcctcag    4680
aaaacaagga tgaattaagt ttttttttaa aaagaaaca tttggtaagg ggaattgagg     4740
acactgatat gggtcttgat aaatggcttc ctggcaatag tcaaattgtg tgaaaggtac    4800
ttcaaatcct tgaagattta ccacttgtgt tttgcaagcc agattttcct gaaaacccctt   4860 gccatgtgct agtaattgga aaggcagctc taaatgtcaa tcagcctagt tgatcagctt    4920
attgtctagt gaaactcgtt aatttgtagt gttggagaag aactgaaatc atacttctta    4980
gggttatgat taagtaatga taactggaaa cttcagcgt ttatataagc ttgtattcct     5040
ttttctctcc tctccccatg atgtttagaa acacaactat attgtttgct aagcattcca    5100
actatctcat ttccaagcaa gtattagaat accacaggaa ccacaagact gcacatcaaa    5160
atatgcccca ttcaacatct agtgagcagt caggaaagag aacttccaga tcctggaaat    5220
cagggttagt attgtccagg tctaccaaaa atctcaatat ttcagataat cacaatacat    5280
cccttacctg ggaaagggct gttataatct ttcacagggg acaggatggt tcccttgatg    5340
aagaagttga tatgcctttt cccaactcca gaaagtgaca agctcacaga cctttgaact    5400
agagtttagc tggaaaagta tgttagtgca aattgtcaca ggacagccct tctttccaca    5460
gaagctccag gtagagggtg tgtaagtaga taggccatgg gcactgtggg tagacacaca    5520
tgaagtccaa gcatttagat gtataggttg atggtggtat gttttcaggc tagatgtatg    5580
tacttcatgc tgtctacact aagagagaat gagagacaca ctgaagaagc accaatcatg    5640
aattagtttt atatgcttct gttttataat tttgtgaagc aaaatttttt ctctaggaaa    5700
tatttatttt aataatgttt caaacatata ttacaatgct gtattttaaa agaatgatta    5760
tgaattacat ttgtataaaa aattttttat atttgaaata ttgactttt atggcactag     5820 tattttatg aaatattatg ttaaaactgg gacaggggag aacctagggt gatattaacc      5880
aggggccatg aatcaccttt tggtctggag ggaagccttg gggctgatcg agttgttgcc    5940
cacagctgta tgattcccag ccagacacag cctcttagat gcagttctga agaagatggt    6000
accaccagtc tgactgtttc catcaagggt acactgcctt ctcaactcca aactgactct    6060
```

```
taagaagact gcattatatt tattactgta agaaaatatc acttgtcaat aaaatccata    6120
catttgtgt                                                            6129
```

<210> SEQ ID NO 6
<211> LENGTH: 1480
<212> TYPE: PRT
<213> ORGANISM: Homo sapiens

<400> SEQUENCE: 6

```
Met Gln Arg Ser Pro Leu Glu Lys Ala Ser Val Val Ser Lys Leu Phe
 1               5                  10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
        50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
```

-continued

```
                355                 360                 365
Asn Lys Ile Gln Asp Phe Leu Gln Lys Gln Glu Tyr Lys Thr Leu Glu
370                 375                 380
Tyr Asn Leu Thr Thr Thr Glu Val Val Met Glu Asn Val Thr Ala Phe
385                 390                 395                 400
Trp Glu Glu Gly Phe Gly Glu Leu Phe Glu Lys Ala Lys Gln Asn Asn
                405                 410                 415
Asn Asn Arg Lys Thr Ser Asn Gly Asp Asp Ser Leu Phe Phe Ser Asn
                420                 425                 430
Phe Ser Leu Leu Gly Thr Pro Val Leu Lys Asp Ile Asn Phe Lys Ile
            435                 440                 445
Glu Arg Gly Gln Leu Leu Ala Val Ala Gly Ser Thr Gly Ala Gly Lys
450                 455                 460
Thr Ser Leu Leu Met Met Ile Met Gly Glu Leu Glu Pro Ser Glu Gly
465                 470                 475                 480
Lys Ile Lys His Ser Gly Arg Ile Ser Phe Cys Ser Gln Phe Ser Trp
                485                 490                 495
Ile Met Pro Gly Thr Ile Lys Glu Asn Ile Ile Phe Gly Val Ser Tyr
                500                 505                 510
Asp Glu Tyr Arg Tyr Arg Ser Val Ile Lys Ala Cys Gln Leu Glu Glu
            515                 520                 525
Asp Ile Ser Lys Phe Ala Glu Lys Asp Asn Ile Val Leu Gly Glu Gly
            530                 535                 540
Gly Ile Thr Leu Ser Gly Asp Gln Arg Ala Arg Ile Ser Leu Ala Arg
545                 550                 555                 560
Ala Val Tyr Lys Asp Ala Asp Leu Tyr Leu Leu Asp Ser Pro Phe Gly
                565                 570                 575
Tyr Leu Asp Val Leu Thr Glu Lys Glu Ile Phe Glu Ser Cys Val Cys
                580                 585                 590
Lys Leu Met Ala Asn Lys Thr Arg Ile Leu Val Thr Ser Lys Met Glu
            595                 600                 605
His Leu Lys Lys Ala Asp Lys Ile Leu Ile Leu Asn Glu Gly Ser Ser
            610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
                645                 650                 655
Arg Arg Asn Ser Ile Leu Thr Glu Thr Leu His Arg Phe Ser Leu Glu
                660                 665                 670
Gly Asp Ala Pro Val Ser Trp Thr Glu Thr Lys Lys Gln Ser Phe Lys
            675                 680                 685
Gln Thr Gly Glu Phe Gly Glu Lys Arg Lys Asn Ser Ile Leu Asn Pro
            690                 695                 700
Ile Asn Ser Ile Arg Lys Phe Ser Ile Val Gln Lys Thr Pro Leu Gln
705                 710                 715                 720
Met Asn Gly Ile Glu Glu Asp Ser Asp Glu Pro Leu Glu Arg Arg Leu
                725                 730                 735
Ser Leu Val Pro Asp Ser Glu Gln Gly Glu Ala Ile Leu Pro Arg Ile
            740                 745                 750
Ser Val Ile Ser Thr Gly Pro Thr Leu Gln Ala Arg Arg Arg Gln Ser
            755                 760                 765
Val Leu Asn Leu Met Thr His Ser Val Asn Gln Gly Gln Asn Ile His
770                 775                 780
```

```
Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
            805                 810                 815

Gly Leu Glu Ile Ser Glu Glu Ile Asn Glu Glu Asp Leu Lys Glu Cys
            820                 825                 830

Leu Phe Asp Asp Met Glu Ser Ile Pro Ala Val Thr Thr Trp Asn Thr
            835                 840                 845

Tyr Leu Arg Tyr Ile Thr Val His Lys Ser Leu Ile Phe Val Leu Ile
850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
            885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
            915                 920                 925

Met Gly Phe Phe Arg Gly Leu Pro Leu Val His Thr Leu Ile Thr Val
            930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
            965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
            995                 1000                1005

Ala Val Leu Gln Pro Tyr Ile Phe Val Ala Thr Val Pro Val Ile Val
    1010                1015                1020

Ala Phe Ile Met Leu Arg Ala Tyr Phe Leu Gln Thr Ser Gln Gln Leu
1025                1030                1035                1040

Lys Gln Leu Glu Ser Glu Gly Arg Ser Pro Ile Phe Thr His Leu Val
            1045                1050                1055

Thr Ser Leu Lys Gly Leu Trp Thr Leu Arg Ala Phe Gly Arg Gln Pro
            1060                1065                1070

Tyr Phe Glu Thr Leu Phe His Lys Ala Leu Asn Leu His Thr Ala Asn
    1075                1080                1085

Trp Phe Leu Tyr Leu Ser Thr Leu Arg Trp Phe Gln Met Arg Ile Glu
    1090                1095                1100

Met Ile Phe Val Ile Phe Phe Ile Ala Val Thr Phe Ile Ser Ile Leu
1105                1110                1115                1120

Thr Thr Gly Glu Gly Glu Gly Arg Val Gly Ile Ile Leu Thr Leu Ala
            1125                1130                1135

Met Asn Ile Met Ser Thr Leu Gln Trp Ala Val Asn Ser Ser Ile Asp
            1140                1145                1150

Val Asp Ser Leu Met Arg Ser Val Ser Arg Val Phe Lys Phe Ile Asp
    1155                1160                1165

Met Pro Thr Glu Gly Lys Pro Thr Lys Ser Thr Lys Pro Tyr Lys Asn
    1170                1175                1180

Gly Gln Leu Ser Lys Val Met Ile Ile Glu Asn Ser His Val Lys Lys
1185                1190                1195                1200
```

```
Asp Asp Ile Trp Pro Ser Gly Gly Gln Met Thr Val Lys Asp Leu Thr
            1205                1210                1215
Ala Lys Tyr Thr Glu Gly Gly Asn Ala Ile Leu Glu Asn Ile Ser Phe
            1220                1225                1230
Ser Ile Ser Pro Gly Gln Arg Val Gly Leu Leu Gly Arg Thr Gly Ser
            1235                1240                1245
Gly Lys Ser Thr Leu Leu Ser Ala Phe Leu Arg Leu Leu Asn Thr Glu
    1250                1255                1260
Gly Glu Ile Gln Ile Asp Gly Val Ser Trp Asp Ser Ile Thr Leu Gln
    1265                1270                1275                1280
Gln Trp Arg Lys Ala Phe Gly Val Ile Pro Gln Lys Val Phe Ile Phe
            1285                1290                1295
Ser Gly Thr Phe Arg Lys Asn Leu Asp Pro Tyr Glu Gln Trp Ser Asp
            1300                1305                1310
Gln Glu Ile Trp Lys Val Ala Asp Glu Val Gly Leu Arg Ser Val Ile
            1315                1320                1325
Glu Gln Phe Pro Gly Lys Leu Asp Phe Val Leu Val Asp Gly Gly Cys
            1330                1335                1340
Val Leu Ser His Gly His Lys Gln Leu Met Cys Leu Ala Arg Ser Val
1345                1350                1355                1360
Leu Ser Lys Ala Lys Ile Leu Leu Leu Asp Glu Pro Ser Ala His Leu
            1365                1370                1375
Asp Pro Val Thr Tyr Gln Ile Ile Arg Arg Thr Leu Lys Gln Ala Phe
            1380                1385                1390
Ala Asp Cys Thr Val Ile Leu Cys Glu His Arg Ile Glu Ala Met Leu
            1395                1400                1405
Glu Cys Gln Gln Phe Leu Val Ile Glu Glu Asn Lys Val Arg Gln Tyr
    1410                1415                1420
Asp Ser Ile Gln Lys Leu Leu Asn Glu Arg Ser Leu Phe Arg Gln Ala
1425                1430                1435                1440
Ile Ser Pro Ser Asp Arg Val Lys Leu Phe Pro His Arg Asn Ser Ser
            1445                1450                1455
Lys Cys Lys Ser Lys Pro Gln Ile Ala Ala Leu Lys Glu Glu Thr Glu
            1460                1465                1470
Glu Glu Val Gln Asp Thr Arg Leu
    1475                1480

<210> SEQ ID NO 7
<211> LENGTH: 20
<212> TYPE: DNA
<213> ORGANISM: Artificial Sequence
<220> FEATURE:
<223> OTHER INFORMATION: Forward primer for SVCT1

<400> SEQUENCE: 7
ttctggttgt gctgctgacc                                           20

<210> SEQ ID NO 8
<211> LENGTH: 21
<212> TYPE: DNA
<213> ORGANISM: Artificial Sequence
<220> FEATURE:
<223> OTHER INFORMATION: Reverse primer for SVCT1

<400> SEQUENCE: 8
tgtatcagac cacgctcctc t                                         21
```

```
<210> SEQ ID NO 9
<211> LENGTH: 20
<212> TYPE: DNA
<213> ORGANISM: Artificial Sequence
<220> FEATURE:
<223> OTHER INFORMATION: Forward primer for SVCT2

<400> SEQUENCE: 9
gctgttgcac acagaacaca                                              20

<210> SEQ ID NO 10
<211> LENGTH: 21
<212> TYPE: DNA
<213> ORGANISM: Artificial Sequence
<220> FEATURE:
<223> OTHER INFORMATION: Reverse primer for SVCT2

<400> SEQUENCE: 10
gaggaggccg atgactactt c                                            21

<210> SEQ ID NO 11
<211> LENGTH: 1953
<212> TYPE: DNA
<213> ORGANISM: Homo sapiens

<400> SEQUENCE: 11
atgatgggta ttggtaagaa taccacatcc aaatcaatgg aggctggaag ttcaacagaa    60
ggcaaatacg aagacgaggc aaagcaccca gctttcttca ctcttccggt ggtgataaat   120
ggaggcgcca cctccagcgg tgagcaggac aatgaggaca ctgagctcat ggcgatctac   180
actacggaaa acggcattgc agaaaagagc tctctcgctg agaccctgga tagcactggc   240
agtctggacc cccagcgatc agacatgatt tataccatag aagatgttcc tccctggtac   300
ctgtgtatat ttctggggct acagcactac ctgacatgct tcagcggcac gatcgcagtg   360
cccttcctgt tggccgatgc catgtgtgtg gggtacgacc agtgggccac cagccagctc   420
attgggacca ttttcttctg tgtgggaatc actactttgc tacagacaac gtttggatgc   480
aggttacccc tgtttcaggc cagtgctttt gcattttttgg cccctgctcg agccatcctg   540
tctttagata atggaaaatg taacaccaca gatgtttcag ttgccaatgg aacagcagag   600
ctgttgcaca cagaacacat ctggtatccc cggatccgag agatccaggg ggccatcatc   660
atgtcctcac tgatagaagt agtcatcggc ctcctcggcc tgcctggggc tctactgaag   720
tacatcggtc ccttgaccat tacacccacg gtggccctaa ttggcctctc tggttttccag   780 gcagcggggg agagagccgg gaagcactgg ggcattgcca tgctgacaat attcctagta   840
ttactgtttt ctcaatacgc cagaaatgtt aaatttcctc tcccgattta taatccaag   900 aaaggatgga ctgcgtacaa gttacagctg ttcaaaatgt tccctatcat cctggccatc   960
ctggtatcct ggctgctctg cttcatcttc acggtgacag acgtcttccc tcccgacagc  1020
acaaagtatg gcttctatgc tcgcacagat gccaggcaag gcgtgcttct ggtagccccg  1080
tggtttaagg ttccataccc atttcagtgg ggactgccca ccgtgtctgc ggccggtgtc  1140
atcggcatgc tcagtgccgt ggtcgccagc atcatcgagt ctattggtga ctactacgcc  1200
tgtgcacggc tgtcctgtgc cccacccccc ccatccacg caataaacag gggaattttc  1260
gtggaaggcc tctcctgtgt tcttgatggc atatttggta ctgggaatgg ctctacttca  1320
tccagtccca acattggagt tttgggaatt acaaaggtcg gcagccgccg cgtgatacag  1380
tgcggagcag ccctcatgct cgctctgggc atgatcggga agttcagcgc cctctttgcg  1440
```

-continued

```
tcccttccgg atcctgtgct gggagccctg ttctgcacgc tctttggaat gatcacagct    1500
gttggcctct ctaacctgca gttcattgat ttaaattctt cccggaacct ctttgtgctt    1560
ggattttcga tcttctttgg gctcgtcctt ccaagttacc tcagacagaa ccctctggtc    1620
acagggataa caggaatcga tcaagtgttg aacgtccttc tcacaactgc tatgtttgta    1680
gggggctgtg tggcttttat cctgataaac catcccag gcactccaga ggaaagagga     1740
atccggaaat ggaagaaggg tgtgggcaaa gggaacaaat cactcgacgg catggagtcg    1800
tacaatctgc catttggcat gaacattata aaaaaataca gatgcttcag ctacttaccc    1860
atcagcccaa cctttgtggg ctacacatgg aaaggcctca ggaagagcga caacagccgg    1920
agttcagatg aagactccca ggccacggga tag                                 1953

<210> SEQ ID NO 12
<211> LENGTH: 1953
<212> TYPE: DNA
<213> ORGANISM: Homo sapiens

<400> SEQUENCE: 12
atgatgggta ttggtaagaa taccacatcc aaatcaatgg aggctggaag ttcaacagaa      60
ggcaaatacg aagacgaggc aaagcaccca gctttcttca ctcttccggt ggtgataaat     120
ggaggcgcca cctccagcgg tgagcaggac aatgaggaca ctgagctcat ggcgatctac     180
actacggaaa acggcattgc agaaaagagc tctctcgctg agaccctgga tagcactggc     240
agtctggacc cccagcgatc agacatgatt tataccatag aagatgttcc tccctggtac     300
ctgtgtatat ttctggggct acagcactac ctgacatgct tcagcggcac gatcgcagtg     360
cccttcctgt tggccgatgc catgtgtgtg gggtacgacc agtgggccac cagccagctc     420
attgggacca ttttcttctg tgtgggaatc actactttgc tacagacaac gtttggatgc     480
aggttacccc tgtttcaggc cagtgctttt gcatttttgg ccctgctcg agccatcctg     540 tctttagata aatggaaatg taacaccaca gatgtttcag ttgccaatgg aacagcagag     600
ctgttgcaca cagaacacat ctggtatccc cggatccgag agatccaggg ggccatcatc     660
atgtcctcac tgatagaagt agtcatcggc ctcctcggcc tgcctggggc tctactgaag     720
tacatcggtc ccttgaccat tacacccacg gtggccctaa ttggcctctc tggtttccag     780
gcagcggggg agagagccgg gaagcactgg ggcattgcca tgctgacaat attcctagta     840
ttactgtttt ctcaatacgc cagaaatgtt aaatttcctc tcccgattta taaatccaag     900
aaaggatgga ctgcgtacaa gttacagctg ttcaaaatgt tccctatcat cctggccatc     960
ctggtatcct ggctgctctg cttcatcttc acggtgacag acgtcttccc tcccgacagc    1020
acaaagtatg gcttctatgc tcgcacagat gccaggcaag gcgtgcttct ggtagccccg    1080
tggtttaagg ttccataccc atttcagtgg ggactgccca ccgtgtctgc ggccggtgtc    1140
atcggcatgc tcagtgccgt ggtcgccagc atcatcgagt ctattggtga ctactacgcc    1200
tgtgcacggc tgtcctgtgc cccaccccc cccatccacg caataaacag gggaattttc    1260
gtggaaggcc tctcctgtgt tcttgatggc atatttggta ctgggaatgg ctctacttca    1320
tccagtccca acattggagt tttgggaatt acaaaggtcg gcagccgccg cgtgatacag    1380
tgcggagcag ccctcatgct cgctctgggc atgatcggga agttcagcgc cctctttgcg    1440
tcccttccgg atcctgtgct gggagccctg ttctgcacgc tctttggaat gatcacagct    1500
gttggcctct ctaacctgca gttcattgat ttaaattctt cccggaacct ctttgtgctt    1560
ggattttcga tcttctttgg gctcgtcctt ccaagttacc tcagacagaa ccctctggtc    1620
```

```
acagggataa caggaatcga tcaagtgttg aacgtccttc tcacaactgc tatgtttgta    1680
gggggctgtg tggcttttat cctggataac accatcccag gcactccaga ggaaagagga    1740
atccggaaat ggaagaaggg tgtgggcaaa gggaacaaat cactcgacgg catggagtcg    1800
tacaatttgc catttggcat gaacattata aaaaaataca gatgcttcag ctacttaccc    1860
atcagcccaa cctttgtggg ctacacatgg aaaggcctca ggaagagcga caacagccgg    1920
agttcagatg aagactccca ggccacggga tag                                 1953
```

COMPOSITIONS AND METHODS FOR THERAPY FOR DISEASES CHARACTERIZED BY DEFECTIVE CHLORIDE TRANSPORT

CROSS-REFERENCE TO RELATED APPLICATION

This application is a continuation-in-part of U.S. patent application Ser. No. 09/982,315, filed Oct. 17, 2001, which is a divisional of U.S. patent application Ser. No. 09/174,077, filed Oct. 16, 1998 now U.S. Pat. No. 6,329,422, which is a continuation-in-part of U.S. patent application Ser. No. 08/951,912, filed Oct. 16, 1997, now U.S. Pat. No. 5,972,995.

STATEMENT OF GOVERNMENT INTEREST

This invention was made with government support under Grant No. R01 HL071829 awarded by the National Institutes of Health. The government may have certain rights in this invention.

BACKGROUND OF THE INVENTION

1. Field of the Invention

The present invention relates generally to the treatment of diseases characterized by defective chloride transport, including cystic fibrosis, asthma, chronic obstructive pulmonary disease (COPD), and other inflammatory disorders of the airways, intestinal constipation, pancreatitis, and dry eye syndrome. The invention is more particularly related to compositions comprising one or more compounds such as flavones and/or isoflavones, and/or vitamin C and related compounds, which may be used to activate chloride transport (i.e., absorption and/or secretion) in epithelial tissues of the airways, the intestine, the pancreas and other exocrine glands.

2. Description of the Related Art

Cystic fibrosis is a lethal genetic disease afflicting approximately 30,000 individuals in the United States. Approximately 1 in 2500 Caucasians is born with the disease, making it the most common lethal, recessively inherited disease in that population.

Cystic fibrosis affects the secretory epithelia of a variety of tissues, altering the transport of water, salt and other solutes into and out of the blood stream. In particular, the ability of epithelial cells in the airways, liver, pancreas, small intestine, reproductive tract and other tissues to transport chloride ions, and accompanying sodium and water, is severely reduced in cystic fibrosis patients, resulting in respiratory, pancreatic and intestinal ailments. The principle clinical manifestation of cystic fibrosis is the resulting respiratory disease, characterized by airway obstruction due to the presence of thick mucus that is difficult to clear from airway surfaces. This thickened airway liquid contributes to recurrent bacterial infections and progressively impairs respiration, eventually resulting in death.

In cystic fibrosis, defective chloride transport is generally due to a mutation in a chloride channel known as the cystic fibrosis transmembrane conductance regulator (CFTR; see Riordan et al., *Science* 245:1066-73, 1989). CFTR is a linear chloride channel found in the plasma membrane of certain epithelial cells, where it regulates the flow of chloride ions in response to phosphorylation by a cyclic AMP-dependent kinase. Many mutations of CFTR have been reported, the most common of which is a deletion of phenylalanine at position 508 (ΔF508-CFTR), which is present in approximately 70% of patients with cystic fibrosis. A glycine to aspartate substitution at position 551 (G551D-CFTR) occurs in approximately 1% of cystic fibrosis patients.

Current treatments for cystic fibrosis generally focus on controlling infection through antibiotic therapy and promoting mucus clearance by use of postural drainage and chest percussion. However, even with such treatments, frequent hospitalization is often required as the disease progresses. New therapies designed to increase chloride ion conductance in airway epithelial cells have been proposed, but their long term beneficial effects have not been established and such therapies are not presently available to patients.

Hypersecretion of sticky mucus by the airways is a hallmark of inflammatory airway diseases, such as asthma, chronic bronchitis and COPD (chronic obstructive airway disease). Asthma is currently a worldwide problem, with increasing prevalence in both children and adults. Total prevalence is estimated to be 7.2% of the world's population (6% in adults, 10% in children). However, there can be wide variation between the prevalence of asthma in different countries and even within different areas of a country. About 20 million Americans report having asthma with more than 70% of people with asthma also suffering from allergies. Sixty percent of people with asthma suffer specifically from allergic asthma. In 1999, it was estimated that 24.7 million Americans have been diagnosed with asthma in their lifetime. Over six million children under 18 report having asthma.

Chronic bronchitis and COPD are commonly found in long-term smokers where excessive mucus secretions and poor mucociliary clearance cause recurring airway inflammation and destruction of the airway epithelium. Current treatment effects are limited and the prognosis of airway disease in long-term smokers is poor.

Accordingly, improvements are needed in the treatment of diseases characterized by defective chloride transport, such as cystic fibrosis, asthma, chronic obstructive pulmonary disease, and other inflammatory disorders of the airways, intestinal constipation, pancreatitis, and dry eye syndrome. The present invention fulfills this need and further provides other related advantages.

BRIEF SUMMARY OF THE INVENTION

Briefly stated, the present invention is directed to compositions and methods for enhancing chloride transport in epithelial cells and for the therapy of diseases characterized by defective cellular chloride transport.

One aspect of the present invention is directed to a method for treating a disease characterized by defective chloride transport in a mammal comprising administering to the mammal one or more compounds selected from the group consisting of ascorbic acid, ascorbate salts, dehydroascorbic acid and resveratrol. In one embodiment, the method further includes administering one or more compounds including but not limited to flavones and isoflavones, wherein the compound is capable of stimulating chloride transport, and wherein the compound is not genistein. In another embodiment, the compound includes one or more of quercetin, apigenin, kaempferol, biochanin A, flavanone, flavone, dihydroxyflavone, trimethoxy-apigenin, apigenin 7-O-neohesperidoside, fisetin, rutin, daidzein and prunetin. In yet another embodiment, the disease to be treated may be any one or more of asthma, cystic fibrosis, chronic obstructive pulmonary disease, intestinal constipation, pancreatitis, and dry eye syndrome. In certain embodiments, the compound or compounds described herein are administered orally. In one embodiment, the compounds of the present invention are administered by inhalation, or topically.

Another aspect of the present invention is directed to a method for treating a disease characterized by defective chloride transport in a mammal comprising; administering to the mammal one or more compounds selected from the group consisting of ascorbic acid, ascorbate salts, dehydroascorbic acid and resveratrol; administering to the mammal one or more compounds selected from the group consisting of flavones and isoflavones, wherein the compound is capable of stimulating chloride transport; and administering to the mammal one or more compounds selected from the group consisting of: a compound that increases expression of a CFTR in an epithelial cell; and a chemical chaperone that increases trafficking of a CFTR to a plasma membrane in an epithelial cell. In one embodiment, the disease to be treated may be cystic fibrosis or asthma. In a further embodiment, the compounds of the present invention to be administered are present within a composition comprising a physiologically acceptable carrier or excipient.

An additional aspect of the present invention is directed to a method of treating diarrhea comprising, administering to a patient showing symptoms of diarrhea, an effective amount of a compound that blocks vitamin C transport via SVCT1 and/or SVCT2 in intestinal epithelia. In one embodiment, the method includes further administering to the patient a CFTR chloride channel blocker.

In another aspect of the present invention, a method for identifying an agent that alters chloride transport is provided, comprising; contacting an epithelial cell expressing SVCT1 and/or SVCT2 with a test agent and ascorbate; measuring chloride transport in the epithelial cell contacted with the test agent and ascorbate as compared to an epithelial cell contacted with a control compound and ascorbate; wherein a statistically significant increase or decrease in chloride transport in the cell contacted with the test agent as compared to the chloride transport in the cell contacted with control compound indicates the test agent alters chloride transport.

Another aspect of the present invention is directed to a composition comprising: (a) one or more flavones or isoflavones capable of stimulating chloride secretion; (b) one or more of: (i) a compound that increases expression of a CFTR protein in an epithelial cell; and (ii) a chemical chaperone that increases trafficking of a CFTR protein to a plasma membrane in an epithelial cell; (c) one or more of a compound selected from the group consisting of ascorbic acid, ascorbate salts, dehydroascorbic acid and resveratrol; and (d) a physiologically acceptable carrier. In one embodiment, the compound of part (b) increases expression and/or trafficking of a mutated CFTR, such as a CFTR that has a mutation at position 551 and/or a CFTR that has a ΔF508 mutation.

An additional aspect of the present invention is directed to a method of identifying an agent that stimulates chloride transport, comprising: (a) contacting, in the absence and presence of a candidate agent, (i) an ascorbate compound, and (ii) a biological sample comprising a cell, under conditions and for a time sufficient to induce chloride transport; and (b) detecting chloride transport, wherein a level of detectable chloride transport that is increased in the presence of the candidate agent relative to the level of detectable chloride transport in the absence of the agent indicates an agent that stimulates chloride transport. In certain embodiments, the ascorbate compound is vitamin C or a derivative thereof. In another embodiment the candidate agent is a flavonoid or an isoflavonoid. In an additional embodiment, the cell is an epithelial cell. In a further embodiment, the cell comprises at least one transport molecule, such as a CFTR or a SVCT (e.g., SVCT1 or SVCT2). In one embodiment, the step of contacting does not increase a level of intracellular cAMP.

Another aspect of the present invention provides a method of identifying an agent that impairs chloride transport, comprising: (a) contacting, in the absence and presence of a candidate agent, (i) an ascorbate compound, and (ii) a biological sample comprising a cell, under conditions and for a time sufficient to induce chloride transport; and (b)detecting chloride transport, wherein a level of detectable chloride transport that is decreased in the presence of the candidate agent relative to the level of detectable chloride transport in the absence of the agent indicates an agent that impairs chloride transport. In one embodiment, the ascorbate compound is vitamin C or a derivative thereof. In another embodiment, the candidate agent may be a flavonoid or an isoflavonoid. In a further embodiment, the cell is an epithelial cell. In yet another embodiment, the cell comprises at least one transport molecule, such as a CFTR or a SVCT (e.g., SVCT1 or SVCT2). In one embodiment, the step of contacting does not increase a level of intracellular cAMP.

Within another aspect, the present invention provides methods for enhancing chloride transport in epithelial cells, comprising contacting epithelial cells with a compound selected from the group consisting of flavones and isoflavones, wherein the compound is capable of stimulating chloride transport and wherein the compound is not genistein. Within certain embodiments, the compound is (a) a polyphenolic compound having the general formula:

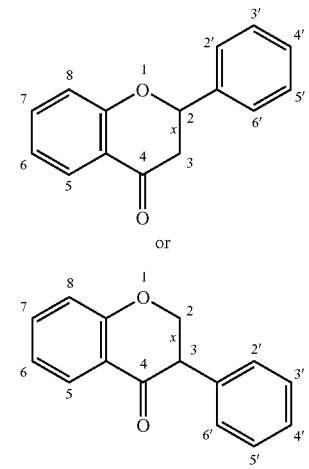

or wherein carbon atoms at positions 2, 3, 5, 6, 7, 8, 2', 3', 4', 5' and 6' are bonded to a moiety independently selected from the group consisting of hydrogen atoms, hydroxyl groups and methoxyl groups, and wherein X is a single bond or a double bond; or (b) a stereoisomer or glycoside derivative of any of the foregoing polyphenolic compounds. Such compounds include, within certain embodiments, quercetin, apigenin, kaempferol, biochanin A, flavanone, flavone, dihydroxyflavone, trimethoxy-apigenin, apigenin 7-O-neohesperidoside, fisetin, rutin, daidzein and prunetin. For enhancing chloride transport in airway epithelial cells of a mammal, compounds may be administered orally or by inhalation. Other epithelial cells that may be employed include intestinal, pancreas, gallbladder, sweat duct, salivary gland and mammary epithelial cells. Within certain embodiments, the compound is combined with a substance that increases expression of a CFTR; and/or a chemical chaperone that increases trafficking of a CFTR to the plasma membrane.

Within other aspects, methods for enhancing chloride transport in epithelial cells may comprise contacting epithelial cells with a compound selected from the group consisting of resveratrol, ascorbic acid, ascorbate salts and dehydroascorbic acid. Such compounds may further be used in combination with a flavone or isoflavone as provided above.

Within other aspects, the present invention provides methods for treating cystic fibrosis in a patient, comprising administering to a patient a compound as described above, wherein the compound is capable of stimulating chloride transport. Within certain embodiments, the compound is genistein, quercetin, apigenin, kaempferol, biochanin A, flavanone, flavone, dihydroxyflavone, trimethoxy-apigenin, apigenin 7-O-neohesperidoside, fisetin, rutin, daidzein or prunetin. Within other embodiments, the compound is resveratrol, ascorbic acid, ascorbate salts and dehydroascorbic acid. Such compounds may be administered alone or in combination. Compounds may be administered orally or by inhalation. Within certain embodiments, the compound is combined with a substance that increases expression of a CFTR; and/or a chemical chaperone that increases trafficking of a CFTR to the plasma membrane.

Within further related aspects, the present invention provides methods for increasing chloride ion conductance in airway epithelial cells of a patient afflicted with cystic fibrosis, wherein the patient's CFTR protein has a deletion at position 508, the method comprising administering to a mammal one or more compounds as described above, wherein the compound is capable of stimulating chloride secretion in the airway epithelial cells.

Within still further related aspects, the present invention provides methods for increasing chloride ion conductance in airway epithelial cells of a patient afflicted with cystic fibrosis, wherein the patient's CFTR protein has a mutation at position 551, the method comprising administering to a mammal one or more compounds as described above, wherein the compound is capable of stimulating chloride secretion in the airway epithelial cells.

Within further aspects, pharmaceutical compositions for treatment of cystic fibrosis are provided, comprising (a) one or more flavones or isoflavones capable of stimulating chloride transport and (b) one or more of: (i) a compound that increases expression of a CFTR in an epithelial cell; and/or (ii) a chemical chaperone that increases trafficking of a CFTR to a plasma membrane in an epithelial cell; and; and in combination with a pharmaceutically acceptable carrier. Within certain embodiments, the flavone or isoflavone may be genistein, quercetin, apigenin, kaempferol, biochanin A, flavanone, flavone, dihydroxyflavone, trimethoxy-apigenin, apigenin 7-O-neohesperidoside, fisetin, rutin, daidzein and/or prunetin, in combination with a pharmaceutically acceptable carrier.

Within still further aspects, a pharmaceutical composition for treatment of cystic fibrosis may comprise: (a) a polyphenolic compound having the general formula:

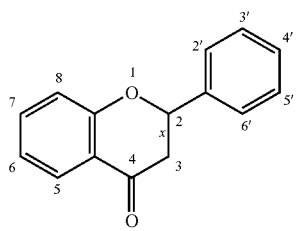

-continued
or

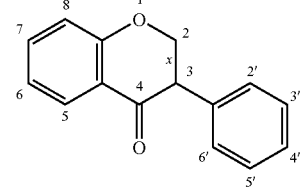

wherein carbon atoms at positions 2, 3, 5, 6, 7, 8, 2', 3', 4', 5'and 6'are bonded to a moiety independently selected from the group consisting of hydrogen atoms, hydroxyl groups and methoxyl groups, and wherein X is a single bond or a double bond; or a stereoisomer or glycoside derivative of any of the foregoing polyphenolic compounds; (b) a compound selected from the group consisting of resveratrol, ascorbic acid, ascorbate salts and dehydroascorbic acid; and (c) a physiologically acceptable carrier.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 12A shows a recording from a patient with the genotype G551 D/ΔF508. Amiloride, chloride free solution and isoproterenol were added as indicated. The addition of genistein, as indicated, hyperpolarized nasal PD. FIG. 12B is a graph illustrating the average responses of nasal PD to genistein and quercetin of four CF patients with the G551D mutation. The filled bars show, for comparison, the respective responses in healthy subjects.

FIG. 13A is a graph showing the stimulation of transepithelial chloride currents by resveratrol (100 μM), flavanone (100 μM), flavone (200 μM), apigenin (20 μM), apigenin 7-O-neohesperidoside (30 μM), kaempferol (20 μM), fisetin (100 μM), quercetin (30 μM), rutin (30 μM), genistein (30 μM), daidzein (50 μM), biochanin A (100 μM) and prunetin (100 μM) in Calu-3 monolayers. Experiments were performed in the presence of 10 μM forskolin. Stimulated currents are plotted relative to forskolin stimulated increase (forskolin stimulated currents are 100%). FIG. 13B is a recording showing the effect of 7,4'-dihydroxyflavone on chloride current in unstimulated tissue. This recording shows a dose-dependent stimulation of transepithelial short-circuit current (Isc) across Calu-3 monolayers by 7,4'-dihydroxyflavone. Increasing concentrations of 7,4'-dihydroxyflavone (as indicated in μM) were added to mucosal side and dose-dependently stimulated chloride currents. Currents were recorded with a serosal-to-mucosal chloride gradient at 0 mV and pulses were obtained at 2 mV. FIG. 13C is a recording illustrating the effect of trimethoxy-apigenin. This recording shows dose-dependent stimulation of transepithelial short-circuit current (Isc) across Calu-3 monolayers by trimethoxy-apigenin. Increasing concentrations of trimethoxy-apigenin (as indicated in μM) were added to mucosal side and dose-dependently stimulated chloride currents. Experiment was performed on unstimulated tissue. Currents were recorded with a serosal-to-mucosal chloride gradient at 0 mV and pulses were obtained at 2 mV.

FIG. 20 shows the stimulation of CFTR activity by L-ascorbic acid. A. Activation of single CFTR Cl channels by L-ascorbic acid (100 μM, bath) and forskolin (10 μM). Outside-out patch clamp recording from a Calu-3 airway epithelial cell (150:15 mM Cl gradient from bath to pipette, holding potential=75 mV). B. $P_o$ calculated from 20-s intervals from recording in A. C. Details of channel activity from recording in A. D. Single channel current-to-voltage relation, slope conductance is 8.9±0.2 pS (n=4). E. Effects of increasing concentrations of L-ascorbic acid (o), forskolin (•), and 100 nM forskolin in presence of 300 μM L-ascorbate (300 μM Asc+Fsk, •) on intracellular cAMP levels.

FIG. 21 shows activation of Cl transport by L-ascorbic acid. A. Measurements of transepithelial Cl secretion across Calu-3 airway epithelia in vitro. L-ascorbic acid (100 μM, mucosal) and forskolin (20 μM, serosal) activated and DPC (4 mM) blocked Cl currents. B. Dose-dependency of ascorbate-stimulated Cl currents. Half-maximal stimulatory constant averaged 36.5±2.9 μM (n=14). C. Nasal potential difference (NPD) measurements in humans. L-ascorbic acid (300 μM) and the cAMP agonist isoproterenol (10 μM) hyperpolarized NPD. Wash, washout with saline.

FIG. 24 shows activation of ΔF508 CFTR by L-ascorbic acid and D-isoascorbic acid after correction of the trafficking defect in CF mice. A. Measurements of rectal potential difference (RPD) in mice homozygous for ΔF508 CFTR. Arrow indicates perfusion with L-ascorbate (1 mM) or D-isoascorbate (300 μM). RPD was hyperpolarized by both ascorbates in CF mice treated with 4 mg/g TMAO for 24 hours (•, □), but not in water-injected mice (o). B. Summary of ascorbate-induced changes in RPD in TMAO-treated and control CF mice. ctrl, control; L-Asc, 1 mM L-ascorbate; D-Iasc, 300 μM D-isoascorbate. * significantly different from control CF mice, $p \leq 0.05$; n=3-9 experiments.

DETAILED DESCRIPTION OF THE INVENTION

Figure 1:
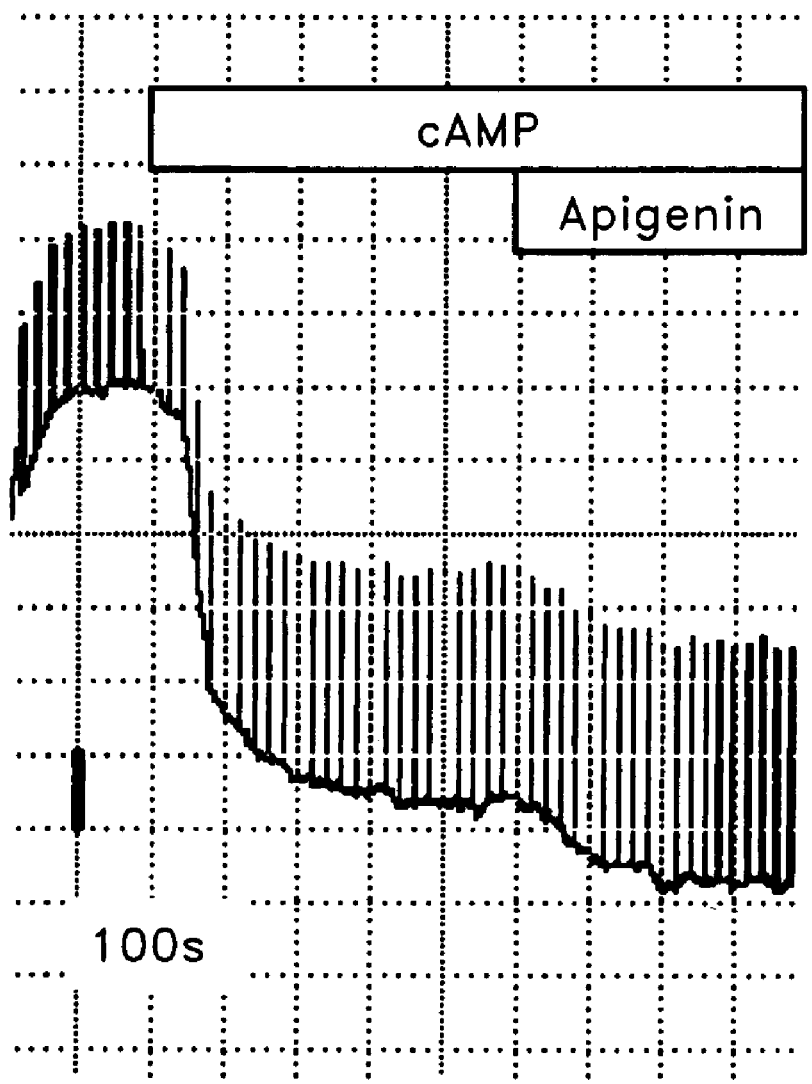
FIG. 1 is a recording of transepithelial short-circuit current (Y axis) as a function of time (X axis), showing the effect of apigenin on the current across a Calu-3 cell monolayer. Measurements were performed in an Ussing chamber, where the basolateral membrane was permeabilized with α-toxin and a chloride gradient was applied across the apical membrane as a driving force. Tissue was first stimulated with cAMP (100 µM). Apigenin (50 µM) was subsequently added as indicated. The horizontal bar represents 100 seconds, and the vertical bar represents 12 µA/cm$^2$.

As noted above, the present invention is generally directed to compositions and methods for the treatment of diseases characterized by defective chloride transport, particularly with regard to defective cellular chloride transport (e.g., defective export from or import to the cell of chloride, such as chloride anion or in the form of a chloride salt or other chloride-containing compound), for example, in epithelial tissues, including diseases such as cystic fibrosis, asthma, chronic obstructive pulmonary disease, and other inflammatory disorders of the airways, intestinal constipation, pancreatitis, and dry eye syndrome and also including diseases that feature excessive accumulation of mucus, including cystic fibrosis, chronic bronchitis and asthma. Within the context of the present invention, defective chloride transport may comprise a decrease (e.g., in a statistically significant manner) or lack of chloride transport as compared to normal physiological levels with which the skilled artisan will be familiar as a property of a particular cell or tissue type, organ system, or the like, or an increase(e.g., in a statistically significant manner) in chloride transport as compared to such normal levels.

It has been found, within the context of the present invention, that certain flavones and isoflavones, as well as other polyphenolic compounds, and ascorbate compounds such as ascorbic acid (vitamin C), and derivatives thereof, are capable of stimulating CFTR-mediated chloride transport in epithelial tissues (e.g., tissues of the airways, intestine, pancreas and other exocrine glands) in a cyclic-AMP independent manner. It has further been found, within the context of the present invention, that, under appropriate conditions, such compounds may stimulate chloride transport in certain cells, for example, cells having a mutated CFTR (e.g., ΔF508-CFTR or G551D-CFTR). Such therapeutic compounds may be administered to patients suspected of having or afflicted with a disease characterized by defective chloride transport (e.g., defective cellular chloride transport) such as, cystic fibrosis, asthma, chronic obstructive pulmonary disease, and other inflammatory disorders of the airways, intestinal constipation, pancreatitis, and dry eye syndrome as described herein.

The term "flavones," as used herein refers to a compound based on the core structure of flavone:

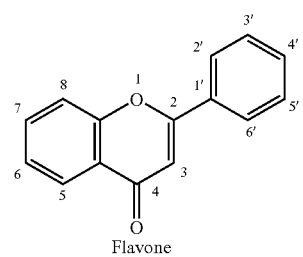

Flavone

An "isoflavone" is an isomer of a flavone (i.e., the phenyl moiety at position 2 is moved to position 3), and having the core structure shown below:

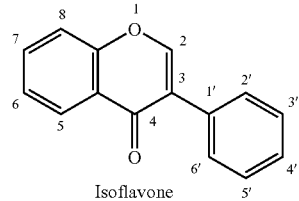
Isoflavone

Certain flavones and isoflavone have the structure:

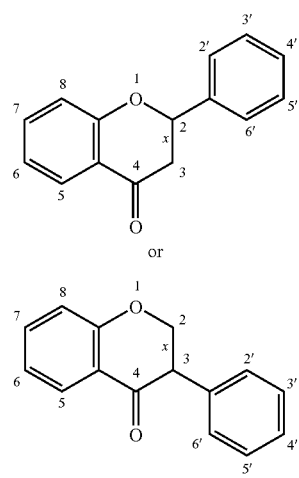

wherein carbon atoms at positions 2, 3, 5, 6, 7, 8, 2', 3', 4', 5' and 6' are bonded to a moiety independently selected from the group consisting of hydrogen atoms, hydroxyl groups and methoxyl groups, and wherein X is a single bond or a double bond. Stereoisomers and glycoside derivatives of such polyphenolic compounds may also be used within the methods provided herein.

Many flavones are naturally-occurring compounds, but synthetic flavones and isoflavones are also encompassed by the present invention. A flavone or isoflavone may be modified to comprise any of a variety of functional groups, such as hydroxyl and/or ether groups. Preferred flavones comprise one or more hydroxyl groups, such as the trihydroxyflavone apigenin, the tetrahydroxyflavone kaempferol and the pentahydroxyflavone quercetin. Preferred isoflavones comprise one or more hydroxyl and/or methoxy groups, such as the methoxy, dihydroxy isoflavone biochanin A. Genistein is yet another preferred isoflavone for use within the methods provided herein.

Any flavone or isoflavone, or ascorbate compound (e.g., ascorbic acid, ascorbate, or a derivative thereof), that stimulates (e.g., increases with statistical significance) chloride transport within at least one of the assays described herein may be used for therapy of diseases characterized by defective chloride transport as provided herein including, for example, cystic fibrosis and other diseases characterized by abnormally high mucus accumulation in the airways, asthma, chronic obstructive pulmonary disease, and other inflammatory disorders of the airways, intestinal constipation, pancreatitis, and dry eye syndrome. Preferred therapeutic compounds include flavones and isoflavones that occur naturally in plants and are part of the human diet. Preferred compounds include genistein (4',5,7-trihydroxyisoflavone), as well as quercetin (3,3',4',5,7-pentahydroxyflavone), apigenin (4'5,7-trihydroxyflavone), kaempferol (3,4',5,7-tetrahydroxyflavone) and biochanin A (4'-methoxy-5,7-dihydroxyisoflavone), as depicted below:

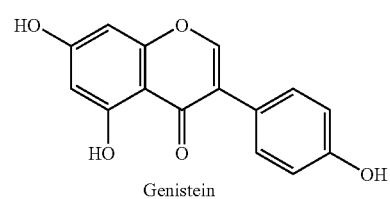
Genistein

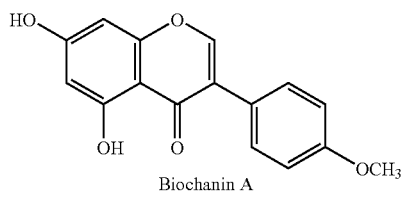
Biochanin A

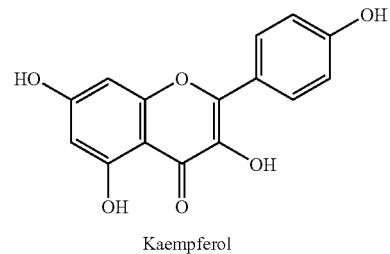
Kaempferol

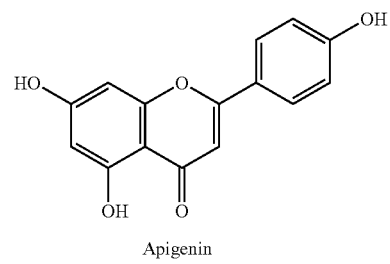
Apigenin

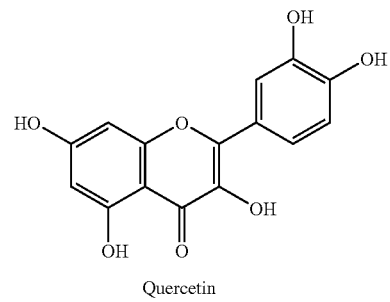
Quercetin

Other suitable therapeutic compounds may be identified using the representative assays as described herein. Additional representative flavones and isoflavones include flavanone, flavone, dihydroxyflavone, trimethoxy-apigenin, apigenin 7-O-neohesperidoside, fisetin, rutin, daidzein and prunetin. Representative flavones and isoflavones are summarized in Tables I and II.

TABLE I

| | | | Flavonoids | | | |
|---|---|---|---|---|---|---|
| No. | Name | X | C3 | C5 | C7 | C3' | C4' |
| 1 | Apigenin | = | | OH | OH | | OH |
| 2 | Apigenin7-O-neohesperidoside | = | | OH | ONeo | | OH |
| 3 | Dihydroxyflavone | = | | OH | | | OH |
| 4 | Flavone | = | | | | | |
| 5 | Flavanone | — | | | | | |
| 6 | Fisetin | = | OH | | OH | OH | OH |
| 7 | Kaempferol | = | OH | OH | OH | | OH |
| 8 | Quercetin | = | OH | OH | OH | OH | OH |
| 9 | Rutin | = | ORut | | OH | OH | OH |
| 10 | Trimethoxyapigenin | = | H | OCH3 | OCH3 | | OCH3 | where
= a double bond,
— is a single bond,
ONeo is Neohesperidoside,
ORut is rutinoside,
OCH3 is methoxy,
OH is hydroxy

TABLE II

| | | | Isoflavonoids | | |
|---|---|---|---|---|---|
| No. | Name | X | C5 | C7 | C4' |
| 11 | Biochanin | = | OH | OH | OCH3 |
| 12 | Daidzein | = | | OH | OH |
| 13 | Genistein | = | OH | OH | OH |
| 14 | Prunetin | = | OH | OCH3 | OH | where
= a double bond,
— is a single bond
ONeo is Neohesperidoside,
ORut is rutinoside,
OCH3 is methoxy,
OH is hydroxy.

Genistein, quercetin, apigenin, kaempferol, biochanin A and other s and isoflavones may generally be prepared using well known techniques, those described by Shakhova et al., Zh. Obshch. Khim. 32:390, 1962; Farooq et al., Arch. Pharm. 292:792, 1959; and Ichikawa et al., Org. Prep. Prog. Int. 14:183, 1981. Alternatively, such compounds may be commercially available (e.g., from Indofine Chemical Co., Inc., Somerville, N.J. or Sigma-Aldrich, St. Louis, Mo.). Further modifications to such compounds may be made using conventional organic chemistry techniques, which are well known to those of ordinary skill in the art.

As noted above, other polyphenolic compounds may be used within the methods provided herein. For example, trihydroxystilbenes such as resveratrol (trans-3,5,4'-trihydroxystilbene) may be employed. Resveratrol is a polyphenolic compound having the following structure:

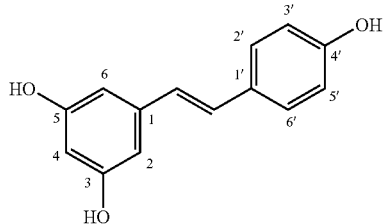

Other compounds that may be used within the methods provided herein are ascorbate compounds such as ascorbic acid (vitamin C) and derivatives thereof. Accordingly and as provided herein, reference to ascorbate, ascorbic acid or vitamin C contemplates similar uses of other ascorbate derivatives having similar effects on chloride transport (e.g., cellular chloride transport) as those presently disclosed. Vitamin C, is a required micronutrient for humans (Nishikimi, M., et al., (1994) J. Biol. Chem. 269, 13685-13688.) Dietary vitamin C acts as a cofactor for several intracellular enzymes and scavenges free radicals (Rumsey, S. C. et al., (1998) J. Nutr. Biochem. 9, 116-130.). In the lungs and respiratory tract vitamin C mainly functions as an electron donor for reactive oxygen species (Willis, R. J., et al., (1976) Biochim. Biophys. Acta 444, 108-111; Slade, R., et al., (1993) Exp. Lung Res. 19, 469-484; van der Vliet, A., et al., (1999) Am. J. Physiol. 276, L289-L296; Kelly, F. J., et al., (1999) Lancet 354, 482-483). Epidemiological studies suggested a link between high dietary intake of vitamin C and its protective effects against respiratory symptoms (Schwartz, J., et al., (1994) Am. J. Clin. Nutr. 59, 110-114), however an alarming 25% of the U.S. population did not meet the recommended dietary intake levels for vitamin C as published in the Third National Health and Nutrition Examination Survey (NHANES III, 1988-1994) (Food and Nutrition Board Institute of Medicine (2002) in Dietary Reference Intakes for Vitamin C, Vitamin E, Selenium, and Carotenoids (Natl. Acad. Press, Wash. D.C.), pp. 95-185). Insufficient dietary intake of vitamin C (Kodavanti, et al., (1996) Exp. Lung Res. 22(4), 435-448), environmental pollutants (Kodavanti, et al., Supra; Cross, et al., (1992) FEBS Lett. 298, 269-272) and a number of inflammatory disorders of the airways are known to severely deplete physiological pools of vitamin C in the respiratory tract. For example, low levels of vitamin C were found in patients with bronchial asthma (Kelly, et al., Supra; Menzel, D. B. (1992) Ann. N Y Acad. Sci. 669, 141-155.), cystic fibrosis (Winklhofer-Roob, etal., (1997) Am. J. Clin. Nutr. 65, 1858-66; Brown, et al., (1997) Am. J. Physiol. 273, L782-L788), chronic obstructive pulmonary disease (Calikoglu, et al., (2002) Clin. Chem. Lab. Med. 40, 1028-1031), acute respiratory distress syndrome (Cross, et al., (1990) J. Lab. Clin. Med. 115, 396-404), and smokers (Lykkesfeldt, et al., (2000) Am. J. Clin. Nutr. 71, 530-536) as well as in children exposed to environmental tobacco smoke (Preston, et al., (2003) Am. J. Clin. Nutr. 77, 167-172). In addition to its well known function as an antioxidant in many species including mammalian species, in amphibians a regulatory function of vitamin C on Cl transport across the cornea has been demonstrated (Scott, et al., (1975) Invest. Ophthalmol. 14, 763-6).

The cystic fibrosis transmembrane conductance regulator chloride channel (CFTR) was cloned in 1989 (Riordan, et al., (1989) Science 245, 1066-73). In the respiratory tract CFTR mediates the transport of $Cl^-$ across the epithelial cell apical membrane into the extracellular airway surface liquid (ASL), which transport is regulated to properly adjust ASL salt composition. The dynamics of the ASL affect its physiological function, the most important of which is the removal of inhaled particles and the support of mucociliary clearance (Widdicombe (1995) *Am. J. Respir. Crit. Care Med.* 151, 2088-2092). CF-like symptoms such as thickened airway secretions are often seen in chronic inflammatory airway diseases without mutations in the CFTR gene, and there is emerging evidence that post-translational damage to CFTR by reactive oxygen and nitrogen species decreases CFTR function (Bebok, et al. (2002) *J. Biol. Chem.* 277, 43041-43049).

As described in greater detail below and in the examples, the experiments described herein were designed to investigate the role of ascorbate compounds such as vitamin C in controlling Cl⁻ secretion and to clarify the potential involvement of CFTR in the underlying Cl⁻ conductance.

Accordingly, other compounds that may be used within the methods provided herein are ascorbic acid and derivatives thereof. Such compounds include L-ascorbic acid (L-xyloascorbic acid), dehydroascorbic acid (L-threo-2,3-Hexodiulosonic acid γ-lactone) and salts of the foregoing acids (e.g., L(+)-Ascorbic acid sodium salt, L(+)-Ascorbic acid iron(II) salt), as well as other ascorbate compounds as provided herein (e.g., L-Ascorbic acid 6-palmitate, L-Ascorbic acid 2-phosphate sesqui-magnesium salt, L-ascorbic acid 2-phosphate trisodium salt, L-Ascorbic acid 2-sulfate dipotassium salt) and other ascorbate compounds known to the art (see for example, J Biol Chem. 1999 Aug. 13; 274(33): 23215-22; Yamamoto, et al., J Nutr Sci Vitaminol (Tokyo). 1992; Spec No: 161-4; Hornig D.

Ann N Y Acad Sci. 1975 Sep. 30; 258: 103-18), and which have detectable effects on chloride transport (e.g., cellular chloride transport) as herein disclosed.

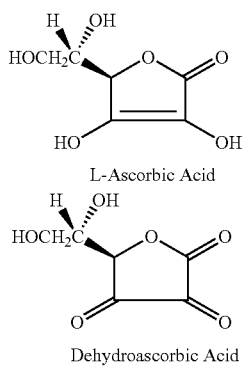

L-Ascorbic Acid

Dehydroascorbic Acid

Within certain preferred embodiments, ascorbic acid or a derivative thereof is used in combination with a polyphenolic compound as described above. Certain representative combinations include ascorbic acid and one or more flavenoids and/or isoflavenoids (such as genistein and ascorbic acid; and kaempferol and ascorbic acid). Ascorbic acid may generally be used to treat or prevent genetic loss of chloride secretory function (e.g., cystic fibrosis), as well as other related loss or reduced chloride secretory function (e.g., intestinal constipation, dry eye syndrome, asthma, and obstructive airway diseases).

Certain embodiments disclosed herein relate to the observation that the effect of vitamin C on chloride transport depends on the function of the sodium-dependent vitamin C transporters (SVCT) (see in particular Example 13; the sequences for SVCTs are known in the art and are available, for example, via Genbank Accession Numbers SVCT1: NM_005847 and SVCT2: AY380556). In certain embodiments, such as for the treatment of diarrhea resulting from high dose vitamin C treatment, it may be desirable to block vitamin C transport in intestinal epithelial cells. As such, the present invention contemplates the use of agents, including but not limited to, for example, phloretin and derivatives thereof, that block or otherwise decrease vitamin C transport in intestinal epithelia, in a statistically significant manner, such as through SVCT1 and SVCT2. Accordingly, provided herein are methods for identifying agents that alter chloride transport by contacting a cell (e.g., an epithelial cell) such as a cell that expresses SVCT1 and/or SVCT2, with a test agent and an ascorbate compound (e.g., vitamin C, ascorbic acid, ascorbate salts, dehydroascorbic acid or derivatives thereof) and measuring chloride transport in the cell that has been contacted with the test agent and vitamin C as compared to chloride transport in a cell that has been contacted with vitamin C in the absence of the test agent, for instance, in the presence of a control compound known not to affect chloride transport. In this regard a statistically significant increase or decrease in chloride transport in cells contacted with the test agent and vitamin C as compared to the cells contacted with vitamin C in the absence of the test agent, or in the presence of a control compound, indicates the agent alters chloride transport. Such agents can be identified by measuring chloride transport using any of the assays described herein and can also be identified using assays that screen for inhibition of SVCT1 and SVCT2 (e.g., by measuring vitamin C transport). Such agents can be identified using the assays as described herein, or known in the art (Tsukaguchi, H., Tokui, T., Mackenzie, B., Berger, U. V., Chen, X. Z., Wang, Y., Brubaker, R. F. & Hediger, M. A. (1999) *Nature* 399, 70-75).

As used herein, epithelial cells include any cell of epithelioid origin as known to those familiar with the art, and may be present in a biological sample as provided herein, for example a cell derived from a mammalian organ outer layer (e.g., skin, renal cortical layer, etc.) or an organ lining layer (e.g., gastric epithelia, intestinal epithelia, etc.) such as mammalian epithelial cells that are capable of forming one or more specialized structures, including desmosomes, tight junctions, adhesion plaques, distinct apical and basolateral regions, and the like.

Assays for Evaluating Chloride Transport

Flavones, isoflavones, ascorbate compounds such as ascorbic acid and derivatives thereof for use within the context of the present invention have the ability to stimulate chloride transport in epithelial tissues. Such transport may result in secretion or absorption of chloride ions. The ability to stimulate chloride transport may be assessed using any of a variety of systems. For example, in vitro assays using a mammalian trachea or a cell line, such as the permanent airway cell line Calu-3 (ATCC Accession Number HTB55) may be employed. Alternatively, the ability to stimulate chloride transport may be evaluated within an in vivo assay employing a mammalian nasal epithelium. In general, the ability to stimulate chloride transport may be assessed by evaluating CFTR-mediated currents across a membrane by employing standard Ussing chamber (see Ussing and Zehrahn, *Acta. Physiol. Scand.* 23:110-127, 1951) or nasal potential difference measurements (see Knowles et al., *Hum. Gene Therapy* 6:445-455, 1995). Within such assays, a flavone or isoflavone that stimulates a statistically significant increase in chloride transport, in certain preferred embodiments, at a concentration of about 1-10,000 µM, and in certain other preferred embodiments at a concentration of 0.1-1,000 µM (and all concentrations therebetween) is said to stimulate chloride transport. Generally, with regard to an ascorbate compound such as ascorbic acid or a derivative thereof, stimulation of a statistically significant increase in chloride transport, for example, at a concentration of about 1 to about 300 µM and in certain other preferred embodiments at a concentration of 0.1-1,000 µM (and all concentration therebetween) is said to comprise stimulated chloride transport. In another embodiment, at least about 5% increase of chloride transport is considered beneficial. In certain embodiments, increased chloride transport by at least about 10%-15% may be considered beneficial. In an additional embodiment, increased chloride transport by at least about 5%, 6%, 7%, 8%, 9%, 10%, 11%, 12%, 13%, 14%, 15%, 16%, 17%, 18%, 19%, or 20%, is considered beneficial. In other embodiments, it is considered beneficial if a compound, such as those described herein, provides a stimulatory effect on chloride transport at a level that is about 25%-60% of the level of chloride transport that is stimulated using commonly known CFTR agonists (e.g., forskolin). By way of non-limiting theory and as described herein, and in contrast to the situation that pertains to certain presently known CFTR agonists such as forskolin, a known elevator of intracellular cAMP, according to certain embodiments the invention relates to chloride transport that may be altered (e.g., increased or decreased in a statistically significant manner) under conditions that do not effect an increased level of intracellular cAMP, which may refer to any detectable increases in intracellular cAMP levels that are statistically significant and that are typically greater than 5%, 10%, 20%, 30%, 40%, 50% or more above the intracellular cAMP levels that exist in a particular biological system prior to introduction of the conditions that alter chloride transport.

Certain embodiments of the invention as disclosed herein relate to detecting chloride transport, and in particular to detecting chloride transport by cells, which may typically pertain to detection of cellular export of intracellular chloride to the extracellular environment. As described herein and known in the art, CFTR represents an important transmembrane channel for chloride transport through the cellular plasma membrane, and in humans CFTR is the major chloride transport channel. For example, certain single amino acid defects in CFTR manifest themselves as lethal mutations in CF, underscoring the importance of CFTR as a primary means for transporting chloride. Accordingly, based upon the present disclosure any of a number of art accepted methodologies may be used for detecting chloride transport such as CFTR-mediated chloride transport. By way of illustration and not limitation, descriptions of several such chloride transport assays, including in vitro and in vivo methodologies, are presented.

Within one in vitro assay, the level of chloride transport may be evaluated using mammalian pulmonary cell lines, such as Calu-3 cells, or primary human, rat, mouse and bovine tracheal and alveolar cell cultures, as well as intestinal epithelial cell lines, such as T84, HT-29, Caco-2 and cell lines of other epithelial origin such as MDCK and FRT. In general, such assays employ cell monolayers, which may be prepared by standard cell culture techniques. Within such systems, CFTR-mediated chloride current may be monitored in an Ussing chamber using intact epithelia. Anion efflux assays may be used to detect CFTR-mediated transport (e.g., iodide efflux, see for example RNA. 2003 October; 9(10): 1290-7). Additionally, chloride transport (or generally airway surface liquid composition), can be evaluated using any number of indicators such as described in J Gen Physiol. 2003 November; 122(5): 511-9. Alternatively, chloride transport may be evaluated using epithelial tissue in which the basolateral membrane is permeabilized with anion-selective ionophores such as nystatin, amphotericin B or *Staphylococcus aureus* α-toxin, and in which a chloride gradient is imposed across the apical membrane (see Illek et al., *Am. J. Physiol.* 270: C265-75, 1996). In either system, chloride transport is evaluated in the presence and absence of a test compound (i.e., a flavone or isoflavone, or ascorbate or derivative thereof), and those compounds that stimulate chloride transport as described above may be used within the methods provided herein.

Within another in vitro assay for evaluating chloride transport, cells are transfected with a chloride channel gene (e.g., CFTR) having a mutation associated with cystic fibrosis. Any CFTR gene that is altered relative to the normal human sequence provided in SEQ ID NO:1, such that the encoded protein contains a mutation associated with cystic fibrosis, may be employed within such an assay. The most common disease-causing mutation in cystic fibrosis is a deletion of phenylalanine at position 508 in the CFTR protein (ΔF508-CFTR; SEQ ID NO:4). Accordingly, the use of a CFTR gene encoding ΔF508-CFTR is preferred. However, genes encoding other altered CFTR proteins (e.g., G551D-CFTR; containing a glycine to aspartate point mutation at position 551; SEQ ID NO:6) may also be used. Cells such as NIH 3T3 fibroblasts may be transfected with an altered CTFR gene, such as ΔF508-CFTR, using well known techniques (see Anderson et al., *Science* 25:679-682, 1991). The effect of a compound on chloride transport in such cells may be evaluated by monitoring CFTR-mediated currents using the patch clamp method (see Hamill et al., *Pflugers Arch.* 391:85-100, 1981) with and without compound application.

Within another in vitro assay, a mutant CFTR may be microinjected into cells such as Xenopus oocytes. Chloride conductance mediated by the CFTR mutant in the presence and absence of a test compound (e.g., flavone, isoflavone, ascorbate or derivatives thereof) may be monitored with the two electrode voltage clamp method (see Miledi et al., *Proc. R. Soc. Lond. Biol.* 218:481-484, 1983).

Alternatively, such assays may be performed using a mammalian trachea, such as a primary human, mouse, sheep, pig or cow tracheal epithelium using the Ussing chamber technique as described above. Such assays are performed in the presence and absence of test compound to identify flavones, isoflavones, ascorbate or derivatives thereof that stimulate chloride transport.

Any of the assays described herein may be performed in the presence of cAMP agonists known in the art and as described herein (see Example 8 and other examples herein).

Any of the above assays may be performed following pre-treatment of the cells with a substance that increases the concentration of CFTR mutants in the plasma membrane. Such substances include chemical chaperones, which support correct trafficking of the mutant CFTR to the membrane, and compounds that increase expression of CFTR in the cell (e.g., transcriptional activators). A "chemical chaperone," as used herein is any molecule that increases trafficking of proteins to a cell membrane. More specifically, a chemical chaperone within the context of the present invention increases trafficking of a mutant CFTR (e.g., the Δ508-CFTR and/or G551D-CFTR) to the membrane by a statistically significant amount. Chemical chaperones for use herein include, but are not limited to, glycerol, dimethylsulfoxide, trimethylamine N-oxide, taurin, methylamine and deoxyspergualin (see Brown et al., *Cell Stress Chaperones* 1:117-125, 1996; Jiang et al., *Amer J. Physiol.-CellPhysiol.* 44:C171-C178, 1998). Compounds that increase expression of CFTR in the cell include 4-phenylbutyrate (Rubenstein et al., *J. Clin. Invest.* 100:2457-2465, 1997), sodium butyrate (Cheng et al., *Am. J. Physiol.* 268:

L615-624, 1995) and S-Nitrosoglutathione (Zaman, et al., Biochem Biophys Res Commun 284: 65-70, 2001; Snyder, et al., American Journal of Respiratory and Critical Care Medicine 165: 922-6, 2002; Andersson, et al. Biochemical and Biophysical Research Communication 297(3): 552-557, 2002.). Other compounds that increase the level of CFTR in the plasma membrane (by increasing correct trafficking and/or expression of the CFTR) may be readily identified using well known techniques, such as Western Blotting and immunohistochemical techniques, to monitor maturation of CFTR and evaluate effects on levels of plasma membrane CFTR, respectively.

In vivo, chloride secretion may be assessed using measurements of nasal potential differences in a mammal, such as a human or a mouse. Such measurements may be performed on the inferior surface of the inferior turbinate following treatment of the mucosal surface with a test compound during perfusion with the sodium transport blocker amiloride in chloride-free solution. The nasal potential difference is measured as the electrical potential measured on the nasal mucosa with respect to a skin electrode placed on a slightly scratched skin part (see Alton et al., Eur. Respir. J. 3:922-926, 1990) or with respect to a subcutaneous needle (see Knowles et al., Hum. Gene Therapy 6:445-455, 1995). Nasal potential difference is evaluated in the presence and absence of test compound, and those compounds that results in a statistically significant increase in nasal potential difference stimulate chloride transport.

Compounds as provided herein may generally be used to increase chloride transport within any of a variety of CFTR-expressing epithelial cells. CFTR is expressed in may epithelial cells, including intestinal, airway, lung, pancreas, gallbladder, kidney, sweat gland, lacrimal gland, salivary gland, mammary epithelia, epithelia of the male and female reproductive tract, and non epithelial cells including lymphocytes. All such CFTR-expressing organs are subject to stimulation by the compounds provided herein.

Accordingly, certain embodiments of the invention relate to a method of identifying an agent that stimulates (or impairs, and in either event in a statistically significant manner) chloride transport (e.g., cellular transport of chloride across a plasma membrane), comprising contacting in the absence and presence of a candidate agent an ascorbate compound and a biological sample comprising a cell, under conditions and for a time sufficient to induce chloride transport; and detecting chloride transport, wherein a level of detectable chloride transport that is increased in the presence of the candidate agent relative to the level of detectable chloride transport in the absence of the agent indicates an agent that stimulates chloride transport (and wherein, similarly, a level of detectable chloride transport that is decreased in the presence of the candidate agent relative to the level of detectable chloride transport in the absence of the agent indicates an agent that impairs chloride transport). In certain related further embodiments the ascorbate compound may be vitamin C or a derivative thereof, and in certain other related further embodiments the candidate agent may be a flavonoid. In certain other related embodiments the cell comprises a CFTR and/or a vitamin C TR. In certain preferred embodiments the step of contacting does not increase the intracellular cAMP level.

Certain chloride transport assays may be adapted to a high throughput screening (HTS) format and thus may be especially suited to automated screening of large numbers of candidate agents for activity in assays of chloride transport. HTS has particular value, for example, in screening synthetic or natural product libraries for active compounds. The methods of the present invention are therefore amenable to automated, cost-effective high throughput drug screening and have immediate application in a broad range of pharmaceutical drug development programs. In a preferred embodiment of the invention, the compounds to be screened are organized in a high throughput screening format such as a 96-well plate format, or other regular two dimensional array, such as a 384-well, 48-well or 24-well plate format or an array of test tubes. For high throughput screening the format is therefore preferably amenable to automation. It is preferred, for example, that an automated apparatus for use according to high throughput screening embodiments of the present invention is under the control of a computer or other programmable controller. The controller can continuously monitor the results of each step of the process, and can automatically alter the testing paradigm in response to those results.

Typically, and in preferred embodiments such as for high throughput screening, candidate agents are provided as "libraries" or collections of compounds, compositions or molecules. Such molecules typically include compounds known in the art as "small molecules" and having molecular weights less than $10^5$ daltons, preferably less than $10^4$ daltons and still more preferably less than $10^3$ daltons. For example, members of a library of test compounds can be administered to a plurality of samples in each of a plurality of reaction vessels in a high throughput screening array as provided herein, each containing at least one cell and being present in a form that permits conditions for inducing detectable chloride transport according to principles described herein. Candidate agents further may be provided as members of a combinatorial library, which preferably includes synthetic agents prepared according to a plurality of predetermined chemical reactions performed in a plurality of reaction vessels. For example, various starting compounds may be prepared employing one or more of solid-phase synthesis, recorded random mix methodologies and recorded reaction split techniques that permit a given constituent to traceably undergo a plurality of permutations and/or combinations of reaction conditions. The resulting products comprise a library that can be screened followed by iterative selection and synthesis procedures, such as a synthetic combinatorial library of peptides (see e.g., PCT/US91/08694 and PCT/US91/04666) or other compositions that may include small molecules as provided herein (see e.g., PCT/US94/08542, EP 0774464, U.S. Pat. No. 5,798,035, U.S. Pat. No. 5,789,172, U.S. Pat. No. 5,751,629). Those having ordinary skill in the art will appreciate that a diverse assortment of such libraries may be prepared according to established procedures, and tested for effect on chloride transport according to the present disclosure, using a biological sample (e.g., a cell such as an epithelial cell, or other suitable preparation of a cell, tissue, organ, or the like, for instance primary cell cultures, biopsy cells, tissue explants, established cell lines including transformed, immortal or immortalized cells, or other naturally occurring or genetically engineered cells or artificial cells).

Compositions and Methods of Use

For in vivo use, a compound as described herein is generally incorporated into a pharmaceutical composition prior to administration. Within such compositions, one or more therapeutic compounds as described herein are present as active ingredient(s) (i.e., are present at levels sufficient to provide a statistically significant effect on nasal potential difference, as measured using a representative assay as provided herein). A pharmaceutical composition comprises one or more such compounds in combination with any physiologically acceptable carrier(s) and/or excipient(s) known to those skilled in the art to be suitable for the particular mode of administration. In addition, other pharmaceutically active ingredients (including other therapeutic agents) may, but need not, be present within the composition.

In certain embodiments, an ascorbate compound or a derivative thereof and a flavonoid or isoflavonoid can be combined to additively open CFTR and thereby stimulate chloride transport. Within certain methods provided herein, a flavone, isoflavone, or derivative thereof, ascorbic acid or derivatives thereof, alone or in combination, may be combined with a substance that increases the concentration of CFTR mutants in the plasma membrane of a cell. As noted above, such substances may include a chemical chaperone, which supports correct trafficking of the mutant CFTR to the membrane, and may also include compounds that increase expression of CFTR in the membrane. These substances may be contained within the same pharmaceutical composition or may be administered separately. Preferred chemical chaperones include, for example, glycerol, dimethylsulfoxide, trimethylamine N-oxide, taurin, methylamine and deoxyspergualin, or the like, and compounds that increase expression of CFTR in the membrane include 4-phenylbutyrate and sodium butyrate, or the like. The use of flavonoid and/or isoflavonoid compounds, or ascorbic acid and derivatives thereof, as described herein, in combination with such substances may increase mutant CFTR activity, and ameliorate symptoms of diseases associated with defective chloride transport, such as cystic fibrosis.

In certain embodiments, the compounds described herein may be used to treat diarrhea, in particular diarrhea associated with vitamin C treatment. By way of non-limiting theory, CFTR blockers have been employed in the treatment of diarrhea (e.g., U.S. Pat. No. 5,234,922) whereas according to the instant disclosure and as described herein, agents that decrease vitamin C transporter activity are for the first time recognized as effecting decreased CFTR-mediated chloride transport. As such, the compositions, such as compositions comprising compounds that block vitamin C transporters (e.g., SVCT1 and/or SVCT2), can be administered alone or in combination with CFTR blockers. Such compositions as well as other compositions described herein may be in combination with any physiologically acceptable carrier(s) and/or excipient(s) known to those skilled in the art to be suitable for the particular mode of administration.

Administration may be achieved by a variety of different routes. Preferred are methods in which the therapeutic compound(s) are directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of a variety of cosolvents, surfactants, stabilizers (e.g., antioxidants, chelating agents, inert gases and buffers). For compositions to be administered from multiple dose containers, antimicrobial agents are typically added. Such compositions are also generally filtered and sterilized, and may be lyophilized to provide enhanced stability and to improve solubility.

Another preferred route is oral administration of a composition such as a pill, capsule or suspension. Such compositions may be prepared according to any method known in the art, and may comprise any of a variety of inactive ingredients. Suitable excipients for use within such compositions include inert diluents (which may be solid materials, aqueous solutions and/or oils) such as calcium or sodium carbonate, lactose, calcium or sodium phosphate, water, arachis oil, peanut oil liquid paraffin or olive oil; granulating and disintegrating agents such as maize starch, gelatin or acacia and/or lubricating agents such as magnesium stearate, stearic acid or talc. Other inactive ingredients that may, but need not, be present include one or more suspending agents (e.g., sodium carboxymethylcellulose, methylcellulose, hydroxypropylmethylcellulose, sodium alginate, polyvinylpyrrolidone, gum tragacanth and gum acacia), thickeners (e.g., beeswax, paraffin or cetyl alcohol), dispersing or wetting agents, preservatives (e.g., antioxidants such as ascorbic acid), coloring agents, sweetening agents and/or flavoring agents.

A pharmaceutical composition may be prepared with carriers that protect active ingredients against rapid elimination from the body, such as time release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

In general, the compositions of the present invention may be administered by the topical, transdermal, oral, rectal (e.g., via suppository or enema) or parenteral (e.g., intravenous, subcutaneous or intramuscular) route. In addition, the compositions may be incorporated into biodegradable polymers allowing for sustained release of the composition, the polymers being implanted in the vicinity of where delivery is desired, for example, in the intestinal epithelia. The biodegradable polymers and their use are described, for example, in detail in Brem et al. *J. Neurosurg.* 74:441-446 (1991).

Pharmaceutical compositions are administered in an amount, and with a frequency, that is effective to inhibit or alleviate the symptoms of a disease characterized by defective chloride transport, such as cystic fibrosis, asthma, chronic obstructive pulmonary disease, and other inflammatory disorders of the airways, intestinal constipation, pancreatitis, and dry eye syndrome, and/or to delay the progression of the disease. The effect of a treatment may be clinically determined by nasal potential difference measurements, or other measurements as described herein and known in the art. The precise dosage and duration of treatment may be determined empirically using known testing protocols or by testing the compositions in model systems known in the art and extrapolating therefrom. Dosages may also vary with the severity of the disease. A pharmaceutical composition is generally formulated and administered to exert a therapeutically useful effect while minimizing undesirable side effects. In general, an oral dose ranges from about 200 mg to about 2000 mg, which may be administered 1 to 3 times per day. Compositions administered as an aerosol are generally designed to provide a final concentration of about 10 to 50 µM at the airway surface, and may be administered 1 to 3 times per day. It will be apparent that, for any particular subject, specific dosage regimens may be adjusted over time according to the individual need.

As noted above, a pharmaceutical composition may be administered to a mammal to stimulate chloride transport, and to treat diseases characterized by defective chloride transport, such as cystic fibrosis, asthma, chronic obstructive pulmonary disease, and other inflammatory disorders of the airways, intestinal constipation, pancreatitis, and dry eye syndrome and diseases with excessive accumulation of mucus, including cystic fibrosis, chronic bronchitis and asthma and to prevent local vitamin C deficits in the respiratory tract due to oxidatative stress (ozone, tobacco smoke, air pollution, allergic reactions, and the like). Patients that may benefit from administration of a therapeutic compound as described herein are those afflicted with one or more diseases characterized by defective chloride transport, such as cystic fibrosis, asthma, chronic obstructive pulmonary disease, and other inflammatory disorders of the airways, intestinal constipation, pancreatitis, and dry eye syndrome and diseases with excessive accumulation of mucus, including cystic fibrosis, chronic bronchitis and asthma. Such patients may be identified based on standard criteria that are well known in the art, including the presence of abnormally high salt concentrations in the sweat test, the presence of high nasal potentials, or the presence of a cystic fibrosis-associated mutation.

Summary of Sequence Listing

SEQ ID NO:1 is a DNA sequence encoding human CFTR.
SEQ ID NO:2 is an amino acid sequence of human CFTR.
SEQ ID NO:3 is a DNA sequence encoding human CFTR with the ΔF508 mutation.
SEQ ID NO:4 is an amino acid sequence of human CFTR with the ΔF508 mutation.
SEQ ID NO:5 is a DNA sequence encoding human CFTR with the G551D mutation.
SEQ ID NO:6 is an amino acid sequence of human CFTR with the G551D mutation.
SEQ ID NOs:7-10 are PCR primers.
SEQ ID NO:11 is the polynucleotide of SVCT2 from human trachea epithelia as set forth in GenBank accession No. AY380556 and is identical to the sequence set forth in SEQ ID NO:12 with the exception of one nucleotide exchange at position 1807 T->C.
SEQ ID NO:12) is the polynucleotide of SVC2 from human kidney as set forth in GenBank accession No. AJ269478.

The following Examples are offered by way of illustration and not by way of limitation.

EXAMPLES

Example 1

Stimulation of Chloride Transport by Representative Flavones and Isoflavones in Airway Cells This Example illustrates the use of the representative compounds apigenin, quercetin and biochanin A to enhance chloride secretion in Calu-3 human pulmonary cultures or in primary bovine tracheal cultures.

A Calu-3 cell monolayer was prepared in an Ussing chamber as described by Illek et al., *Am. J. Physiol.* 270:C265-275, 1996. The basolateral membrane was permeabilized with α-toxin and a chloride gradient was applied across the apical membrane as a driving force (see Illek et al, *Am. J. Physiol.* 270:C265-C275, 1996). The tissue was first stimulated with cAMP (100 µM), and then with a representative flavone or isoflavone.

Figure 2:
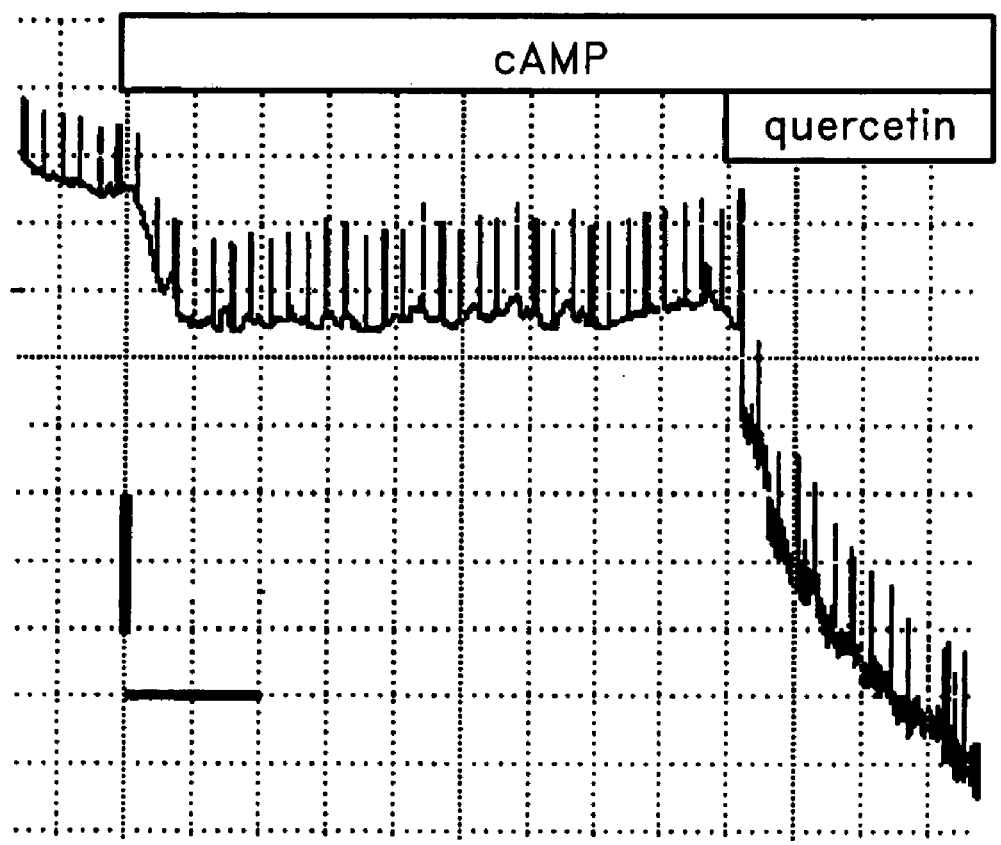
FIG. 2 is a recording showing the effect of quercetin on transepithelial short-circuit current across a Calu-3 cell monolayer in an Ussing chamber, where the basolateral membrane was permeabilized with α-toxin and a chloride gradient was applied across the apical membrane as a driving force. Tissue was first stimulated with cAMP (100 µM). Quercetin (30 µM) was subsequently added as indicated. Bars are 140 seconds (horizontal) and 12 µA/cm$^2$ (vertical).

As shown in FIGS. 1 and 2, subsequent addition of apigenin or quercetin further stimulated chloride current. FIG. 1 illustrates the short circuit current across the Calu-3 cell monolayer before and after addition of apigenin (50 µM). FIG. 2 illustrates the effect of quercetin (30 µM) on chloride current across a Calu-3 monolayer. In both cases, the flavone stimulated chloride current beyond the stimulation achieved by cAMP.

Figure 3:
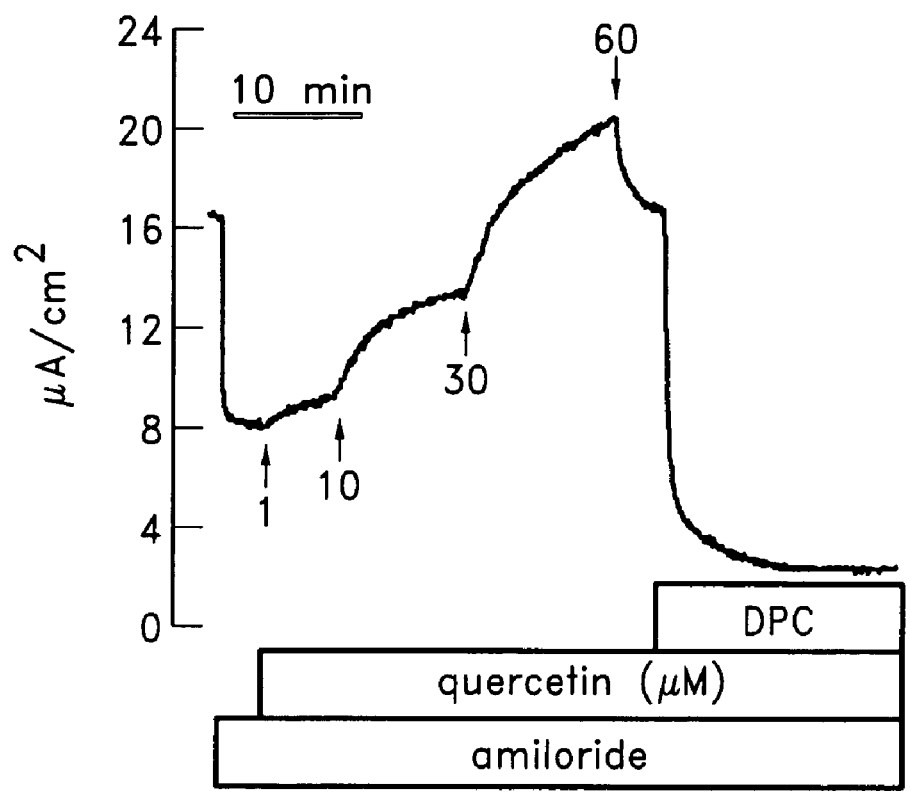
FIG. 3 is a recording illustrating the dose-dependent stimulation of transepithelial chloride secretion by quercetin (in the amounts indicated) across a primary bovine tracheal epithelium. Amiloride (50 µM) was added to block sodium transport as indicated. The CFTR channel blocker diphenylcarboxylate (DPC, 5 mM) was added as shown.

FIG. 3 illustrates the results of a related experiment to evaluate the dose-dependent stimulation of transepithelial chloride secretion by quercetin across a primary bovine tracheal epithelium. The epithelial cells were first treated with amiloride (50 µM), and then with quercetin at the indicated concentrations. The dose-response relation yielded a half maximal stimulation at 12.5 µM. At high concentrations of quercetin, the current was blocked. Current was fully inhibited by the CFTR channel blocker diphenylcarboxylate (DPC, 5 mM).

Figure 4:
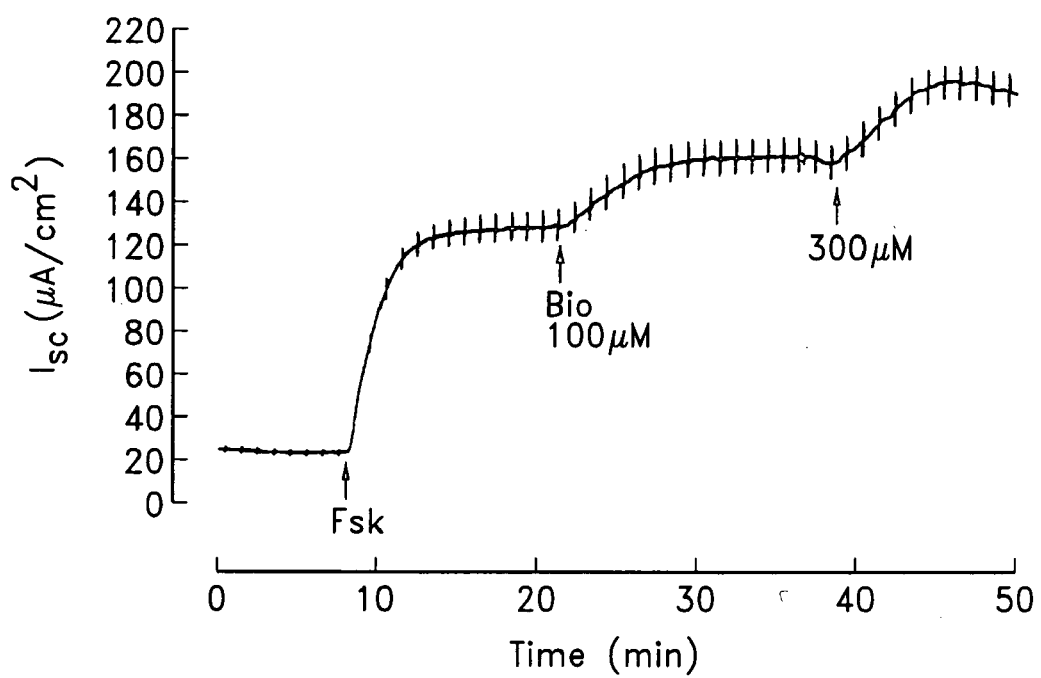
FIG. 4 is a recording showing the effect of biochanin A on transepithelial short-circuit current across a Calu-3 cell monolayer in an Ussing chamber, where the basolateral membrane was permeabilized with α-toxin and a chloride gradient was applied across the apical membrane as a driving force. The tissue was first stimulated with forskolin (Fsk, 10 µM). Subsequent addition of biochanin A (Bio, 100 and 300 µM) was subsequently added as indicated.

To evaluate the effect of biochanin A, a Calu-3 cell monolayer was prepared and permeabilized as described above. The tissue was first stimulated with forskolin (Fsk, 10 µM). The effect of biochanin A (Bio, 100 and 300 µM) on short-circuit current ($I_{sc}$) across the Calu-3 monolayer was evaluated in an Ussing chamber. As shown in FIG. 4, biochanin A further stimulated chloride secretion.

Example 2

Activation of Mutant CFTR by Representative Flavones and Isoflavones

This Example illustrates the use of the representative compounds apigenin, quercetin and genistein to activate ΔF508-CFTR and G551D-CFTR in different cell types.

Figure 5:
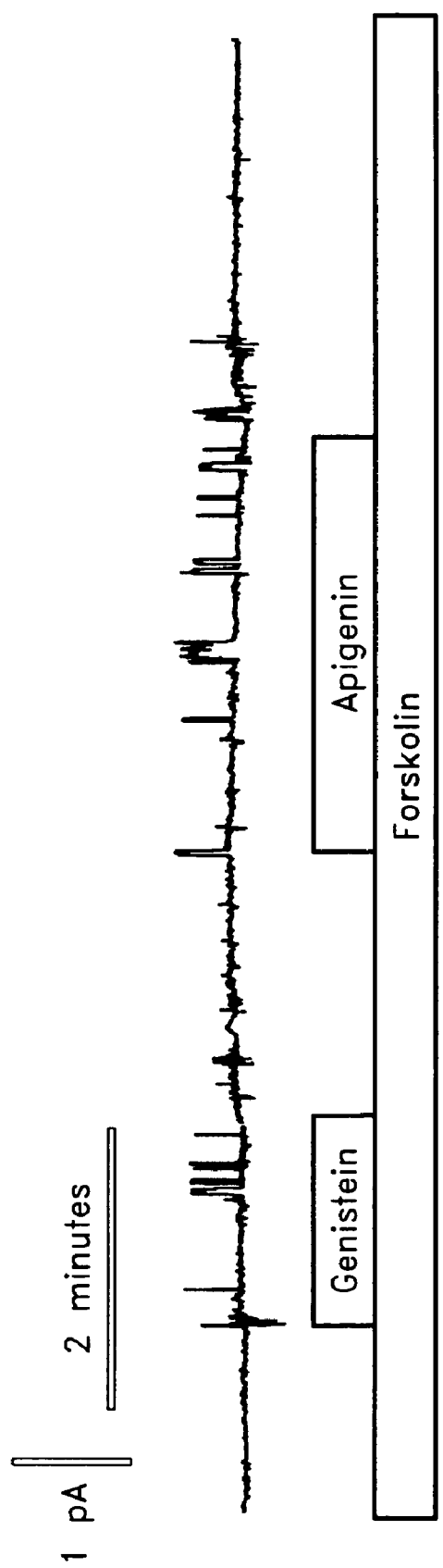
FIG. 5 is a cell-attached single channel patch clamp recording from a 3T3 cell expressing ΔF508-CFTR. The cell was treated with 10 µM forskolin as shown. Genistein (50 µM) and apigenin (50 μM), were added where indicated by boxes. The holding potential was 75 mV, and channel openings were upward.

A cell-attached single channel patch clamp recording was obtained from a 3T3 cell expressing ΔF508-CFTR as described by Hamill et al., *Pflugers Arch.* 391:85-100, 1981 and Fischer and Machen, *J. Gen. Physiol.* 104:541-566, 1994. As shown in FIG. 5, stimulation of the cell with 10 µM forskolin did not activate ΔF508-CFTR channel, but addition of genistein (50 µM) or apigenin (50 µM, where indicated by boxes) induced ΔF508-CFTR channel openings, and removal of these compounds inactivated the channels. The holding potential was 75 mV, and channel openings were upward.

Figure 6:
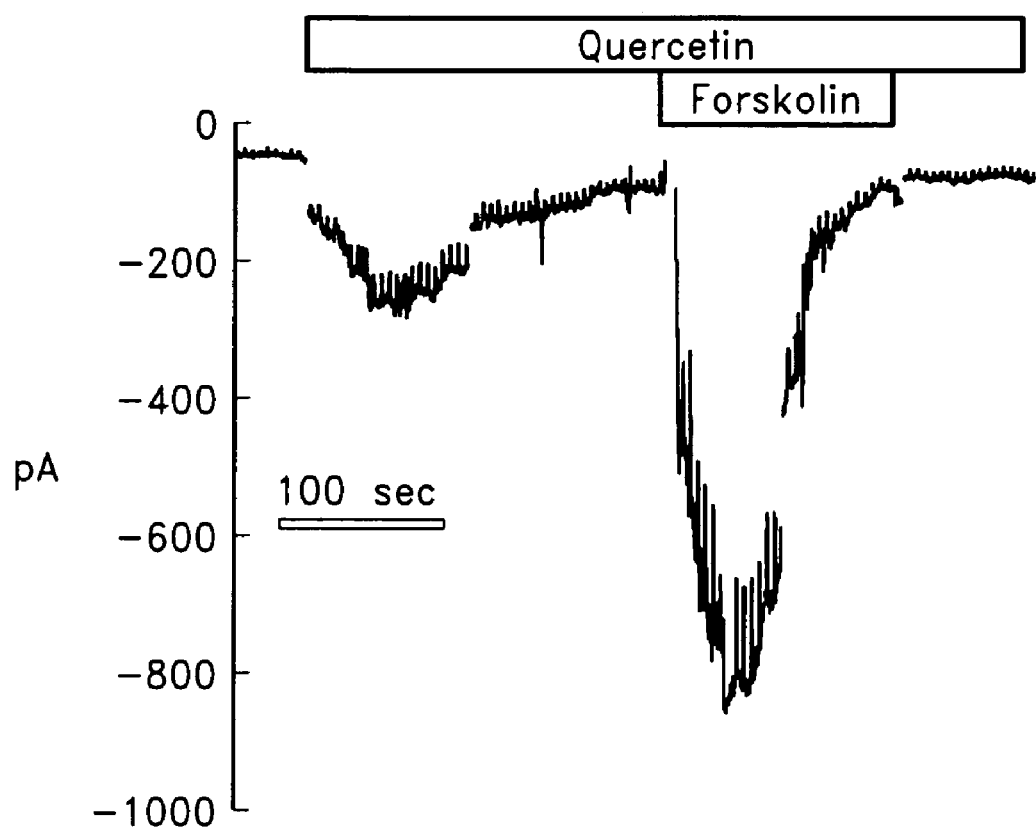
FIG. 6 is a whole cell patch clamp recording on an airway epithelial cell homozygous for ΔF508-CFTR. Before the measurement, the cell was incubated for 2 days in 5 mM 4-phenylbutyrate. 30 μM quercetin was added where indicated by the box. Further stimulation by forskolin (10 μM) is also shown. The holding potential was −60 mV.

FIG. 6 presents a whole cell patch clamp recording on an airway epithelial cell homozygous for ΔF508-CFTR (cell type: JME cell, see Jeffersen et al., *Am. J. Physiol.* 259:L496-L505, 1990). Before the measurement, the cell was incubated for 2 days in 5 mM 4-phenylbutyrate to enhance ΔF508-CFTR expression in the plasma membrane (Rubenstein & Zeitlin, *Ped. Pulm. Suppl.* 12:234, 1995). Measurements were performed as described by Fischer et al., *J. Physiol. Lond.* 489:745-754, 1995. Addition of 30 µM quercetin activated chloride current in the whole cell mode, which was further stimulated by forskolin. The holding potential was −60 mV.

Figure 7:
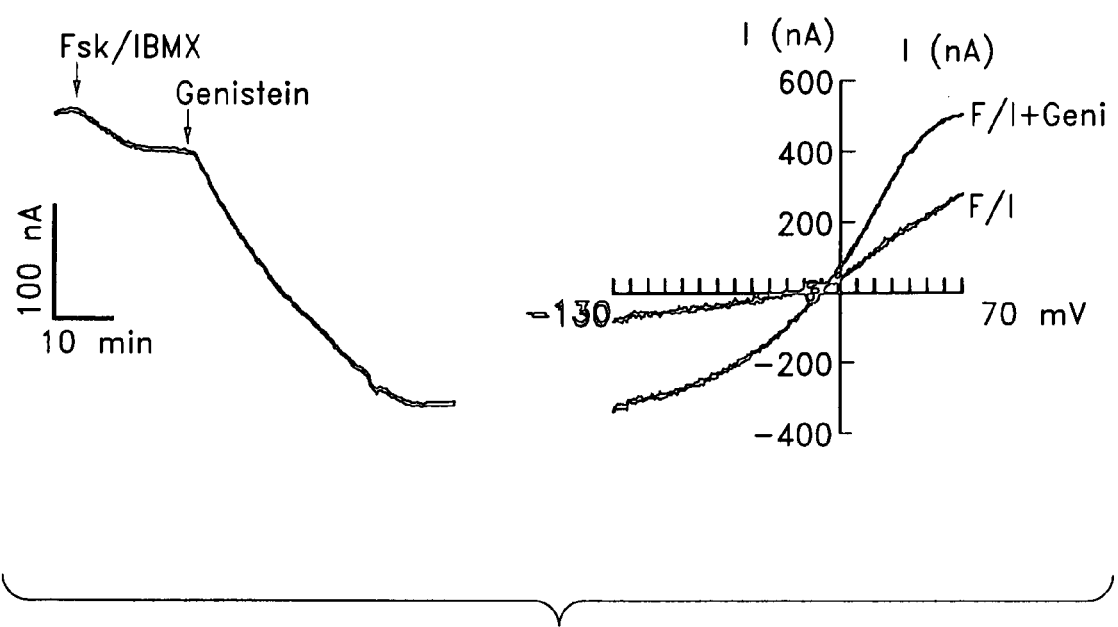
FIG. 7 is a recording illustrating the effect of genistein on G551D-CFTR expressed in a Xenopus oocyte. Current was measured with the two-electrode voltage clamp technique. G551D-CFTR was injected in oocyte. Current was first stimulated with forskolin (10 μM) and isobutylmethylxantine (IBMX; 2 mM). Genistein (50 μM) was added as indicated. The right panel shows current voltage relations recorded after treatment with forskolin and IBMX (F/I) and after treatment with genistein (F/I+Geni). A voltage ramp from −130 mV to +70 mV was applied and current was recorded during the two conditions.

The effect of genistein on chloride current in a Xenopus oocyte expressing G551D-CFTR was measured with the two-electrode voltage clamp technique (see Miledi et al., *Proc. R. Soc. Lond. Biol.* 218:481-484, 1983). G551D-CFTR (2 ng in 50 nL of water) was injected into the oocyte. Current was first stimulated with forskolin (10 µM) and isobutylmethylxantine (IBMX; 2 mM). Genistein (50 µM) was found to further activate chloride currents. As shown in FIG. 7, genistein increased conductance and shifted reversal potential to the right, which is indicative of a stimulated chloride current.

Example 3

Effect of Representative Flavones on Nasal Potential Difference

This Example illustrates the in vivo use of quercetin, apigenin and kaempferol to activate the nasal potential difference in humans and mice.

Figure 8:
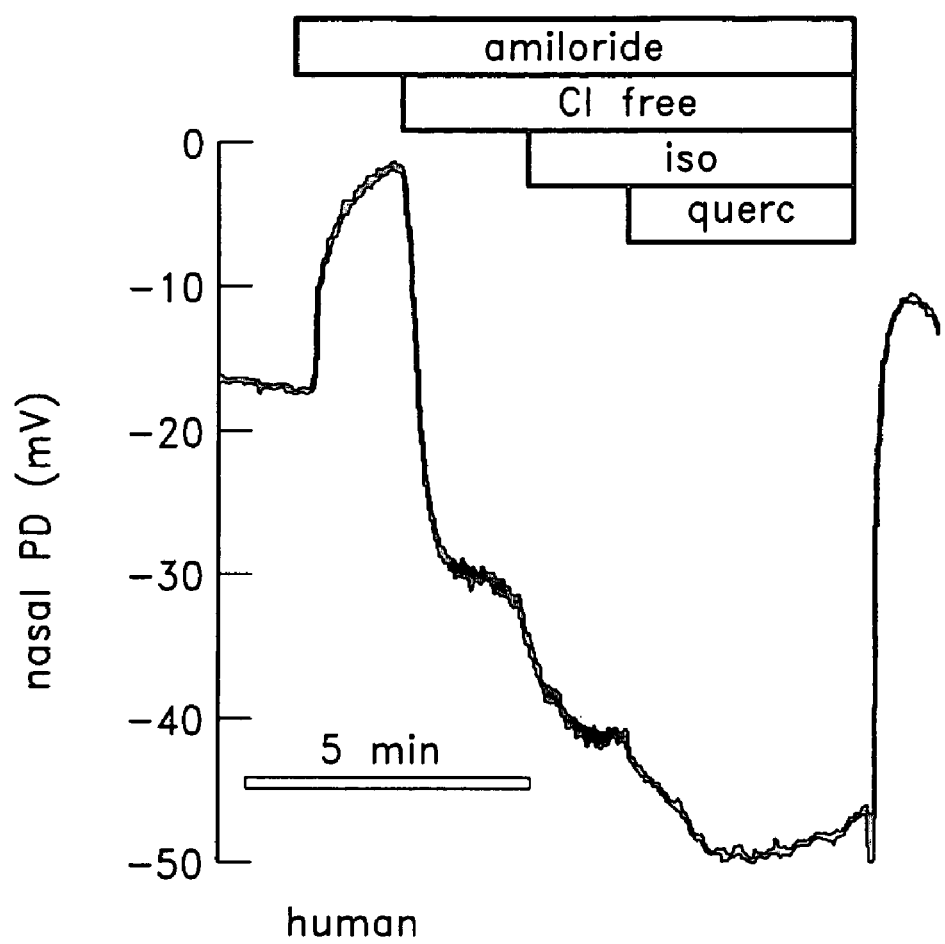
FIG. 8 is a recording illustrating the effect of quercetin on nasal potential difference (PD) measurement in a healthy human volunteer. Amiloride (50 μM) was added to block sodium transport as indicated. Conditions were rendered chloride free (Cl free) and chloride secretion was stimulated with isoproterenol (iso; 5 μM). Quercetin (querc; 10 μM) was added as indicated.
Figure 9:
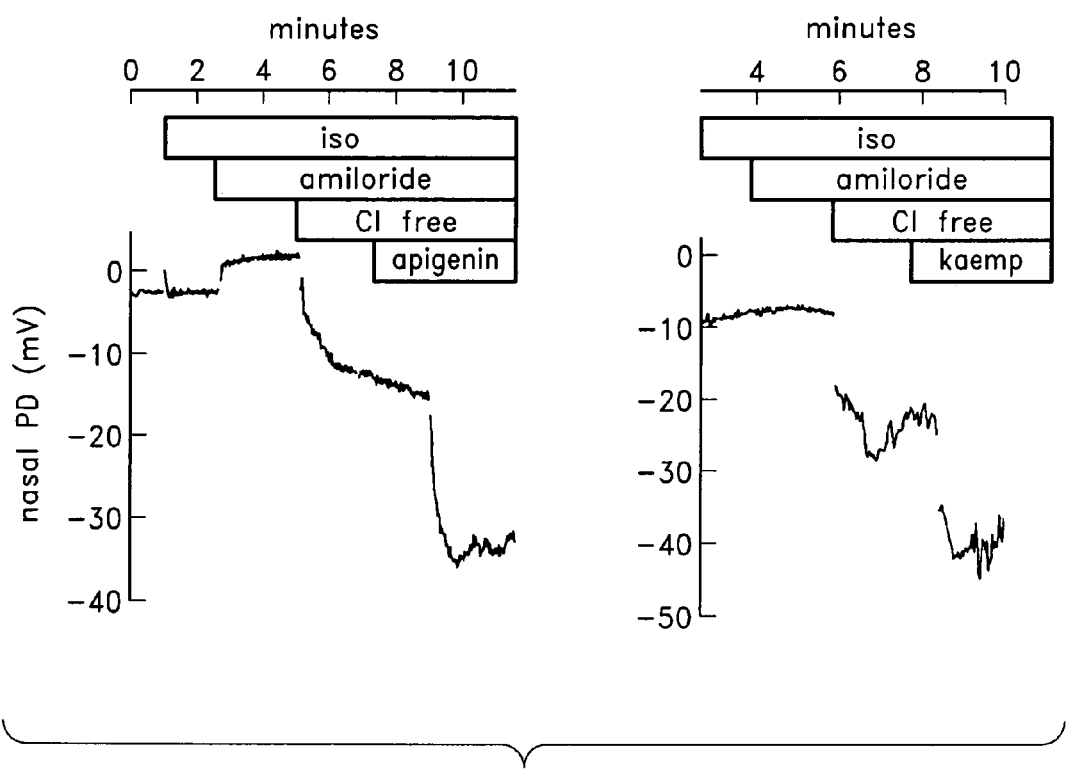
FIG. 9 is a recording illustrating the effect of apigenin and kaempferol on nasal PD in mice. Chloride secretion was stimulated with isoproterenol (iso; 5 μM), and amiloride (50 μM) was added to block sodium transport as indicated. Under chloride-free conditions (Cl free), apigenin (50 μM, left panel) and kaempferol (kaemp, 50 μM, right panel) were added as indicated.

The effect of quercetin on nasal potential difference (PD) measurement in a healthy human volunteer was measured as described by Knowles et al., *Hum. Gene Therapy* 6:445-455, 1995. Under conditions where sodium transport was blocked with amiloride (50 µM) and chloride secretion was stimulated under chloride-free conditions with isoproterenol (5 µM), quercetin (10 µM) stimulated nasal PD further (FIG. 8).

The effect of apigenin and kaempferol on nasal PD in mice was evaluated using a method similar to that employed for measurements in humans, except that a plastic tube of approximately 0.1 mm diameter was used as an exploring nasal electrode. The plastic tube was perfused with test solutions at approximately 10 µL/min. After blocking sodium transport with amiloride (50 µM) and during stimulation of chloride secretion with isoproterenol (iso;5 µM) under chloride-free conditions, apigenin (50 µM, left panel) and kaempferol (kaemp, 50 µM, right panel) further stimulated nasal PD.

These results show that the representative flavenoids quercetin, apigenin, kaempferol and biochanin A stimulate chloride transport across epithelial tissues derived from the airways in vitro, and across nasal epithelium in vivo. The results also show that the CFTR mutants ΔF508 and G551D can be activated by the representative compounds genistein and apigenin.

Example 4

Effect of Genistein on Chloride Current in Cells Expressing a Mutant CFTR

This Example illustrates the ability of the representative isoflavone genistein to activate chloride current in cells expressing a mutant CFTR.

Figure 10:
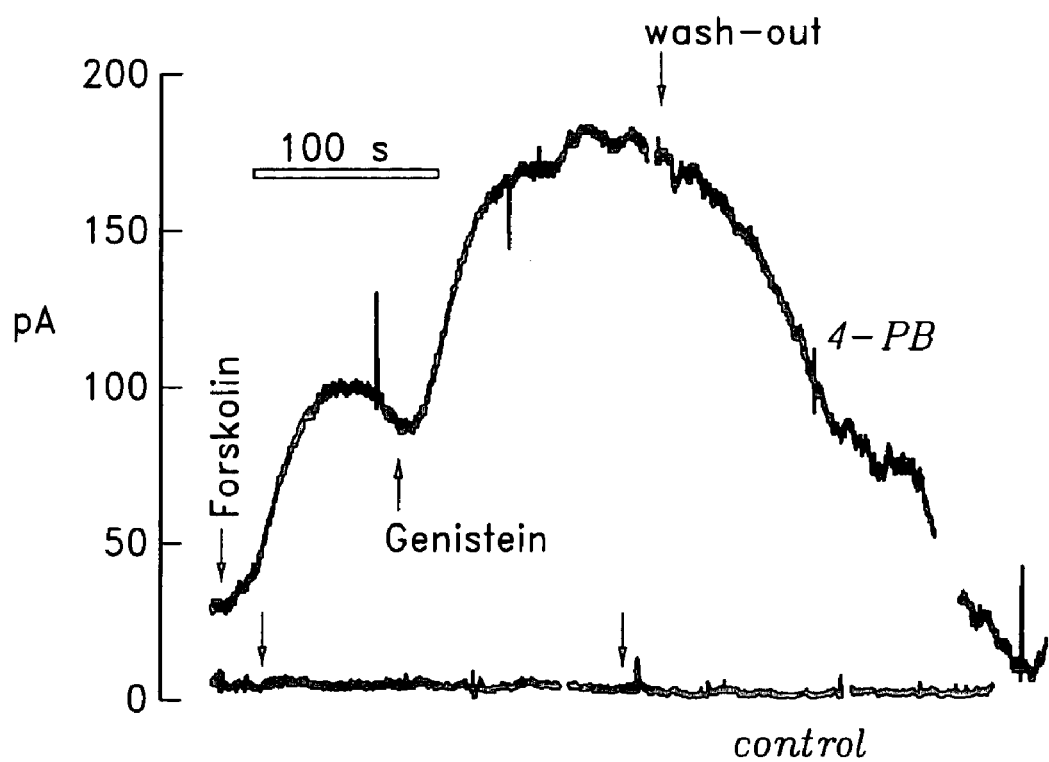
FIG. 10 is a recording illustrating the effect of genistein, with and without 4-phenylbutyrate, on chloride current in JME cells. The recording was performed at 0 mV holding potential with a 17:150 mM chloride gradient from bath to pipette. The bottom trace is from an untreated cell and the top trace is from a cell that had been incubated in 5 mM 4-phenylbutyrate (4-PB) for two days. Forskolin (10 μM) and genistein (30 μM) were added as indicated.

In one experiment, genistein was used in combination with 4-phenylbutyrate. Chloride current was measured in JME cells (human nasal epithelial cell line homozygous for the Δ508 mutation of CFTR; see Jefferson et al., *Am. J. Physiol.* 259:L496-505, 1990). The recording was performed at 0 mV holding potential with a 17:150 mM chloride gradient from bath to pipette. Under these conditions, the recorded current, shown in FIG. 10, is chloride current (Illek and Fischer, *Am. J. Physiol.* (*Lung Cell. Mol. Physiol.*):L902-910, 1998). The bottom trace in FIG. 10 is from an untreated cell. Neither forskolin (10 µM nor genistein (30 µM activated current. The top tracing in FIG. 10 is from a cell that had been incubated in 5 mM 4-phenylbutyrate (4-PB) for two days (Rubenstein et al., *J. Clin. Invest.* 100:2457-2465, 1997). After 4-PB treatment, chloride current was stimulated by forskolin (by on average 30.3±19.4 pS/pF, n=6), and further activated by genistein (to an average 105±84 pS/pF) in a CF cell with the Δ508-CFTR mutation. These results further demonstrate the ability of a flavenoid compound to optimize chloride currents elicited in CF cells by other means.

Figure 11A:
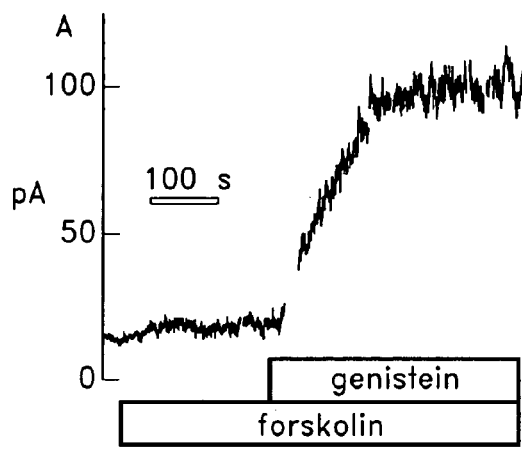
FIGS. 11A-11C are a whole cell patch clamp recording (FIG. 11A) and graphs (FIGS. 11B and 11C) illustrating the effect of forskolin and genistein on HeLa cells infected with a G551D-CFTR-containing adenovirus. Cells were stimulated with forskolin (10 μM) and genistein (30 μM), as indicated. The fit of the data with the Goldman equation is shown by the line in FIG. 11B. A current variance to mean current plot is shown in FIG. 11C.
Figure 11B:
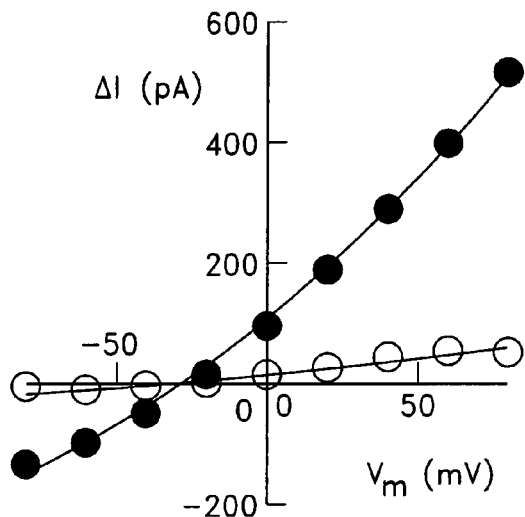
Figure 11C:
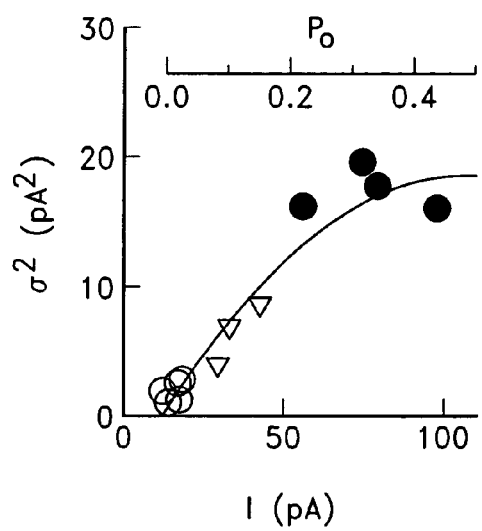

Within another experiment, HeLa cells infected with the G551D-CFTR-containing adenovirus were investigated in the patch clamp mode. Stimulation of the cell with forskolin (10 µM) stimulated only a very small current (FIGS. 11A and 11B). On average, forskolin-stimulated conductance was 9.5±5 pS/pF (n=4). Additional stimulation with genistein (30 µM) stimulated significant chloride currents, which were time- and voltage-independent (FIG. 11B) and well fitted with the Goldman equation (line in FIG. 11B; Illek and Fischer, *Am. J. Physiol.* (*Lung Cell. Mol. Physiol.*):L902-910, 1998), which are characteristics of CFTR-mediated currents. Average forskolin+genistein-activated conductance was 120±30 pS/pF (n=4). Current variance to mean current plot (FIG. 11C) were used to calculate the average open probability ($P_o$ shown on top of axis) of the population of channels carrying the total current (as described in Illek and Fischer, *Am. J. Physiol.* (*Lung Cell. Mol. Physiol.*):L902-910, 1998). During forskolin stimulation, maximal $P_o$ reached was 0.04 (open circles) and after additional stimulation with genistein $P_o$ reached a maximum of 0.42 in this recording. On average, after forskolin stimulation, $P_o$=0.05±0.02 and after forskolin+genistein stimulation $P_o$=0.54±0.12. For comparison, wild type CFTR expressed in HeLa cells and recorded under the same conditions resulted in $P_o$=0.36±0.05 (n=3) after forskolin stimulation and $P_o$=0.63±0.16 after forskolin+genistein treatment.

Example 5

Effect of Representative Flavones on Nasal Potential Difference in CF Patients

This Example illustrates the in vivo use of quercetin and genistein to activate the nasal potential difference in CF patients bearing the G551D mutation.

Figure 12A:
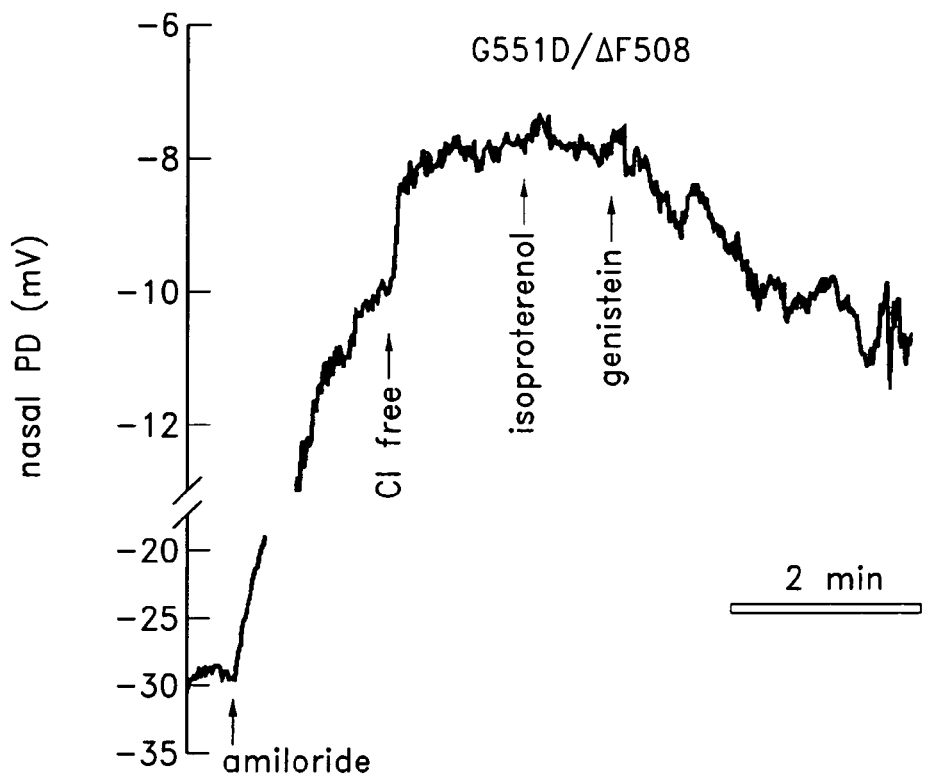
FIGS. 12A and 12B illustrate the use of representative flavonoids for the treatment of CF patients.
Figure 12B:
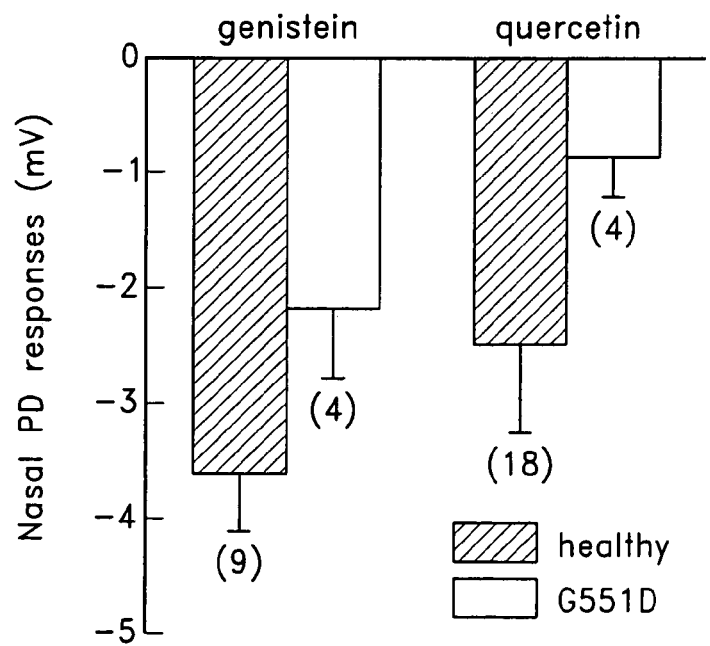

Measurements were performed on patients as described by Alton et al., *Eur. Respir. J.* 3:922-926, 1990; Illek and Fischer, *Am. J. Physiol.* (*Lung Cell. Mol. Physiol.*):L902-910, 1998; and Knowles et al., *Hum. Gene Therapy* 6:445-455, 1995). The results are presented in FIGS. 12A and 12B. FIG. 12A shows a recording from a patient with the genotype G551D/ΔF508. Initial treatment with amiloride and chloride free solution had the purpose to isolate and amplify the chloride selective potentials. Addition of the beta-adrenergic agonist isoproterenol showed no effect, which is typical for CF patients (Knowles et al., *Hum. Gene Therapy* 6:445-455, 1995). However, addition of genistein hyperpolarized nasal PD. Average responses of nasal PD to genistein and quercetin of four CF patients with the G551D mutation are shown in FIG. 12B (open bars). The filled bars show for comparison the respective responses in healthy subjects. The genotypes of the 4 CF patients were: two G551D/ΔF508, one G551D/G551D and one G551D/unknown. Responses are most likely due to the G551D mutation because the homozygous G551D patient responded not different compared to the heterozygous G551D patients. Genistein and quercetin responses of nasal PD in CF patients were significant (p<0.05).

These results demonstrate that CFTR mutations are sensitive to flavenoid treatment, and provide additional evidence for therapeutic benefit of such compounds for the treatment of cystic fibrosis.

Example 6

Effect of Additional Representative Polyphenolic Compounds on Epithelial Cell Chloride Currents This Example illustrates the effect of further flavenoids and isoflavenoids on chloride currents in airway epithelial cells.

Figure 13A:
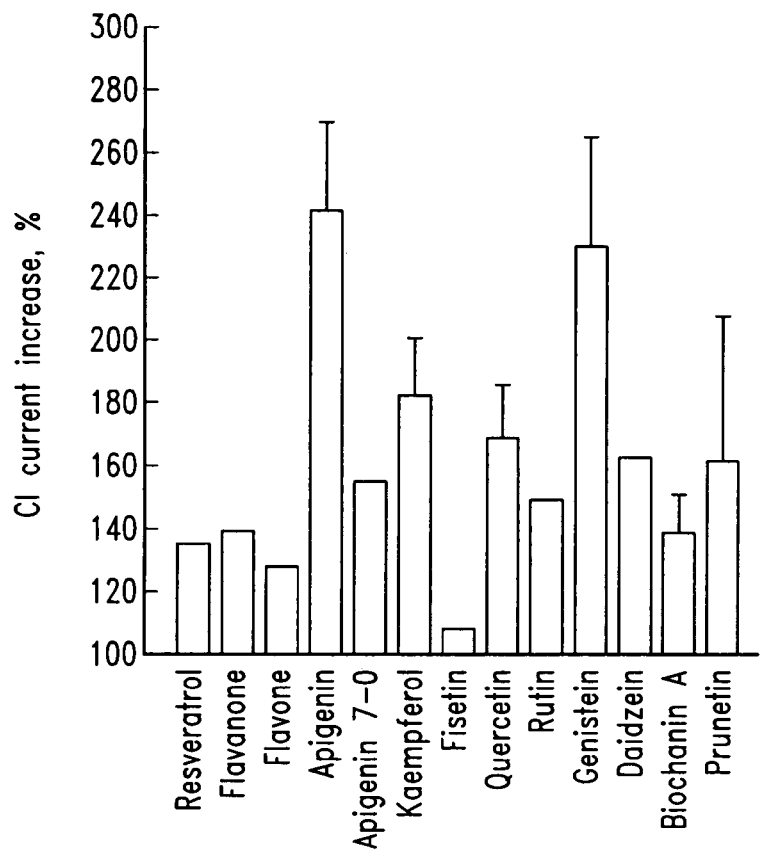
FIGS. 13A-13C illustrate the effect of additional representative flavonoids and isoflavonoids on chloride current in epithelial cells.

Airway epithelial cells were prestimulated with 10 µM forskolin. The percent increase in chloride current was then determined following treatment with a series of polyphenolic compounds. FIG. 13A summarizes the stimulatory effect of these compounds. On average, chloride currents were further stimulated by resveratrol (100 µM) to 135%, by flavanone (100 µM) to 140%, by flavone (200 µM) to 128%, by apigenin (20 µM) to 241%, by apigenin 7-O-neohesperidoside (30 µM) to 155%, by kaempferol (20 µM) to 182%, by fisetin (100 µM) to 108%, by quercetin (30 µM) to 169%, by rutin (30 µM) to 149%, by genistein (30 µM) to 229%, by daidzein (50 µM) to 162%, by biochanin A (100 µM) to 139% and by prunetin (100 µM) to 161%.

Figure 13B:
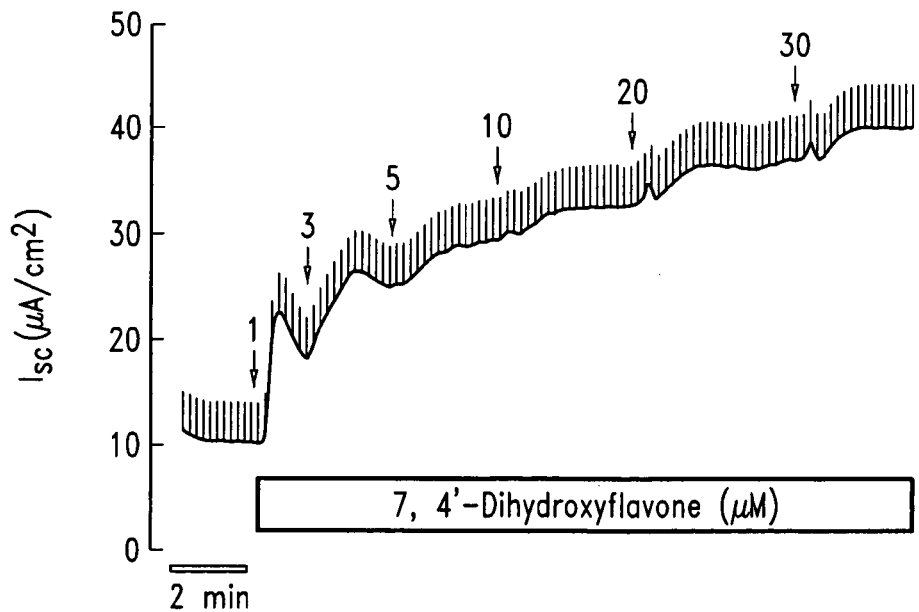

The stimulatory effect of 7,4' Dihydroxyflavone is shown in FIG. 13B. Addition of 7,4'-Dihydroxyflavone to the mucosal perfusion dose-dependently stimulated transepithelial Cl currents in unstimulated Calu-3 monolayers. This experiment was performed using unstimulated tissue.

Figure 13C:
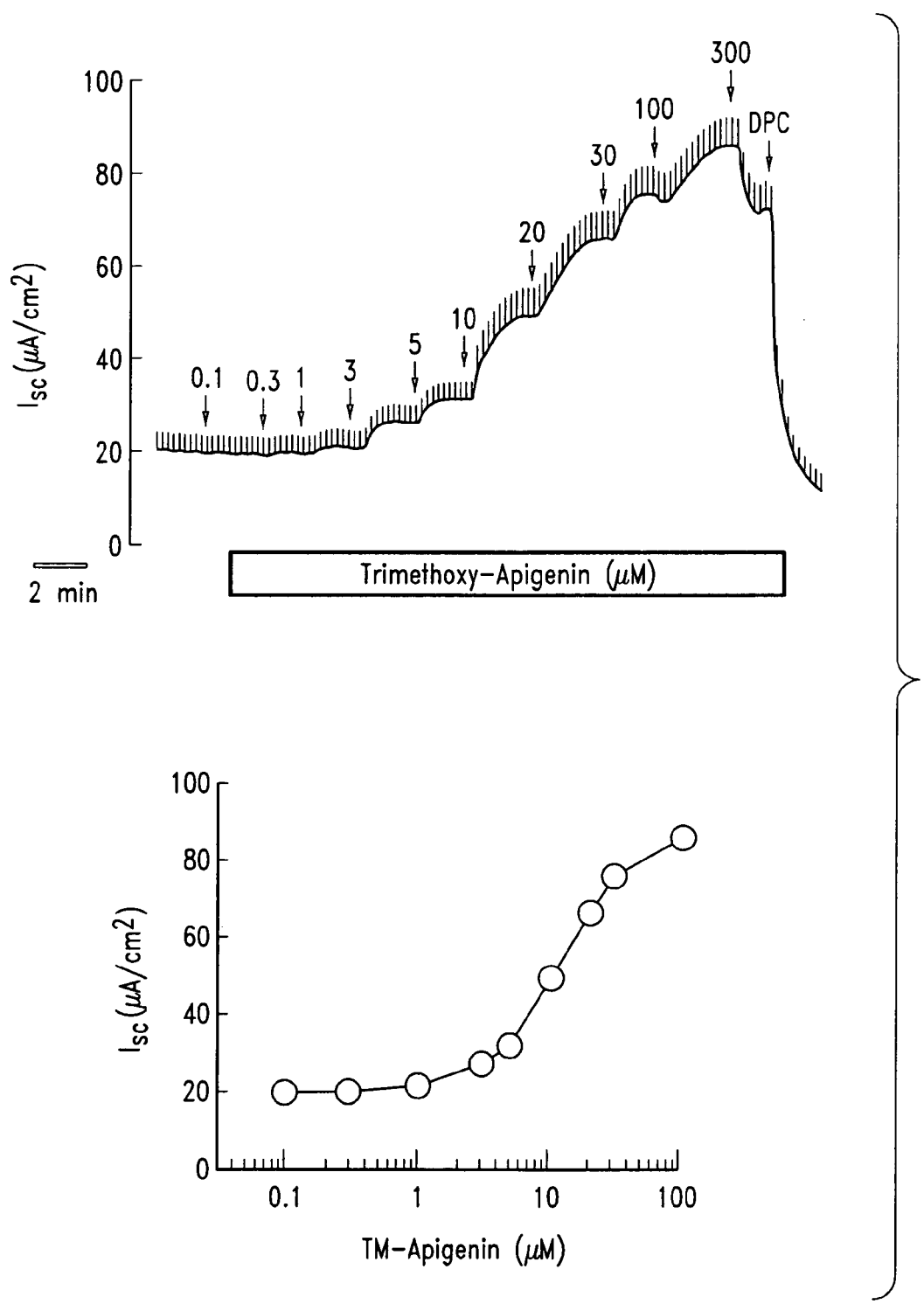

The stimulatory effect of trimethoxy-apigenin is shown in FIG. 13C. Addition of trimethoxy-apigenin to the mucosal perfusion dose-dependently stimulated transepithelial Cl currents in unstimulated Calu-3 monolayers. Kinetic analysis is depicted on the right panel and estimated half maximal stimulatory dose was 11.7 µM.

These results indicate that a variety of polyphenolic compounds stimulate chloride currents in epithelial cells.

Example 7

Effect of Resveratrol on Chloride Currents

This Example illustrates the stimulatory effect of resveratrol on transepithelial chloride currents.

Figure 14:
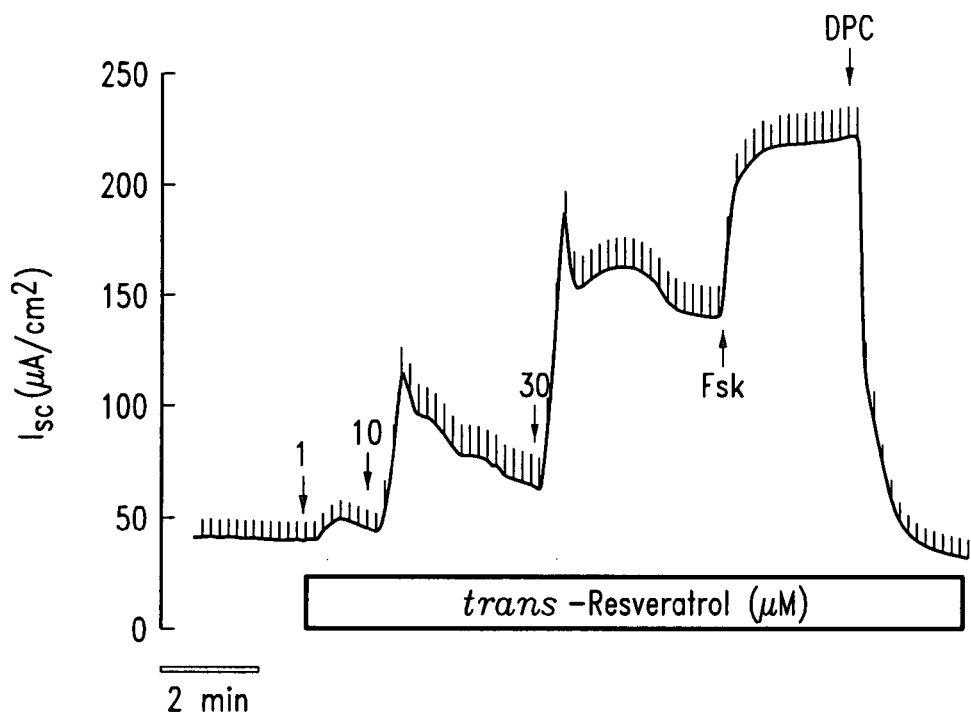
FIG. 14 is a recording illustrating the dose-dependent stimulation of transepithelial short-circuit current (Isc) across Calu-3 monolayers by resveratrol. Increasing concentrations of resveratrol (as indicated in μM) were added to the mucosal perfusion and dose-dependently increased chloride currents. For comparison, currents were further stimulated by serosal addition of 20 μM forskolin. Stimulated chloride current was completely blocked by addition of the chloride channel blocker DPC (5 mM). Currents were recorded with a serosal-to-mucosal chloride gradient at 0 mV and pulses were obtained at 2 mV.

Unstimulated Calu-3 monolayers were treated with increasing concentrations of resveratrol. FIG. 14 shows the recording generated following the addition of resveratrol to the mucosal perfusion dose-dependently stimulated transepithelial chloride currents in unstimulated Calu-3 monolayers. For comparison, currents were further stimulated by serosal addition of forskolin. The stimulated chloride current was completely blocked by the Cl channel blocker DPC. These results indicate that resveratrol stimulates transepithelial chloride transport.

Example 8

Effect of Ascorbic Acid and Dehydroascorbic Acid on Chloride Currents

This Example illustrates the stimulatory effect of ascorbic acid and dehydroascorbic acid on transepithelial chloride current.

Figure 15:
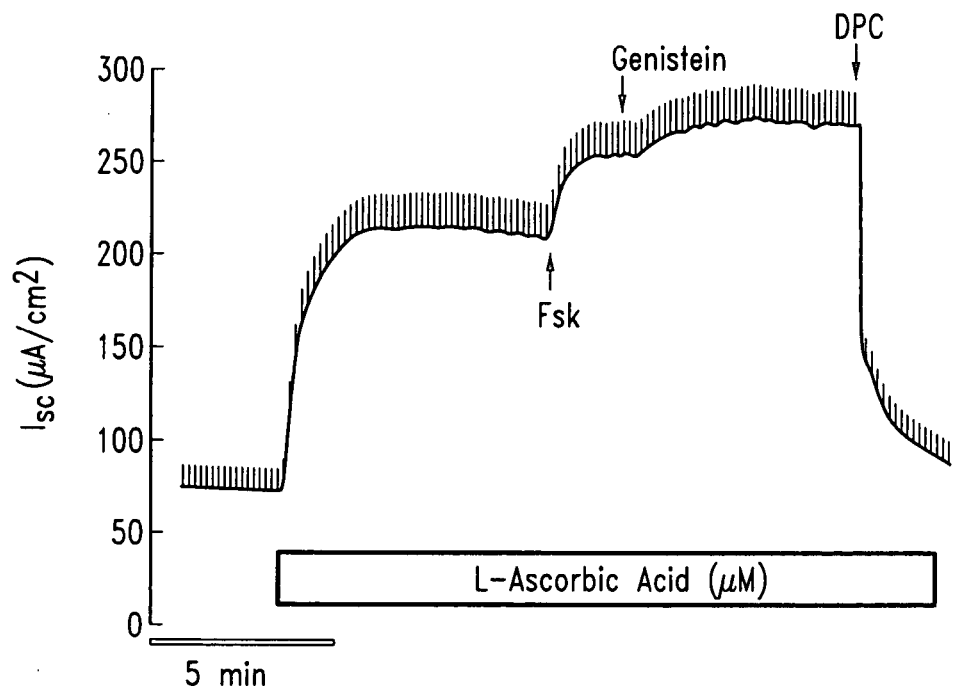
FIG. 15 is a recording showing L-ascorbic acid and genistein stimulation of transepithelial short-circuit current (Isc) across Calu-3 monolayers. Ascorbic acid (100 μM) was added as indicated. For comparison, ascorbic acid-stimulated chloride current was subsequently stimulated by the cAMP elevating agonist forskolin (20 μM, serosal). The CFTR activator genistein (20 mM) was then added to the mucosal perfusion as indicated. Stimulated current was completely blocked by addition of the chloride channel blocker DPC (5 mM), added as indicated. Currents were recorded with a serosal-to-mucosal chloride gradient at 0 mV and pulses were obtained at 2 mV.

Unstimulated Calu-3 monolayers were stimulated with L-ascorbic acid, as shown in FIG. 15. Addition of L-ascorbic acid to the mucosal or serosal perfusion very effectively stimulated transepithelial chloride secretion in unstimulated Calu-3 monolayers. For comparison, chloride currents were further stimulated by serosal addition of forskolin. In the continued presence of L-ascorbic acid and forskolin, it is remarkable that addition of genistein further stimulated chloride currents. These results indicate that genistein serves as a potent drug that is able to hyperstimulate chloride secretion and thereby maximize chloride transport across epithelia. The stimulated chloride current was completely blocked by the chloride channel blocker DPC.

Figure 16:
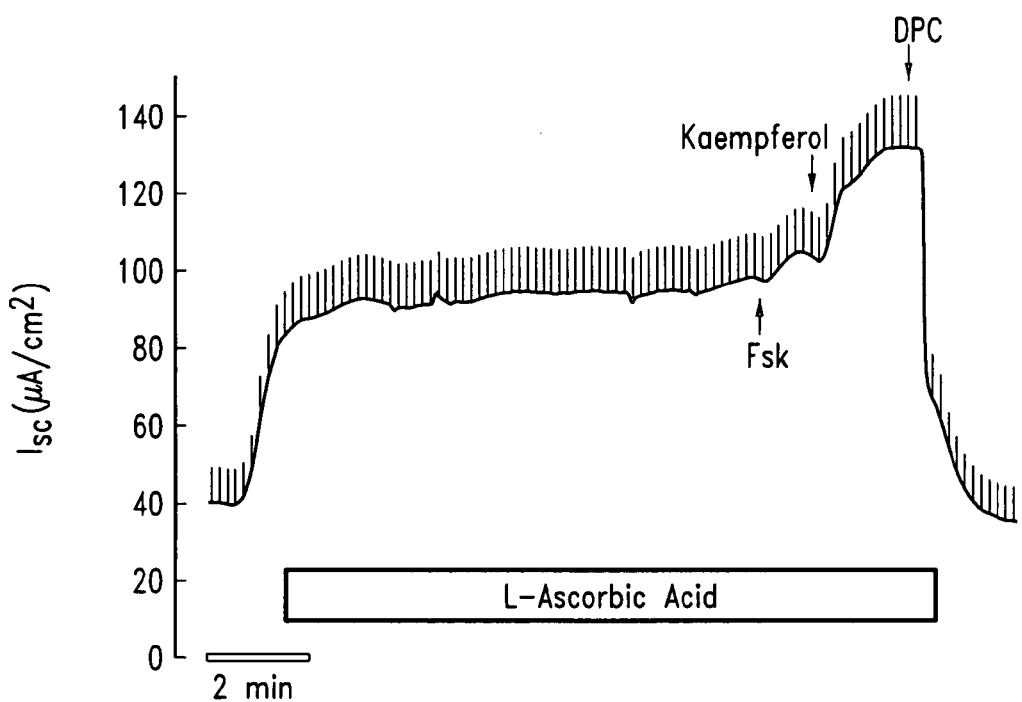
FIG. 16 is a recording showing L-Ascorbic acid and kaempferol stimulation of transepithelial short-circuit current (Isc) across Calu-3 monolayers. 100 μM ascorbic acid and forskolin (fsk, 20 μM, serosal) were added as indicated. The CFTR activator kaempferol (20 μM) was subsequently added, as indicated. Stimulated current was completely blocked by addition of the chloride channel blocker DPC (5 mM). Currents were recorded with a serosal-to-mucosal chloride gradient at 0 mV and pulses were obtained at 2 mV.

The stimulatory effect of L-ascorbic acid is also shown in FIG. 16. Addition of 100 µM L-ascorbic acid to the mucosal or serosal perfusion very effectively stimulated transepithelial chloride currents in unstimulated Calu-3 monolayers. For comparison, ascorbic acid-stimulated chloride currents were stimulated by the cAMP elevating agonist forskolin (20 µM, serosal). Under these stimulated conditions kaempferol further hyperstimulated chloride currents. The stimulated chloride current was completely blocked by the chloride channel blocker DPC (5 mM).

Figure 18:
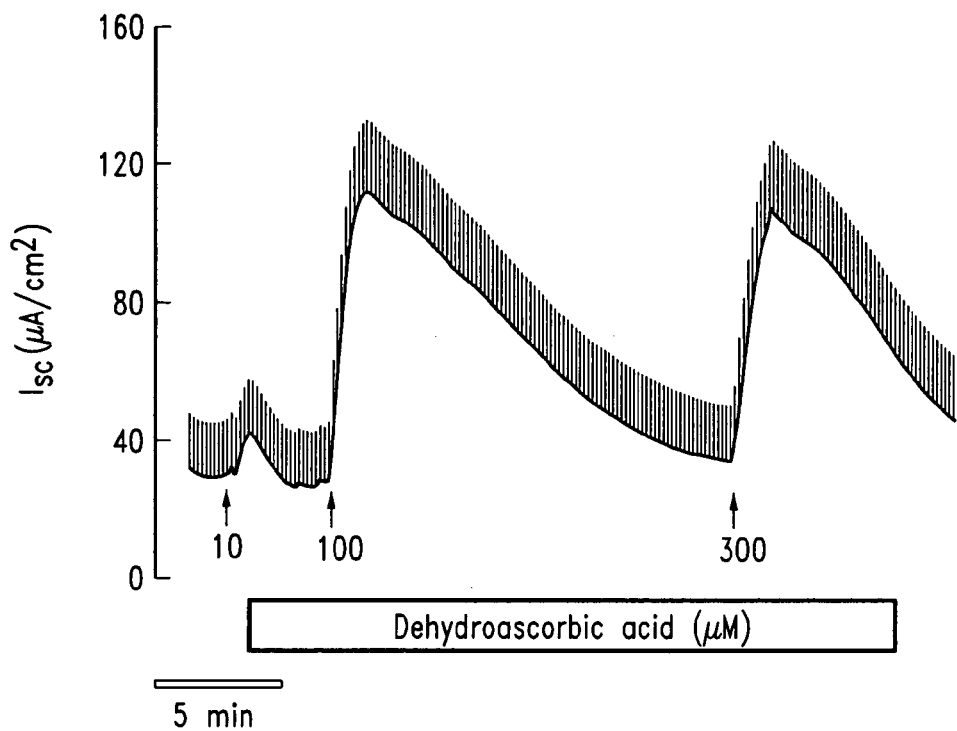
FIG. 18 is a recording illustrating the stimulation of transepithelial short-circuit current (Isc) across Calu-3 monolayers by addition of 10, 100 and 300 μM dehydroascorbic acid. Currents were recorded with a serosal-to-mucosal chloride gradient at 0 mV and pulses were obtained at 2 mV.

The stimulatory effect of dehydroascorbic acid is shown in FIG. 18. Addition of dehydroascorbic acid at 10, 100 or 300 µM to the mucosal and serosal perfusion effectively stimulated transepithelial chloride currents in unstimulated Calu-3 monolayers. Stimulated Cl currents returned to baseline after 5-15 min.

Example 9

Effect of Ascorbic Acid on Chloride Currents in vivo

This Example illustrates the stimulatory effect of ascorbic acid on human nasal potential difference.

Figure 17:
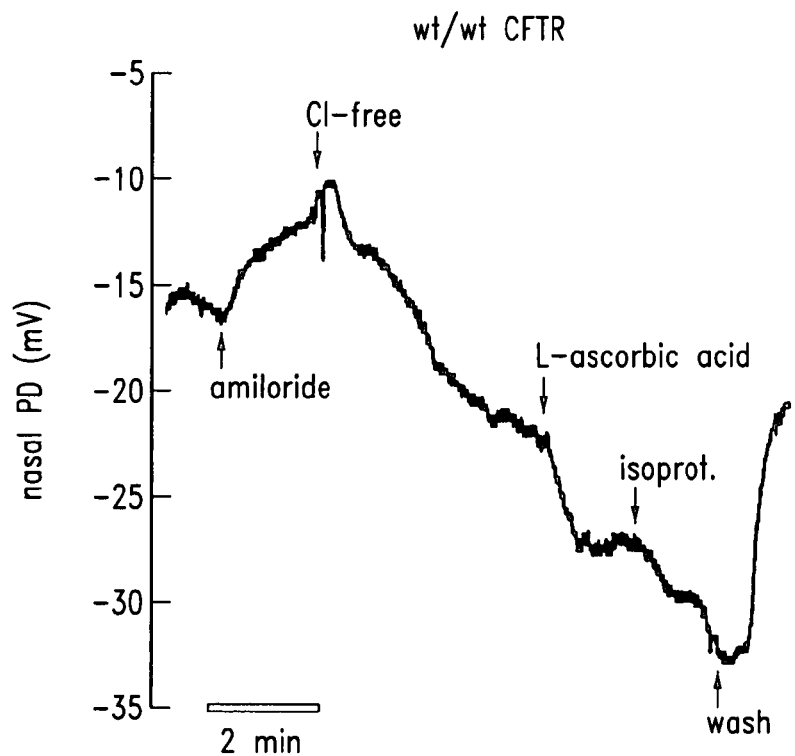
FIG. 17 is a recording illustrating the effect of L-ascorbic acid on nasal potential difference in human subjects. Amiloride, chloride-free solution and L-ascorbic acid (100 μM) were added to the luminal perfusate in the nose, as indicated. The β-adrenergic agonist isoproterenol was also added as indicated. Stimulation was reversed by washing out drugs with NaCl Ringer solution.

Nasal potential difference measurement was performed on a human volunteer according to a protocol by Knowles et al., Hum. Gene Therapy 6:445-455, 1995. Addition of L-ascorbic acid (100 µM) to the luminal perfusate in the nose (in the presence of amiloride (blocks Na currents) and in chloride-free solution) hyperpolarized nasal potential difference (PD) by 6.3 mV (FIG. 17). Addition of the β-adrenergic agonist isoproterenol further hyperpolarized nasal PD. Stimulation was reversed by washing out drugs with NaCl Ringer solution. These results demonstrate the ability of ascorbic acid to stimulate chloride transport in epithelia in humans.

Example 10

Effect of Genistein on Chloride Currents in Mammary Epithelia

This Example illustrates the stimulatory effect of genistein in mammary epithelial cells.

Figure 19:
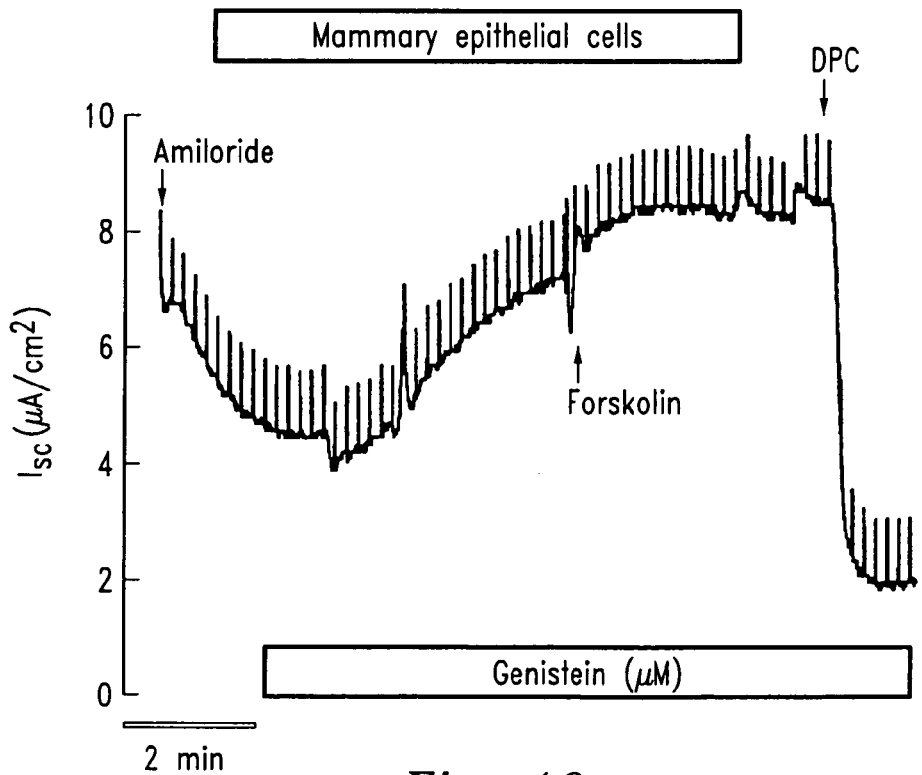
FIG. 19 is a recording illustrating the stimulatory effect of 20 μM genistein on transepithelial short-circuit current (Isc) across 31EG4 mammary epithelial monolayers. Na currents were blocked by mucosal addition of amiloride (10 mM), and chloride currents were further stimulated by forskolin (20 μM, serosal), as indicated. Currents were recorded in symmetrical NaCl Ringers solution at 0 mV and pulses were obtained at 2 mV.

The stimulation of transepithelial short-circuit current (Isc) across 31EG4 mammary epithelial monolayers by addition of 20 µM genistein is shown in FIG. 19. Na currents were blocked by mucosal addition of amiloride (10 mM). Chloride currents were further stimulated by forskolin (20 µM, serosal). Currents were recorded in symmetrical NaCl Ringers solution at 0 mV and pulses were obtained at 2 mV.

The following Methods were used for the experiments described in Examples 11-16.

Human airway cell culture. The human submucosal serous gland-like cell line Calu-3, the CF nasal epithelial cell line homozygous for ΔF508 CFTR (CF15) and human tracheal primary cultures (hTE) were cultured as described (Jefferson, D. M., Valentich, J. D., Marini, F. C., Grubman, S. A., Iannuzzi, M. C., Dorkin, H. L., Li, M., Klinger, K. W. & Welsh, M. J. (1990) Am. J. Physiol. 259, L496-L505. Sachs, L. A., Finkbeiner, W. E. & Widdicombe, J. H. (2003) In Vitro Cell Dev. Biol. Anim. 39, 56-62.). Wildtype CFTR-corrected CF15 cells were generated via adenovirus-mediated gene transfer. Growth media were nominally free of ascorbic acid (<10 µm, University Pathology Inc., Salt Lake City, Utah). For transepithelial measurements cells were grown on permeable filter inserts and used after 3 to 10 days.

Patch clamp analysis. Single channel patch clamp studies were performed on Calu-3 cells at 37° C. The outside-out recording mode was established via the whole cell mode as described (Fischer, H. (2001) in Methods in Molecular Medicine, eds. Skatch, W. R. & Walker, J. M. (Humana Press Inc, Totowa), pp. 49-66.). The bath solution contained (in mM) 145 NaCl, 1.7 $CaCl_2$, 1 $MgCl_2$, 10 Hepes, 10 glucose, pH=7.4. The pipette solution contained (in mM): 15 N-methyl-D-glucamine (NMG) Cl, 10 EGTA, 1 $MgCl_2$, 10 Hepes, 10 glucose, 120 NMG-gluconate, 5 MgATP, 0.1 LiGTP, pH=7.4. Open probabilities ($P_o$) for multi-channel recordings were calculated for consecutive 20-sec records with $P_o=(I-I_{base})/(N \cdot i)$, where I is the average current of the respective record, $I_{base}$ is the closed-level current, N is the maximal number of channel levels observed in the total recording, and i is the single channel current.

Cyclic AMP measurements. Confluent Calu-3 cells were exposed to L-ascorbic acid or forskolin for 15 min and lysed with 0.1 M HCl. Cellular cAMP levels were measured in non-acetylated samples using a competitive immunoassay for cAMP (R&D systems, Minneapolis, Minn.).

Short-circuit current measurement. Calu-3 or CF15 cells were grown as monolayers, mounted in Ussing chambers and short-circuit current ($I_{sc}$) was recorded as described (Illek, B. & Fischer, H. (1998) *Am. J. Physiol.* 275, L902-L910). At 20-50 second intervals, transepithelial voltage was clamped from zero to 2 mV and the transepithelial resistance ($R_{te}$) was calculated. A serosa-to-mucosa-directed Cl gradient was applied. Serosal Ussing chamber solution contained (in mM): 120 NaCl, 20 NaHCO$_3$, 5 KHCO$_3$, 1.2 NaH$_2$PO$_4$, 5.6 glucose, 2.5 CaCl$_2$, 1.2 MgCl$_2$. In mucosal Ussing chamber solutions, all Cl salts were exchanged for gluconate salts.

Nasal potential difference (NPD) measurements. Measurements of NPD were performed in healthy volunteers as described (Illek, B. & Fischer, H., Supra). The study protocol was approved by the Internal Review Board at Children's Hospital Oakland. Solutions and test drugs were perfused into one nostril at ~5 ml/min at room temperature (23-25° C.). NaCl solution contained (in mM): 145 NaCl, 4 KCl, 1 CaCl$_2$, 1 MgCl$_2$, 10 Hepes, pH=7.4. In Cl free solutions all Cl salts were replaced by the respective gluconate salts. All solutions were sterile filtered before use. NPD was sensed with an Ag/AgCl/agar electrode placed in the perfusing tube with respect to an electrode placed on a slightly scratched skin part on the forearm (Alton, E. W. F. W., Currie, A. D., Logan-Sinclair, R., Warner, J. O., Hodson, M. E. & Geddes, D. M. (1990) *Eur. Resp. J.* 3, 922-926).

CF mice and rectal potential difference (RPD) measurements. Gene-targeted mice homozyggus for the ΔF508 mutation (C57Bl6/J) received Golytely® (Braintree Laboratories, Inc.), a diarrhetic supplement, in the drinking water to increase their lifespan (Clarke, L. L., Gawenis, L. R., Franklin, C. L. & Harline, M. C. (1996) *Lab. Anim. Sci.* 46, 612-8). To correct the maturation defect of ΔF508 CFTR we used the chemical chaperone trimethylamine oxide (TMAO) (Brown, C. R., Hong-Brown, L. Q., Biwersi, J., Verkman, A. S. & Welch, W. J. (1996) *Cell Stress Chaperones* 1, 117-25). CF mice were injected with 4 mg/g TMAO from a 4 M stock solution every 8 hours for 24 hours, which is a regimen to partially correct the ΔF508 defect in CF mice (Fischer, H., Barbry, P., Illek, B., Sartori, C., Fukuda, N. & Matthay, M. A. (2001) *Am. J. Physiol.* 281, L52-L57). Controls were water-injected. The RPD assay was performed on mice that were anesthetized with 0.1 mg/g body weight ketamine and 0.01 mg/g body weight azepromazine. RPD was sensed with a 1 M NaCl agar bridge inserted ~1 cm into the rectum vs. a subcutaneous needle filled with 1 M NaCl. Measurements were performed in Cl free solution containing 100 μm amiloride and 5 mM Ba(OH)$_2$ to isolate the Cl-selective RPD.

RT-PCR analysis and cloning of SVCT2. Total RNA was isolated from airway cultures grown on permeable filter inserts using the RNeasy Mini Kit (Qiagen, Oslo, Norway). All samples were treated with DNase (2 U DNase, Promega) and RNase inhibitor (100 U Superase-In, Ambion Inc.). RT-PCR was performed using Superscript II RNase Reverse Transcriptase (Invitrogen) and 2.5 μm random hexamer primers (Applied Biosystems). First strand cDNA was used as a template in polymerase chain reactions (RedTaq DNA Polymerase, Sigma). The primer sequences for SVCT1 (103 bp) were forward: 5'-TTC TGG TTG TGC TGC TGA CC-3' (SEQ ID NO:7); reverse: 5'-TGT ATC AGA CCA CGC TCC TCT-3' (SEQ ID NO:8). For SVCT2 (97 bp) the sequences were: forward: 5'-GCT GTT GCA CAC AGA ACA CA-3' (SEQ ID NO:9); reverse: 5'-GAG GAG GCC GAT GAC TAC TTC-3' (SEQ ID NO:10). Standard PCR was performed using 30 cycles and annealing at 60° C. The cDNA coding for the open reading frame of SVCT2 was PCR-amplified from hTE and was cloned in-frame into the XhoI and EcoRI restriction sites of the enhanced green fluorescent expression vector pEGFP/N1 (Clontech). This construct was transfected into CF15 cells.

Confocal Microscopy. The expression of SVCT2-EGFP fusion proteins was assayed in filter-grown monolayers by confocal microscopy. Confluent CF15 monolayers were fixed with 2% paraformaldehyde and immunostained for the tight junction protein ZO-1 as a marker of the apical region using an anti-ZO-1 antibody (BD Bioscience) and Alexa Fluor 546-conjugated secondary antibody (Molecular Probes). Monolayers were embedded in Crystal Mount (Biomedia) and observed with a 63×/1.4 NA oil-immersion objective. A 3-dimensional image was produced from a stack of Z sections at 1.1 μm intervals. Image stacks were deconvolved and visualized using Huygens Professional Software by Scientific Volume Imaging (www.svi.nl).

Example 11

Vitamin C Activates CFTR Chloride Channels

The regulatory role of vitamin C on Cl ion channel activity was studied in Calu-3 airway cells which express large amounts of native CFTR as their major Cl conductance (Haws, C., Finkbeiner, W. E., Widdicombe, J. H. & Wine, J. J. (1994) *Am. J. Physiol.* 266, L502-L512). Using the outside-out patch clamp mode it was found that L-ascorbic acid induced openings of CFTR Cl channels when applied to the extracellular surface of the patched membrane. In the recording shown in FIG. 20A, two channels were activated by 100 μM L-ascorbic acid, and the average single channel open probability ($P_o$) increased from zero to 0.21±0.08 (n=4, FIG. 20B). Subsequent addition of 10 μM forskolin (a cAMP-stimulating agonist) in the continued presence of L-ascorbic acid further stimulated Cl channel activity and average $P_o$ increased to 0.54±0.12. Details of the single channel recording are illustrated in FIG. 20C. The additional cAMP-induced activation of the ascorbate-stimulated Cl channels did not alter its single channel amplitude or apparent gating kinetics. FIG. 20D shows the current-voltage relationship of the ascorbate-stimulated chloride conductance and the resulting slope conductance averaged 8.9±0.2 pS (n=4). At negative potentials no channel openings were resolved indicating Cl-over-gluconate selectivity. Cyclic AMP is the major intracellular messenger for the activation of CFTR. We tested the possibility that L-ascorbic acid increased intracellular cAMP levels [cAMP]$_i$ by either turning on cAMP production or preventing cAMP degradation. FIG. 20E compares whole cell cAMP levels of Calu-3 cells challenged with either increasing concentrations of L-ascorbic acid or the cAMP agonist forskolin. Concentrations of forskolin of 10 nM or greater increased [cAMP]$_i$ dose-dependently (FIG. 20E, filled circles). In contrast, concentrations of L-ascorbate from 100 μM to 10 mM did not result in a detectable increase of resting [cAMP]$_i$ (FIG. 20E, open circles), and a dose of 300 μM L-ascorbate did not alter the elevated cAMP level that was stimulated by 100 nM forskolin (FIG. 20E, grey circle). These data suggest that L-ascorbic acid stimulated CFTR activity by a cAMP-independent mechanism.

Example 12

Vitamin C Regulates Chloride Transport Across Human Airways in Vitro and in Vivo Vitamin C activation of CFTR-mediated Cl secretion was studied in Calu-3 cells grown as epithelial monolayers (FIG. 21A). Exposure of the apical membrane to maximal concentrations of L-ascorbic acid stimulated transepithelial Cl currents ($I_{sc}$) in a sustained fashion to 96±11 µA/cm² (n=22). Subsequent addition of forskolin further increased $I_{sc}$ to 141±33 µA/cm² (n=9, p=0.029). On average, Cl secretion was stimulated by ascorbate to 68% of the currents elicited by forskolin. The Cl channel blocker diphenylcarboxylate (DPC, 4 mM) was added as a measure for the transcellular Cl current decreasing $I_{sc}$ to 30±4 µA/cm². When Cl secretion was first stimulated with forskolin (to 106±23 µA/cm², n=4) ascorbate had no significant effect on $I_{sc}$ (at 100 µM: $\Delta I_{Cl}$=−1.5±3.5 µA/cm², n=4, not different from zero, one-sample t test). Half-maximal stimulatory constant averaged 36.5±2.9 µm as determined from transepithelial dose-response experiments. Concentrations of >300 µM caused maximal stimulation (FIG. 21B), i.e., concentrations significantly above the physiological plasma concentration (which saturate at ~90 µM (Levine, M., Conry-Cantilena, C., Wang, Y., Welch, R. W., Washko, P. W., Dhariwal, K. R., Park, J. B., Lazarev, A., Graumlich, J. F., King, J. & Cantilena, L. R. (1996) Proc. Natl. Acad. Sci. USA 93, 3704-3709).

In vivo effects of ascorbic acid on Cl transport were evaluated using the nasal potential difference (NPD) assay for Cl channel function. The Cl-selective NPD was measured in amiloride-containing (100 µm) and chloride-free solutions. These experiments served as an important control to verify the significance of the transepithelial results obtained with ascorbic acid in Calu-3 cells. In close agreement with the transepithelial measurements, NPD was progressively hyperpolarized during the exposure of the nasal mucosa to L-ascorbic acid (by −6.7±0.4 mV, n=3) and the cAMP-stimulating agonist isoproterenol (by −5.5±0.5 mV, n=4) (FIG. 21C). A dose of 300 µm L-ascorbic acid hyperpolarized NPD to 72% of the NPD in presence of the cAMP agonist isoproterenol (10 µM). This in vivo assay showed that vitamin C activated Cl transport across the nasal mucosa in human subjects similar to its in vitro effects on transepithelial Cl currents.

Example 13

Function and Expression of Sodium-dependent Vitamin C Transporters in Human Airway Epithelia.

Figure 22A:
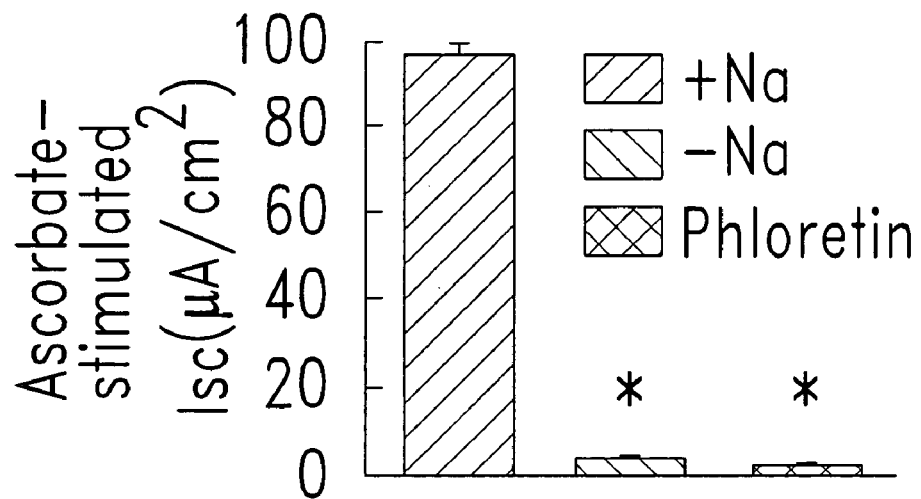
FIG. 22 shows Na-dependent vitamin C transporters in airway cells. A. Is a bar graph summary of ascorbate-stimulated Cl currents in Calu-3 monolayers in the presence (+Na) or absence (−Na) of apical Na, or after pre-treatment with 200 μM phloretin. * denotes significant difference from +Na, $p \leq 0.05$; n=6-14 experiments. B. RT-PCR analysis of SVCT1 and SVCT2 expression in hTE, Calu-3, and CF15 airway cells. GAPDH is shown as a control. 100-base pair size markers are indicated in lane 1.
Figure 22B:
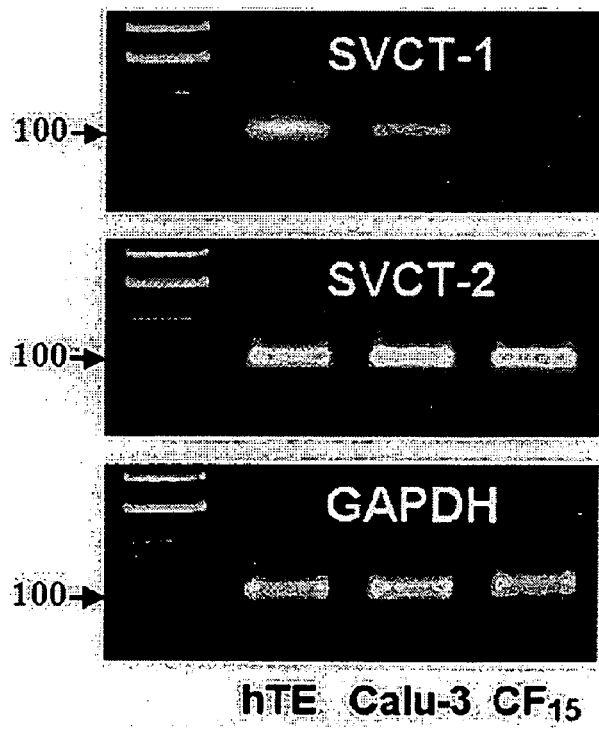

Ascorbate-stimulated Cl secretion was significantly reduced in the absence of extracellular Na on the mucosal side (FIG. 22A). Furthermore, the response to ascorbate in Na-containing medium was blunted in the presence of phloretin, a known inhibitor of the sodium-dependent vitamin C transporters SVCT1 and SVCT2 (Tsukaguchi, H., Tokui, T., Mackenzie, B., Berger, U. V., Chen, X. Z., Wang, Y., Brubaker, R. F. & Hediger, M. A. (1999) Nature 399, 70-75). These data suggested the involvement SVCT1 and/or SVCT2 during the activation of ascorbate-stimulated Cl secretion. Molecular expression of SVCT1 and SVCT2 transcripts in Calu-3 cells was verified using RT-PCR and DNA sequencing analysis. For comparison, human ciliated tracheal epithelial cultures (hTE) and a nasal cystic fibrosis airway cell line (CF15) were included. Comparison of the intensities of the specific PCR products suggested that SVCT2 was equally expressed among all tested cell types (FIG. 22B, middle panel), whereas SVCT1 was less abundant in Calu-3 and CF15 compared to hTE (FIG. 22B, top panel). DNA sequencing of the open reading frame of SVCT2 from hTE revealed that SVCT2 from trachea (GenBank accession No. AY380556; SEQ ID NO:11) was identical to the published sequence from kidney (GenBank accession No. AJ269478; SEQ ID NO:12) with the exception of one nucleotide exchange at position 1807 T→C. The recombinantly expressed SVCT2-EGFP fusion protein was targeted exclusively to the apical membrane pole of CF15 epithelia.

Example 14

Vitamin C is Specific for CFTR

Figures 23A, 23B:
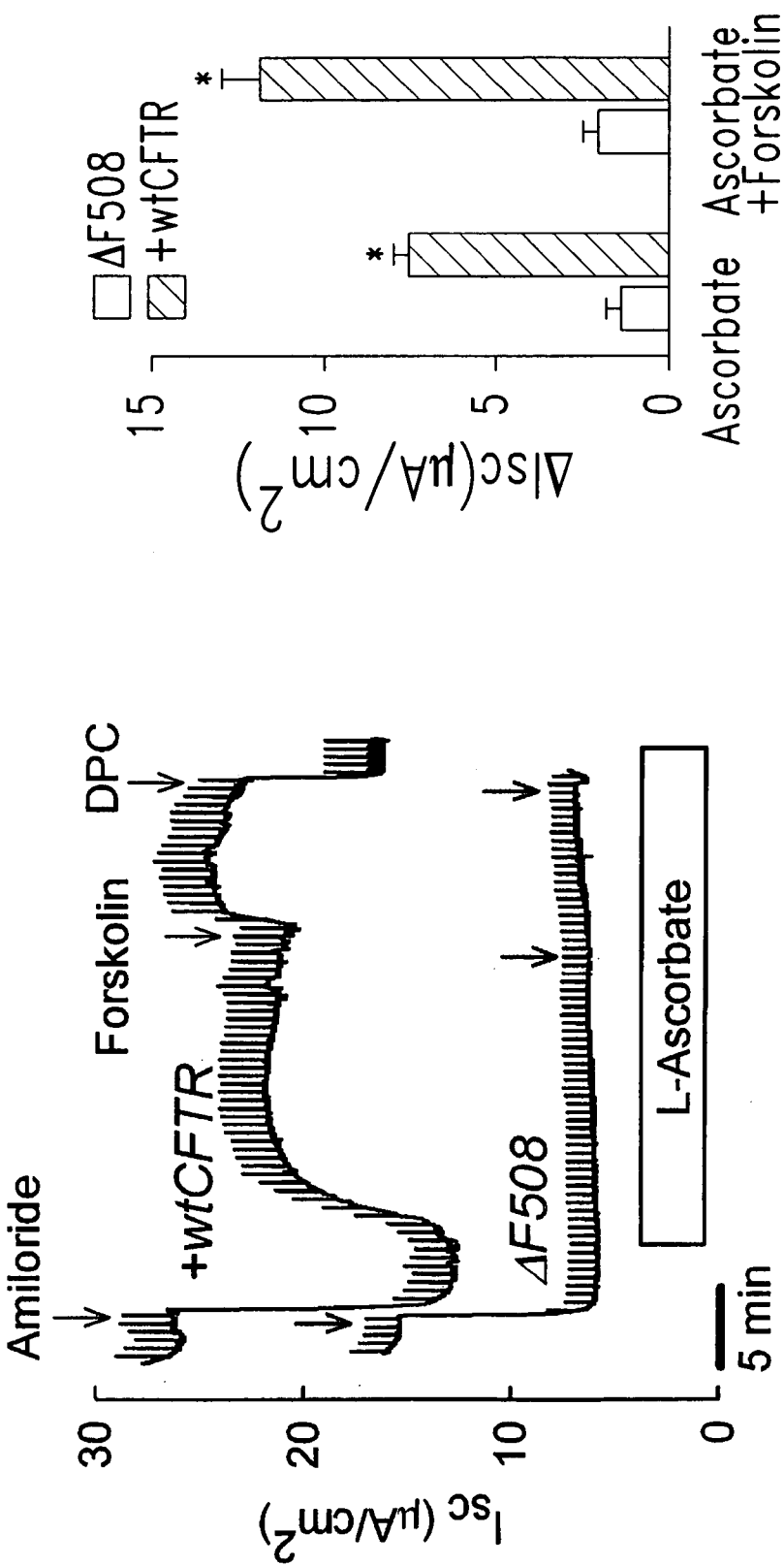
FIG. 23 shows L-ascorbic acid is specific for CFTR-mediated Cl secretion. A. Transepithelial current ($I_{sc}$) across CF15 cells. Na absorption was blocked by 20 μM amiloride. L-ascorbic acid (500 μM, mucosal) or forskolin (20 μM, serosal) stimulated Cl secretion in CFTR-corrected (+wtCFTR) but not in uncorrected CF epithelia (□F508). B. Summary of ascorbate-stimulated Cl currents in the absence (Ascorbate) and presence of forskolin (Ascorbate+Forskolin). * significantly different from ΔF508, $p \leq 0.05$; n=5-7 experiments.

The CF15 cell line was used to determine whether ascorbate-stimulated Cl currents were solely mediated by the CFTR Cl conductance. The CF15 cell line is characterized by the absence of functional CFTR in the apical plasma membrane but the presence of other non-CFTR Cl conductances (Jefferson, D. M., Valentich, J. D., Marini, F. C., Grubman, S. A., Iannuzzi, M. C., Dorkin, H. L., Li, M., Klinger, K. W. & Welsh, M. J. (1990) Am. J. Physiol. 259, L496-L505). A concentration of L-ascorbic acid that lay within the upper plateau of the dose response curve (500 µm) was applied and ascorbate-stimulated Cl currents in CF15 vs. wildtype CFTR-corrected CF15 monolayers was compared (FIG. 23A). L-ascorbic acid did not significantly increase $I_{sc}$ ($\Delta I_{sc}$=1.3±0.5 µA/cm², n=5), whereas calcium-elevating agonists effectively stimulated the calcium-activated Cl conductance in these cells (not shown). The defective response to L-ascorbic acid was reversed in wildtype CFTR-corrected CF15 epithelia such that $I_{sc}$ responded promptly to L-ascorbic acid ($\Delta I_{sc}$=7.5±0.5 µA/cm², n=6). The ascorbate-stimulated current was further activated by the cAMP agonist forskolin and total stimulated $I_{sc}$ averaged 12.1±1.1 µA/cm² (FIG. 4B). The ascorbate-stimulated Cl current reached 60±15% of the forskolin-stimulated current in CFTR-corrected CF15 monolayers, which was close to the corresponding findings in Calu-3 monolayers (68%, see FIG. 21A). The absence of ascorbate-stimulated Cl currents in CF15 monolayers supports the notion that non-CFTR Cl conductances were not activated by L-ascorbic acid. These experiments demonstrated a causal relationship between CFTR expression and ascorbate stimulation in epithelia.

Example 15

Stimulation of Rectal Potential Difference (RPD) in Rescue Compound-treated CF Mice in Vivo.

In this Example, it was determined whether L-ascorbic acid affected the functional activation of ΔF508 CFTR in a CF-affected organism in vivo. Using gene-targeted mice homozygous for the ΔF508 mutation it was shown previously that the osmolyte trimethylamine oxide (TMAO) effectively supported ΔF508 CFTR trafficking in vivo (Fischer, H., Barbry, P., Illek, B., Sartori, C., Fukuda, N. & Matthay, M. A. (2001) Am. J. Physiol. 281, L52-L57). Accordingly, the effect of L-ascorbic acid was tested in homozygous ΔF508 CF mice treated with TMAO by using the RPD assay as a functional end point measure for mutant ΔF508-CFTR function. FIG. 24A illustrates that TMAO-treated CF mice manifested a detectable response to a maximal dose of L-ascorbic acid (1 mM) or its epimer D-isoascorbic acid (300 μM) and RPD hyperpolarized on average by −3.2±0.8 mV (n=4) and −3.6±1.8 mV (n=3), respectively (FIG. 24B). In contrast, perfusion with L-ascorbic acid or D-isoascorbic acid did not substantially alter RPD in water-injected control CF mice (ΔRPD=−1.1±0.4 mV, n=9). TMAO treatment increased the ascorbate- and isoascorbate-stimulated RPD approximately 3-fold when compared to untreated CF mice (FIG. 24B) indicating the activation of outward Cl ion movement through functionally restored ΔF508-CFTR channels in the rectal mucosa of CF mice. The results show that both L-ascorbate and D-isoascorbate are pharmacological tools for the activation of ΔF508-mutated CFTR after its trafficking defect has been corrected.

Example 16

Stimulation of Chloride Ion Transport by L-ascorbate and D-isoascorbate in Cystic Fibrosis Nasal Epithelia in Vitro.

Figure 25D:
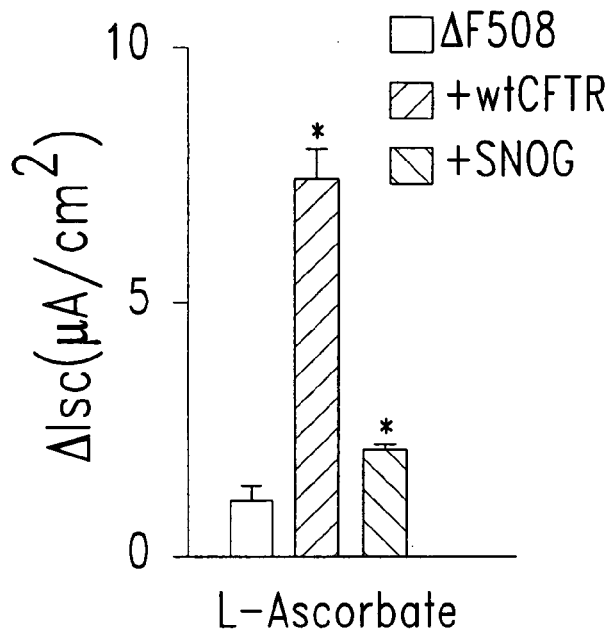
FIG. 25 shows activation of ΔF508 CFTR by L-ascorbic acid and D-isoascorbic acid after correction of the trafficking defect in CF15 nasal epithelial cells using genetic or pharmacologic strategies. A-H. Measurements of transepithelial Cl currents ($I_{sc}$) in amiloride-treated CF15 monolayers homozygous for ΔF508 CFTR. Arrow indicates perfusion with L-ascorbate (1 mM) or D-isoascorbate (300 μM). $I_{sc}$ was stimulated by both ascorbates in CF15 monolayers recombinantly expressing wildtype CFTR (B,F) or were treated with 1 mM S-Nitrosoglutathione for 5-24 hours (C,G), but not in untreated CF nasal cells (A,E). D,H. Summary of ascorbate-induced changes in RPD in TMAO-treated and control CF mice. ctrl, control; L-Asc, 1 mM L-ascorbate; D-Iasc, 300 μM D-isoascorbate. * significantly different from untreated CF15 nasal epithelia, $p \leq 0.05$; n=2-13 experiments.
Figure 25H:
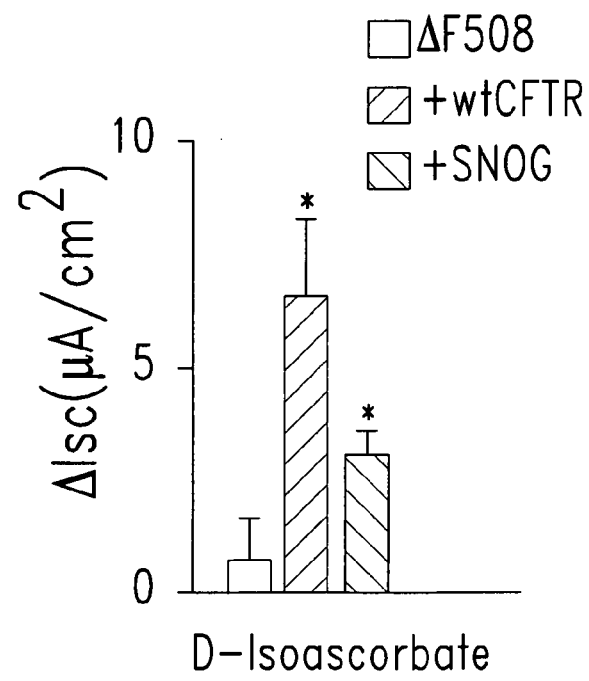

In this example, chloride currents stimulated by L-ascorbate or D-ascorbate were measured in CF15 versus. wildtype CFTR-corrected CF15 monolayers. A concentration of L-ascorbate (1 mM) or D-isoascorbate (300 μm) that lay within the upper plateau of the dose-response curve was applied to cells and the resulting chloride currents stimulated in CF15 versus wildtype CFTR-corrected CF15 monolayers were measured (FIG. 25 A-H). All experiments were performed in the presence of the sodium channel blocker amiloride. In untreated cystic fibrosis epithelia, chloride currents were not significantly stimulated by L-ascorbate (ΔIsc=1.1±0.3 μA/cm², n=13) (FIG. 25A) nor D-isoascorbate (ΔIsc=0.7±1.0 μA/cm², n=7) (FIG. 25E). The defective responses to L-ascorbate and D-lsoascorbate were reversed after gene therapy such that wildtype CFTR-corrected CF15 epithelia $I_{Cl}$ responded promptly to L-ascorbate (ΔIsc=7.5±0.5 μA/cm2, n=6) or D-isoascorbate (ΔIsc=6.6±1.7 μA/cm², n=2). These experiments confirm the results described in Examples 14 and 15 and demonstrate a causal relationship between CFTR expression and the chloride secretory response to both L-ascorbate and D-isoascorbate.

The functional activation of ΔF508 CFTR was determined after correction of the underlying trafficking defect of ΔF508 CFTR using S-Nitrosoglutathione (Zaman, et al., Biochem Biophys Res Commun 284: 65-70, 2001; Snyder, et al., American Journal of Respiratory and Critical Care Medicine 165: 922-6, 2002; Andersson, et al. Biochemical and Biophysical Research Communication 297(3): 552-557, 2002.). CF15 monolayers were treated with 1 mM S-Nitrosoglutathione (SNOG) for 5-24 hours to support trafficking of ΔF508 CFTR to the plasma membrane. SNOG-treated CF 15 monolayers manifested a detectable response to L-ascorbate and D-isoascorbate and transepithelial chloride currents increased on average by 2.1±0.1, n=10 (L-ascorbate, FIG. 25C) and 3.1±0.5, n=8 (D-lsoascorbate, FIG. 25G). SNOG treatment recovered the ascorbate and isoascorbate-stimulated Cl secretion between 28-47% when compared to wildtype CFTR corrected CF15 cells. The summary in FIG. 25D and 25G compares the magnitudes of the L-ascorbate and D-isoascorbate stimulated Cl currents in cystic fibrosis epithelial. These results show that both L-ascorbate and D-isoascorbate are pharmacological tools for the activation of ΔF508 mutated CFTRS after its trafficking defect has been corrected.

From the foregoing it will be appreciated that, although specific embodiments of the invention have been described herein for purposes of illustration, various modifications may be made without deviating from the spirit and scope of the invention. Accordingly, the invention is not limited except as by the appended claims. All of references, patents, patent applications, etc. cited above, are incorporated herein in their entirety. Further, all numerical ranges recited herein explicitly include all integer values within the range.

What is claimed is:

1. A method for treating a disease characterized by defective chloride transport in a mammal consisting essentially of administering to a mammal afflicted with the disease, one or more compounds selected from the group consisting of ascorbic acid, ascorbate salts, dehydroascorbic acid and resveratrol, wherein the disease is selected from the group consisting of cystic fibrosis, obstructive airway disease, intestinal constipation, pancreatitis, and dry eye syndrome.

2. A method for treating a disease characterized by defective chloride transport in a mammal, the method consisting essentially of:
   (a) administering, to a mammal afflicted with the disease, one or more of ascorbic acid, ascorbate salts, dehydroascorbic acid and resveratrol; and
   (b) administering to the mammal one or more compounds selected from the group consisting of flavones and isoflavones, wherein the flavone or isoflavone is capable of stimulating chloride transport, wherein the flavone or isoflavone is not genistein; and wherein the disease is selected from the group consisting of cystic fibrosis, obstructive airway disease, intestinal constipation, pancreatitis, and dry eye syndrome.

3. The method of claim 2 wherein the flavone or isoflavone is selected from the group consisting of quercetin, apigenin, kaempferol, biochanin A, flavanone, flavone, dihydroxyflavone, trimethoxy-apigenin, apigenin 7-O-neohesperidoside, fisetin, rutin, daidzein and prunetin.

4. The method of claim 1 wherein the compound is administered orally.

5. The method of claim 1 wherein the compound is administered by inhalation.

6. The method of claim 1 wherein the compound is administered topically.

7. A method for treating cystic fibrosis or asthma in a mammal comprising a. administering to a mammal afflicted with cystic fibrosis or asthma one or more compounds selected from the group consisting of ascorbic acid, ascorbate salts, dehydroascorbic acid and resveratrol;
   b. administering to the mammal one or more compounds selected from the group consisting of flavones and isoflavones, wherein the compound is capable of stimulating chloride transport; and
   c. administering to the mammal one or more compounds selected from the group consisting of
      (i) a compound that increases expression of a CFTR in an epithelial cell; and
      (ii) a chemical chaperone that increases trafficking of a CFTR to a plasma membrane in an epithelial cell.

8. The method of claim 1 or claim 7 wherein the compound is present within a composition comprising a physiologically acceptable carrier or excipient.

9. A method for treating a disease characterized by defective chloride transport in a mammal comprising administering to a mammal afflicted with the disease, a composition consisting essentially of one or more compounds selected from the group consisting of ascorbic acid, ascorbate salts, dehydroascorbic acid and resveratrol, wherein the disease is selected from the group consisting of cystic fibrosis, obstructive airway disease, intestinal constipation, pancreatitis, and dry eye syndrome.

10. A method for treating a disease characterized by defective chloride transport in a mammal comprising administering to a mammal afflicted with the disease, a composition comprising resveratrol, wherein the disease is selected from the group consisting of asthma, cystic fibrosis, obstructive airway disease, intestinal constipation, pancreatitis, and dry eye syndrome.

\* \* \* \* \*

UNITED STATES PATENT AND TRADEMARK OFFICE
CERTIFICATE OF CORRECTION

| | | |
|---|---|---|
| PATENT NO. | : 7,718,694 B2 | Page 1 of 1 |
| APPLICATION NO. | : 10/769619 | |
| DATED | : May 18, 2010 | |
| INVENTOR(S) | : Horst Fischer et al. | |

It is certified that error appears in the above-identified patent and that said Letters Patent is hereby corrected as shown below:

In the Specification

Column 1, Lines 18-21:
"This invention was made with government support under Grant No. R01 HL071829 awarded by the National Institutes of Health. The government may have certain rights in this invention." should read, --This invention was made with government support under Grant No. R01 HL071829 awarded by the National Institutes of Health. The government has certain rights in this invention.--.

Signed and Sealed this
Twenty-second Day of April, 2014

Michelle K. Lee
*Deputy Director of the United States Patent and Trademark Office*